United States Patent
Ang et al.

(10) Patent No.: US 8,399,453 B2
(45) Date of Patent: *Mar. 19, 2013

(54) ORGANIC COMPOUNDS

(75) Inventors: Shi Hua Ang, Singapore (SG); Philipp Krastel, Grenzach-Wyhlen (DE); Seh Yong Leong, Singapore (SG); Liying Jocelyn Tan, Singapore (SG); Wei Lin Josephine Wong, Singapore (SG); Bryan K. S. Yeung, Singapore (SG); Bin Zou, Singapore (SG)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,035

(22) Filed: Jul. 19, 2011

(65) Prior Publication Data

US 2011/0275613 A1 Nov. 10, 2011

Related U.S. Application Data

(63) Continuation of application No. 12/430,625, filed on Apr. 27, 2009.

(30) Foreign Application Priority Data

Apr. 29, 2008 (EP) ..................................... 08155342
Jan. 22, 2009 (EP) ..................................... 09151117

(51) Int. Cl.
*A61K 31/55* (2006.01)
*A61K 31/407* (2006.01)
*A61K 31/438* (2006.01)
*C07D 471/20* (2006.01)
*C07D 487/20* (2006.01)

(52) U.S. Cl. ................... 514/212.02; 514/278; 514/409; 546/18; 540/466; 540/543

(58) Field of Classification Search ............. 514/212.02, 514/278, 409; 540/543, 466; 546/18
See application file for complete search history.

(56) References Cited

U.S. PATENT DOCUMENTS

2009/0275560 A1* 11/2009 Ang et al. ................ 514/212.02

FOREIGN PATENT DOCUMENTS

| EP | 0 466 548 A1 | 1/1992 |
|---|---|---|
| EP | 0466548 | 1/1992 |
| WO | 00/37470 | 6/2000 |
| WO | WO 2005/009370 A | 2/2005 |
| WO | 2006/110654 A1 | 10/2006 |
| WO | 2008/068185 A1 | 6/2008 |
| WO | 2009/089454 A1 | 7/2009 |

OTHER PUBLICATIONS

Brouwer et al., The Reaction Between Isatin and Some Amines, 1972, J.C.S. Perkin I, (1), 124-129.*
Wolff et al., Burger's Medicinal Chemistry and Drug Discovery, 1994, Wiley-Interscience, Fifth Edition, vol. I: Principles and Practice, pp. 975-977.*
Bremner et al., "A Compact Approach to an Isomeric Iheyamine. A System and X-ray Crystal Structure of 5-Methyl-5*H*-azepino[2,3-*b*:4,5-*b*']diindole," Synth. Commun. 38, 1931-39, 2008.
Chiyanzu et al., "Design, synthesis and anti-plasmodial evaluation in vitro of new 4-aminoquinoline isatin derivatives," Bioorganic & Medicinal Chemistry 13, 3249-61, 2005.
Grigoryan et al., "The Synthesis and Anti-Spasmodic Activity of 2'-oxo-(5'-bromo)indoline-3'-spiro-1/(1,2,3,4-tetrahydro)-β-carbolines and 3'-spiro-1-/1,2,3,4,5,10-hexahydro)-indolo(2,3-c)/azepines," Khimicheskiy Zhurnal Armenii 58, pp. 1-5 as translated, 2005.
Hudson, "Patent focus on antiparasitic agents: May-Oct. 1999," Exp. Opin. Ther. Patents, 10(2), pp. 153-163, 2000.
International Search Report, PCT/EP2009/053902, mailed May 28, 2009.
Khimicheskiy Zhurnal Amenii, "The Synthesis and Anti-Spasmodic Activity of 2'-OXO-(5'-Bromo)Indoline-3'-Spiro-1/(1,2,3,4-Tetrahydro)-β-Carbolines and 3'-Spiro-1-/(1,2,3,4,5,10-Hexahydro)-indolo(2,3-c)/Azepines," National Academy of Sciences of the Republic of Armenia, 2005, 58(3), 1-6.
Medvedev et al., "Inhibitory potency of some isatin analogues on human monoamine oxidase A and B," Biochem. Pharmacol. 44, 590-92, 1992.
Pogosyan et al., "Synthesis and anticonvulsant activity of dihydrochlorides of indoline-3'-spiro-1-(1,2,3,4-tetrahydro-b-carboline derivatives," Pharm.Chem.J. 41, 527-28, 2007.

* cited by examiner

*Primary Examiner* — Kristin Bianchi
(74) *Attorney, Agent, or Firm* — Banner & Witcoff, Ltd.

(57) ABSTRACT

The invention relates to organic compounds which have interesting pharmaceutical properties. In particular, the compounds are useful in the treatment and/or prevention of infections such as those caused by *Plasmodium falciparum*, *Plasmodium vivax*, *Plasmodium malariae*, *Plasmodium ovale*, *Trypanosoma cruzi* and parasites of the *Leishmania* genus such as, for example. *Leishmania donovani*. The invention also relates to pharmaceutical compositions containing the compounds, as well as processes for their preparation.

10 Claims, No Drawings

ORGANIC COMPOUNDS

TECHNICAL FIELD

This invention is directed to, inter alia, novel compounds which are useful as pharmaceuticals. The invention is also directed to pharmaceutical compositions containing the compounds, processes for their preparation and uses of the compounds in various medicinal applications, such as for the treatment of parasitic diseases, e.g. malaria, leishmaniasis and Chagas disease. Compounds are also provided which are useful as intermediate for example the Boc compounds)

BACKGROUND

Malaria, is an old infectious disease caused by four protozoan parasites, *Plasmodium falciparum*, *Plasmodium vivax*, *Plasmodium malariae* and *Plasmodium ovale*. These four parasites are typically transmitted by the bite of an infected female *Anopheles* mosquito. Malaria is a problem in many parts of the world, and over the last few decades the malaria burden has steadily increased. An estimated 1 to 3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Leishmaniasis is caused by one of more than twenty (20) varieties of parasitic protozoa that belong to the genus *Leishmania*, and is transmitted by the bite of female sandflies. Leishmaniasis is endemic in some 90 countries, including many tropical and sub-tropical areas.

There are four main forms of leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harbouring the human pathogenic parasites.

Chagas disease (also called American trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after the infection, and the chronic stage, which can develop over many years. Chronic infections result in various neurological disorders, including dementia, damage to the heart muscle and sometimes dilation of the digestive tract, as well as weight loss. Untreated, the chronic disease is often fatal.

The drugs currently available for treating Chagas disease are nifurtimox and benznidazole. However, problems with these current therapies include their adverse side effects, the length of treatment, and the requirement for medical supervision during treatment. Furthermore, treatment is really only effective when given during the acute stage of the disease. Resistance to the two frontline drugs has already arisen. The antifungal agent amphotericin b has been proposed as a second-line drug, but this drug is costly and relatively toxic.

In view of the foregoing, it is desirable to develop novel compounds for evaluation and use as antiparasitic agents.

SUMMARY OF INVENTION

In a first aspect, the invention provides a compound of formula (I), or a pharmaceutically acceptable salt, ester or prodrug thereof (I)

wherein m is 1 or 2;

R1 is H, halogen, alkyl, haloalkyl, alkoxy, amine or aryl optionally substituted with one or more substituents R2 is H, alkyl, arylalkyl or alkoxycarbonyl;

either (i) R3 is H or alkyl;

R4 is H, alkyl, hydroxyalkyl, —COOD wherein D is an alkyl group or (ii) R3 and R4 form part of a heterocyclo ring; R5 is H or alkyl;

n is 1, 2 or 3; and

A and B are fused to, and form part of, an unsubstituted or substituted monocyclic or polycyclic arene or heteroarene;

provided that if A and B are fused to and take the part of positions 2 and 3 of an unsubstituted indole, n is 1 or 2, R2 and R3 are H, m is 1 and R1 is in position 6 of the spiro oxindole, then (i) R1, R4 and R5 are not all H; or (ii) if R1 is H, then (a) R4 is not methyl when R5 is H and (b) R5 is not methyl when R4 is H; or (iii) if R1 is Br, then (a) R4 and R5 are not both H, and (b) R4 is not methyl when R5 is H, and (c) R5 is not methyl when R4 is H.

Haloalkyl is preferably trifluoromethyl. Amino may be eg substituted by one or two substituents eg lower alkyl.

In the above formula, R1 may be, for example, F, Cl, Br, methyl, —CF, —OCH$_3$, —N(CH$_3$)$_2$, —C$_6$H$_5$, —(C$_6$H$_4$)CF$_3$ or —(C$_6$H$_4$)O(C$_6$H$_5$). In some examples, R1 may be di-Cl when m is 2. In other examples R1 may be Cl when m is 1. Conveniently the R1 may be para or ortho to the nitrogen atom (position 5 or 6 of the spiro).

R2 may be eg methyl, Bn or Boc (for the meanings of abbreviations please see later).

R3 may be methyl. R4 may be methyl, ethyl, propyl, isopropyl, —CH$_2$OH, —COOCH$_3$ or —COOCH$_2$CH$_3$. In some examples, R3 and R4 may together form a di-valent substituent of formula (i):

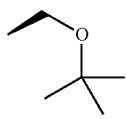
(i)

In some examples, R4 and R5 may both be methyl.

A and B may be fused to and form part of imidazole, benzene or indole. In some examples, A and B may be fused to and form part of benzene substituted with an electron donating group (EDG) in one of the 4 remaining positions. In other examples, A and B may be fused to and form part of a substituted indole of formula (a):

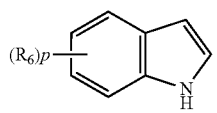
(a)

p may be 1, 2, 3 or 4 and R6 may be one or more of a group comprising halogen, haloalkyl, alkoxy, hydrogen, hydroxyl, and nitrile.

or (b):

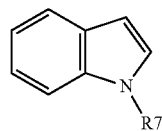
(b)

wherein R7 may be alkyl, alkoxycarbonyl, aryl carbonyl or aryl sulfonyl.

A and B form part of the 2 and 3 positions of the indole.

In some examples, R6 may be Cl, CF$_3$, or —OCH$_3$.

In some examples, R7 may be methyl, Boc or a substituent of formula (ii), (iii), (iv) or (v):

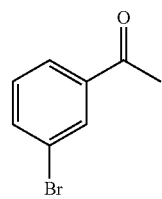
(ii)

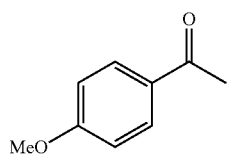
(iii)

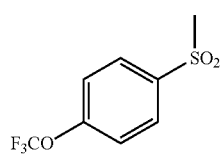
(iv)

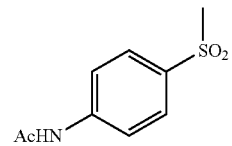
(v)

In one embodiment, the invention relates to compound, or a pharmaceutically acceptable salt, ester or prodrug thereof, of the formula:

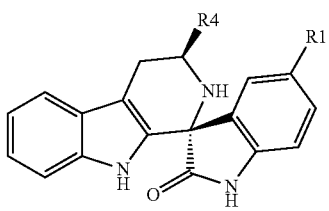
(Ia)

wherein

R1 is a halogen; and

R4 is alkyl, hydroxyalkyl or —COOD wherein D is an alkyl group;

provided that if R1 is Br, R4 is not methyl.

In the above formula, R1 may be Br or Cl and R4 may be methyl, ethyl, propyl, isopropyl, —CH$_2$OH, —COOCH$_3$ or —COOCH$_2$CH$_3$.

In one embodiment, the invention relates to a compound, or a pharmaceutically acceptable salt, ester or prodrug thereof, of the formula:

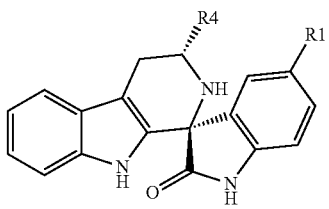
(Ib)

wherein

R1 is a halogen; and

R4 is alkyl, hydroxyalkyl or —COOD wherein D is an alkyl group;

provided that if R1 is Br, R4 is not methyl.

In the above formula, R1 may be Br or Cl and R4 may be methyl, ethyl, propyl, isopropyl, —CH$_2$OH, —COOCH$_3$ or —COOCH$_2$CH$_3$.

In one embodiment, the invention relates to a compound, or a pharmaceutically acceptable salt, ester or prodrug thereof, of the formula:

(Ic)

wherein R7 is aryl carbonyl or aryl sulfonyl.

In the above formula, R7 may be a substituent of formula (ii), (iii), (iv) or (v) as defined above for the compound of formula (I).

In one embodiment, the invention relates to a compound, or a pharmaceutically acceptable salt, ester or prodrug thereof, of the formula:

(Id)

In one embodiment, the invention relates to a compound, or a pharmaceutically acceptable salt, ester or prodrug thereof, of the formula:

(Ie)

wherein R4 is alkyl.

In one embodiment, the invention relates to a compound, or a pharmaceutically acceptable salt, ester or prodrug thereof, of the formula:

(If)

wherein R4 is alkyl.

In the above formula, R4 ethyl or ethyl.

In one embodiment, the invention relates to a compound, or a pharmaceutically acceptable salt, ester or prodrug thereof, of the formula:

(Ig)

wherein
R1 is halogen or aryl optionally substituted with one or more substituents;
R2 is H, alkyl, arylalkyl or alkoxycarbonyl;
R4 is H or alkyl;
R5 is H or alkyl; and
R7 is H, alkyl, alkoxycarbonyl, aryl carbonyl or aryl sulfonyl,
provided that if R2 and R7 are H, then
R1, R4 and R5 are not all H; or
if R1 is H, then R4 is not methyl when R5 is H and R5 is not methyl when R4 is H; or
if R1 is Br, then R4 and R5 are not both H, and R4 is not methyl when R5 is H, and R5 is not methyl when R4 is H.

In the above formula, R1 may be Br, Cl, F, —C$_6$H$_5$, —(C$_6$H$_4$)CF$_3$ or —(C$_6$H$_4$)O(C$_6$H$_5$). R2 may be methyl, Bn or Boc. R4, R5 or both R4 and R5 may be methyl. R7 may be methyl, Boc or a substituent of formula (ii), (iii), (iv) or (v) as defined above for the compound of formula (I).

In one embodiment, the invention relates to a compound, or a pharmaceutically acceptable salt, ester or prodrug thereof, of the formula:

(Ih)

wherein
m is 1 or 2;
R1 is H, halogen, alkyl, haloalkyl, alkoxy or amine;
R3 is H or alkyl;
R4 is H or alkyl;
R5 is H or alkyl; and
R6 is H, halogen, haloalkyl or alkoxy;
provided that if R3 and R6 are H, in m is 1 and R1 is in position 6 of the spiro oxindole, then
(i) R1, R4 and R5 are not all H; or
(ii) if R1 is H, then (a) R4 is not methyl when R5 is H and (b) R5 is not methyl when R4 is H; or
(iii) if R1 is Br, then (a) R4 and R5 are not both H, and (b) R4 is not methyl when R5 is H, and (c) R5 is not methyl when R4 is H.

In the above formula, R1 may be F, Cl, Br, methyl, —CF$_3$, —OCH$_3$ or —N(CH$_3$)$_2$ and R6 may be Cl, —CF$_3$ or —OCH$_3$. In some examples, R1 may be di-Cl when m is 2.

In one embodiment, the invention relates to a compound, or a pharmaceutically acceptable salt, ester or prodrug thereof, of the formula:

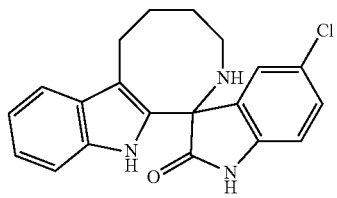
(Ii)

In one embodiment, the invention relates to a compound, or a pharmaceutically acceptable salt, ester or prodrug thereof, of the formula:

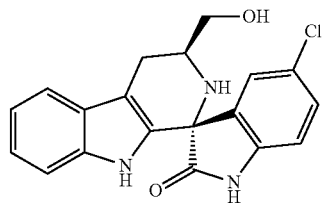
(Ij)

In one embodiment, the invention relates to a compound, or a pharmaceutically acceptable salt, ester or prodrug thereof, of the formula:

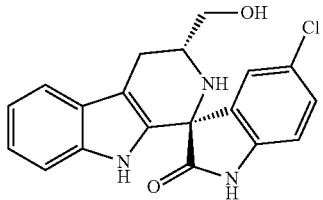
(Ik)

In one embodiment, the invention relates to a compound, or a pharmaceutically acceptable salt, ester or prodrug thereof, of the formula:

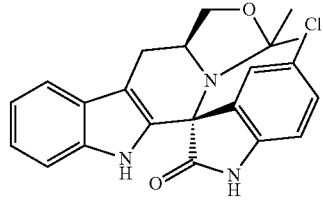
(Il)

In one embodiment, the invention relates to a compound, or a pharmaceutically acceptable salt, ester or prodrug thereof, of the formula:

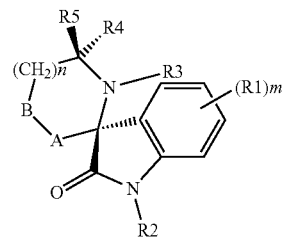
(Im)

wherein
m is 1 or 2;
R1 is H, halogen, alkyl, haloalkyl, alkoxy, amine or aryl optionally substituted with one or more substituents;
R2 is H, alkyl, arylalkyl or alkoxycarbonyl;
R3 is H or alkyl;
R4 is H, alkyl, hydroxyalkyl, —COOD wherein D is an alkyl group or R3 and R4 form part of a heterocyclo ring;
R5 is H or alkyl;
n is 1, 2 or 3; and
A and B are fused to and form part of an unsubstituted or substituted monocyclic or polycyclic arene or heteroarene;
provided that if A and B are fused to positions 2 and 3 of an unsubstituted indole, n is 1 or 2, R2 and R3 are H, m is 1 and R1 is in position 6 of the spiro oxindole, then
R1, R4 and R5 are not all H; or
if R1 is H, then R4 is not methyl when R5 is H and R5 is not methyl when R4 is H; or
if R1 is Br, then R4 and R5 are not both H, and R4 is not methyl when R5 is H, and R5 is not methyl when R4 is H.

In the above formula, R1 may be F, Cl, Br, methyl, —CF$_3$, —OCH$_3$, —N(CH$_3$)$_2$, —C$_6$H$_5$, —(C$_6$H$_4$)CF$_3$ or —(C$_6$H$_4$)O(C$_6$H$_5$). In some examples, R1 may be di-Cl when m is 2. R2 may be methyl, Bn or Boc. R3 may be methyl. R4 may be methyl, ethyl, propyl, isopropyl, —CH$_2$OH, —COOCH$_3$ or —COOCH$_2$CH$_3$. In some examples, R4 and R5 may both be methyl. A and B may be fused to imidazole, benzene or indole. In some examples, A and B may be fused to benzene substituted with an electron donating group (EDG). In other examples. A and B may be fused to a substituted indole of formula (a) or (b) as defined above.

In one embodiment, the invention relates to a compound, or a pharmaceutically acceptable salt, ester or prodrug thereof, of the formula:

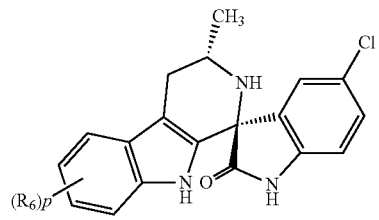
(In)

wherein p may be 1, 2, 3 or 4 and R6 may be one or more of a group comprising halogen, haloalkyl and alkoxy.

In one embodiment, the invention relates to a compound, or a pharmaceutically acceptable salt, ester or prodrug thereof, of the formula:

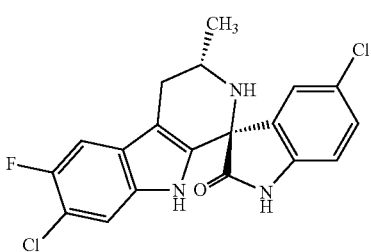

(Io)

In one embodiment, the invention relates to a compound, or a pharmaceutically acceptable salt, ester or prodrug thereof, of the formula:

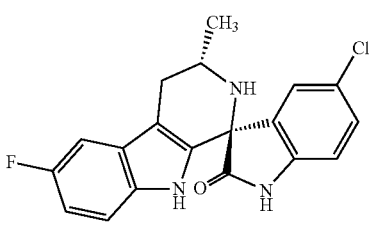

(Ip)

In another aspect, the invention provides a compound of formula (II), or a pharmaceutically acceptable salt, ester or prodrug thereof:

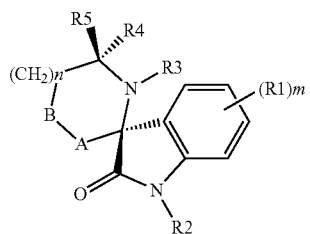

(II)

wherein:
m is 1 or 2;
R1 is H, halogen, alkyl, haloalkyl, amine or aryl optionally substituted with one or more substituents;
R2 is H, alkyl, arylalkyl or alkoxycarbonyl;
R3 is H or alkyl;
R4 is H, alkyl, hydroxyalkyl, —COOD wherein D is an alkyl group or R3 and R4 form part of a heterocyclo ring;
R5 is H or alkyl;
n is 1, 2 or 3; and
A and B are fused to and form part of an unsubstituted or substituted monocyclic or polycyclic arene or heteroarene.

In the above formula, R1 may be F, Cl, Br, methyl, —CF$_3$, —OCH$_3$, —N(CH$_3$)$_2$, —C$_6$H$_5$, —(C$_6$H$_4$)CF$_3$ or —(C$_6$H$_4$)O(C$_6$H$_5$). In some examples, R1 may be di-Cl when m is 2. R2 may be methyl, Bn or Boc. R3 may be methyl. R4 may be methyl, ethyl, propyl, isopropyl, —CH$_2$OH, —COOCH$_3$ or —COOCH$_2$CH$_3$. In some examples, R4 and R5 may both be methyl. A and B may be fused to imidazole, benzene or indole. In some examples, A and B may be fused to benzene substituted with an electron donating group (EDG). In other examples, A and B may be fused to a substituted indole of formula (a) or (b) as defined above for the compound of formula (I).

In another aspect, the invention provides a pharmaceutical composition comprising a compound of formula (I) or (II) or a compound of any of formulae (Ia) to (Ip) as defined above, or a pharmaceutically acceptable salt, ester or prodrug thereof, in combination with at least one pharmaceutically acceptable excipient, e.g. appropriate diluent and/or carrier, e.g. including fillers, binders, disintegrators, flow conditioners, lubricants, sugars or sweeteners, fragrances, preservatives, stabilizers, wetting agents and/or emulsifiers, solubilisers, salts for regulating osmotic pressure and/or buffers, and optionally a second drug substance. The pharmaceutical composition may be used for the treatment and/or prevention of a disease caused by a parasite such as *Plasmodium falciparum, Plasmodium vivax, Plasmodium malariae, Plasmodium ovale, Trypanosoma cruzi* or a parasite of the *Leishmania* genus such as, for example, *Leishmania donovani*. The disease may be malaria, leishmaniasis or Chagas disease.

In another aspect, the invention provides a compound of formula (I) or (II) or a compound of any of formulae (Ia) to (Ip) as defined above, or a pharmaceutically acceptable salt, ester or prodrug thereof, optionally a second drug substance, for use as a medicament.

In another aspect the invention provides the use of a compound of formula (III), or a pharmaceutically acceptable salt, ester or prodrug thereof, for the manufacture of a medicament, e.g. a pharmaceutical composition, for the treatment and/or prevention of a parasitic infection:

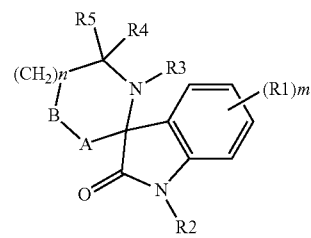

(III)

wherein
m is 1 or 2;
R1 is H, halogen, alkyl, haloalkyl, alkoxy, amine or aryl optionally substituted with one or more substituents;
R2 is H, alkyl, arylalkyl or alkoxycarbonyl;
R3 is H or alkyl;
R4 is H, alkyl, hydroxyalkyl, —COOD wherein D is an alkyl group or R3 and R4 form part of a heterocyclo ring;
R5 is H or alkyl;
n is 1, 2 or 3; and
A and B are fused to and form part of an unsubstituted or substituted monocyclic or polycyclic arene or heteroarene.

In the above formula, R1 may be F, Cl, Br, methyl, —CF$_3$, —OCH$_3$, —N(CH$_3$)$_2$, —C$_6$H$_5$, —(C$_6$H$_4$)CF$_3$ or —(C$_6$H$_4$)O(C$_6$H$_5$). In some examples, R1 may be di-Cl when m is 2. R2 may be methyl, Bn or Boc. R3 may be methyl. R4 may be methyl, ethyl, propyl, isopropyl, —CH$_2$OH, —COOCH$_3$ or —COOCH$_2$CH$_3$. In some examples, R3 and R4 may together form a substituent of formula (i) as defined above. In some examples, R4 and R5 may both be methyl. A and B may be fused to imidazole, benzene or indole. In some examples, A and B may be fused to benzene substituted with an electron donating group (EDG). In other examples, A and B may be fused to a substituted indole of formula (a) or (b) as defined above for the compound of formula (I).

In one embodiment, the invention relates to the use of a compound of formula (I) or (II) or a compound of any of formulae (Ia) to (Ip) as defined above, or a pharmaceutically acceptable salt, ester or prodrug thereof, for the manufacture of a medicament, e.g. a pharmaceutical composition, for the treatment and/or prevention of a parasitic infection.

In one embodiment, the invention relates to the use of a compound of formula (IIIa), or a pharmaceutically acceptable salt, ester or prodrug thereof, for the manufacture of a medicament, e.g. a pharmaceutical composition, for the treatment and/or prevention of a parasitic infection:

In one embodiment, the invention relates to the use of a compound of formula (IIIa), or a pharmaceutically acceptable salt, ester or prodrug thereof, for the manufacture of a medicament, e.g. a pharmaceutical composition, for the treatment and/or prevention of a parasitic infection:

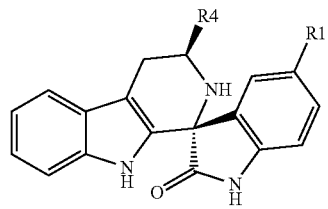

(IIIa)

wherein
R1 is a halogen; and
R4 is alkyl, hydroxyalkyl or —COOD wherein D is an alkyl group.

In the above formula R1 may be Br or Cl and R4 may be methyl, ethyl, propyl, isopropyl, —CH$_2$OH, —COOCH$_3$ or —COOCH$_2$CH$_3$.

In one embodiment, the invention relates to the use of a compound of formula (IIIb), or a pharmaceutically acceptable salt, ester or prodrug thereof, for the manufacture of a medicament, e.g. a pharmaceutical composition, for the treatment and/or prevention of a parasitic infection:

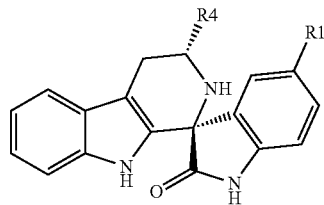

(IIIb)

wherein
R1 is a halogen; and
R4 is alkyl, hydroxyalkyl or —COOD wherein D is an alkyl group.

In the above formula, R1 may be Br or Cl and R4 may be methyl, ethyl, isopropyl, —CH$_2$OH, —COOCH$_3$ or —COOCH$_2$CH$_3$.

In one embodiment, the invention relates to the use of a compound of formula (IIIc), or a pharmaceutically acceptable salt, ester or prodrug thereof, for the manufacture of a medicament, e.g. a pharmaceutical composition, for the treatment and/or prevention of a parasitic infection:

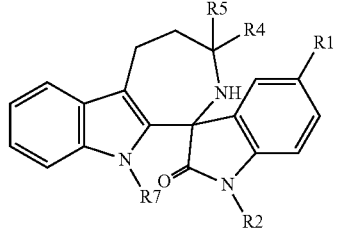

(IIIc)

wherein
R1 is halogen or aryl optionally substituted with one or more substituents;
R2 is H, alkyl, arylalkyl or alkoxycarbonyl;
R4 is H or alkyl;
R5 is H or alkyl; and
R7 is H, alkyl, alkoxycarbonyl, aryl carbonyl or aryl sulfonyl.

In the above formula, R1 may be Br, Cl, F, —C$_6$H$_5$, —(C$_6$H$_4$)CF$_3$ or —(C$_6$H$_4$)O(C$_6$H$_5$). R2 may be methyl, Bn or Boc. R4, R5 or both R4 and R5 may be methyl. R7 may be methyl, Boc or a substituent of formula (ii), (iii), (iv) or (v) as defined above for the compound of formula (I).

In one embodiment, the invention relates to the use of a compound of formula (IIId), or a pharmaceutically acceptable salt, ester or prodrug thereof, for the manufacture of a medicament, e.g. a pharmaceutical composition, for the treatment and/or prevention of a parasitic infection:

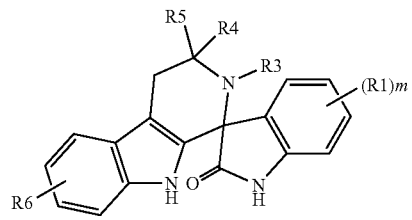

(IIId)

wherein
m is 1 or 2;
R1 is H, halogen, alkyl, haloalkyl, alkoxy or amine;
R3 is H or alkyl;
R4 is H or alkyl;
R5 is H or alkyl; and
R6 is H, halogen, haloalkyl or alkoxy.

In the above formula, R1 may be F, Cl, Br, methyl, —CF$_3$, —OCH$_3$ or —N(CH$_3$)$_2$ and R6 may be Cl, —CF; or —OCH$_3$. In some examples, R1 may be di-Cl when m is 2.

In one embodiment, the invention relates to the use of a compound of formula (IIIe), or a pharmaceutically acceptable salt, ester or prodrug thereof, for the manufacture of a medicament, e.g. a pharmaceutical composition, for the treatment and/or prevention of a parasitic infection:

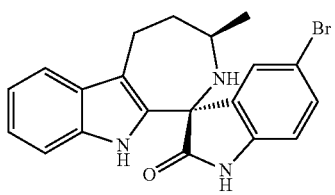

(IIIe)

In one embodiment, the invention relates to the use of a compound of formula (IIIf), or a pharmaceutically acceptable salt, ester or prodrug thereof, for the manufacture of a medicament, e.g. a pharmaceutical composition, for the treatment and/or prevention of a parasitic infection:

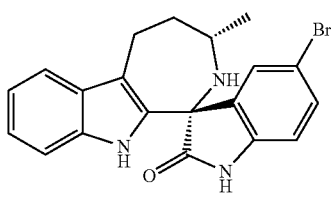

(IIIf)

In one embodiment, the invention relates to the use of a compound of formula (IIIg), or a pharmaceutically acceptable salt, ester or prodrug thereof, for the manufacture of a medicament, e.g. a pharmaceutical composition, for the treatment and/or prevention of a parasitic infection:

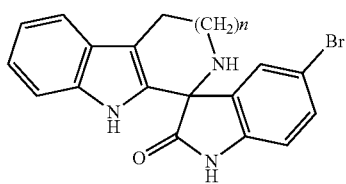

(IIIg)

wherein n is 1 or 2.

In another aspect, the invention provides a compound of formula (I), (II) or (III) or a compound of any of formulae (Ia) to (Ip) and (IIIa) to (IIIg) as defined above, or a pharmaceutically acceptable salt, ester or prodrug thereof, for use in the treatment and/or prevention of a disease caused by an infection by a parasite such as, for example, *Plasmodium falciparum, Plasmodium vivax, Plasmodium malariae, Plasmodium ovale, Trypanosoma cruzi* or a parasite of the *Leishmania* genus such as, for example, *Leishmania donovani*.

In still another aspect, the invention provides a method of treating and/or preventing a disease caused by a parasite such as *Plasmodium falciparum, Plasmodium vivax, Plasmodium malariae, Plasmodium ovale, Trypanosoma cruzi* or a parasite of the *Leishmania* genus such as, for example, *Leishmania donovani*, comprising administering to a subject in need thereof an effective amount of a compound of formula (I), (II) or (III) or a compound of any of formulae (Ia) to (Ip) and (IIIa) to (IIIg) as defined above, or a pharmaceutically acceptable salt, ester or prodrug thereof. The disease may be malaria, leishmaniasis or Chagas disease.

In another aspect the invention provides a combination of a compound of formula (I), (II) or (III) or a compound of any of formulae (Ia) to (Ip) and (IIIa) to (IIIg) as defined above, or a pharmaceutically acceptable salt, ester or prodrug thereof with at least one second drug substance. The second drug substance may be an antimalarial drug such as, for example, artesunate, artemether, di-hydro-artemisinin, mefloquine, chloroquine, sulfadoxine, pyrimethamine, piperaquine, pyronaridine, lumefantrine or atovaquone.

In another aspect the invention provides a pharmaceutical combination, e.g. a kit, comprising a) a first agent which is a compound of formula (I), (II) or (III) or a compound of any of formulae (Ia) to (Ip) and (IIIa) to (IIIg) as defined above, in free form or in pharmaceutically acceptable salt form, and b) at least one co-agent. The kit may comprise instructions for its administration.

In still another aspect, the invention provides a method for preparing a compound of formula (I), (II) or (III) or a compound of any of formulae (Ia) to (Ip) and (IIIa) to (IIIg) as defined above, comprising: reacting an amine with an isatin.

DETAILED DESCRIPTION

Definitions

The term "alkyl" as used herein with reference to alkyl group refers to branched or straight chain hydrocarbon groups, comprising preferably 1 to 15 carbon atoms, preferably alkyl is lower alkyl The term "lower alkyl" as used herein refers to branched or straight chain alkyl groups comprising 1 to 6 carbon atoms. Examples of alkyl groups include, but are not limited to, methyl, ethyl, n-propyl, i-propyl, n-butyl, i-butyl, sec-butyl, t-butyl, pentyl, hexyl, heptyl, nonyl, decyl, etc.

The term "cycloalkyl" refers to a saturated or partially saturated (non-aromatic) ring comprising preferably 3 to 8 carbon atoms. Examples include, but are not limited to, cyclopropyl, cyclopentyl, cyclohexyl and cycloheptyl.

Any alkyl group as defined above may be substituted with one or more substituents including, but not limited to, substituents such as halogen, lower alkyl, lower alkoxy, hydroxy, mercapto, amino, carboxy, cycloalkyl, aryl, heteroaryl, and the like. Examples of substituted alkyl groups include, but are not limited to, haloalkyl groups such as fluoromethyl, difluoromethyl, trifluoromethyl and pentafluoroethyl or other substituted alkyl groups such as hydroxymethyl, 1- or 2-hydroxyethyl, methoxymethyl, 1- or 2-ethoxyethyl, carboxymethyl, 1- or 2-carboxyethyl, and the like.

The term "aryl" as used herein refers to an aromatic ring having 6 to 18 carbon atoms and includes monocyclic groups as well as multicyclic (polycyclic) groups, e.g. fused groups such as bicyclic and tricyclic groups. Examples include, but are not limited to, phenyl group, naphthyl group and anthracenyl group. An aryl group may be unsubstituted or substituted at one or more ring positions with one or more substituents including, but not limited to, $C_{1-7}$ alkyl such as methyl, hydroxy, alkoxy, acyl, acyloxy, SCN, cyano, nitro, thioalkoxy, phenyl, heteroalkylaryl, alkylsulfonyl, halogen, acetamido, and formyl. Preferably aryl is phenyl. Preferably there are no substituents or one substituent.

The term "alkylaryl" as used herein refers to the group -aryl-R wherein R is an alkyl group as defined above, and aryl is as defined above. An example is —$(C_6H_4)CF_3$.

The term "arylalkyl" as used herein refers to the group -alkyl-R where R is an aryl group as defined above, and alkyl is as defined above. An example is benzyl.

The term "heterocyclo" or "heterocyclic" means a saturated or partially saturated (non-aromatic) ring having 5 to 18 atoms, including at least one heteroatom, such as, but not limited to, N, O and S, within the ring. The heterocyclic group may be unsubstituted or substituted with one or more substituents, including but not limited to, alkyl, halogen, alkoxy, hydroxyl, mercapto, carboxy, and phenyl. The heteroatom(s) as well as the carbon atoms of the group may be substituted. The heterocycle may optionally be fused or bridged with one or more benzene rings and/or to a further heterocyclic ring and/or to an alicyclic ring.

The term "heteroaryl" means an aromatic ring having 5 to 18 atoms, preferably 5 or 6 atoms, including at least one heteroatom, such as, but not limited to, N, O and S, within the ring. The term "heteroaryl" includes monocyclic groups as well as multicyclic groups, e.g. fused groups such as bicyclic and tricyclic groups. The heteroaryl group may be unsubstituted or substituted at one or more ring positions with one or more substituents including, but not limited to, alkyl, hydroxy, acyl, acyloxy, SCN, cyano, nitro, thioalkoxy, phenyl, heteroalkylaryl, alkylsulfonyl, halogen, and formyl. The heteroaryl may optionally be fused or bridged with one or more benzene rings and/or to a further heteroaryl ring and/or to an alicyclic ring.

Examples of heterocyclic and heteroaryl groups include, but are not limited to, morpholinyl, piperazinyl, piperidinyl, pyridyl, pyrrolidinyl, pyrazinyl, pyrimidinyl, purinyl, benzimidazolyl, benzoxazolyl, benzothiazolyl, benzofuranyl, benzofurazanyl, benzopyrazolyl, benzotriazolyl, benzothiophenyl, carbazolyl, carbolinyl, cinnolinyl, indolyl, isoindolyl indolinyl, imidazolyl, indolazinyl, indazolyl, morpholinyl, quinoxalinyl, quinolyl, isoquinolyl, quinazolinyl, 1,2,3,4-tetrahydroquinolinyl, tetrahydropyranyl, tetrazolopyridyl, thiadiazolyl, thienyl, azetidinyl, 1,4-dioxanyl, hexahydroazepinyl, pyridyl (e.g pyridine-2-only), thiomorpholinyl, dihydrobenzimidazolyl, dihydrobenzofuranyl, dihydrobenzothiophenyl, dihydrobenzoxazolyl, didhydrofuranyl, dihydroimidazolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazoll, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, thiazolyl, isothiazolyl, isoxazolyl, imidazolyl, indanyl, naphthpyridinyl, oxadiazolyl, oxazolyl, oxazoline, isoxazoline, oxetanyl, pyranyl, pyrazinyl, pyridopyridinyl, pyridazinyl, pyrrolyl, pyrazolyl, pyrrolyl, phenanthridinyl, triazolyl, thienyl, furanyl, isobenzofuranyl, or tetrazolyl, particularly N-containing heterocycles such as pyridyl, piperidinyl, pyrimidinyl, pyrrolidinyl, piperazinyl, quinazolinyl, 2,2,6,6-tetramethylpiperidyl and morpholinyl.

The term "arene" as used herein refers to a monocyclic or polycyclic aromatic hydrocarbon compound. Examples of arenes include, but are not limited to, benzene, naphthalene, toluene, xylene, styrene, ethylbenzene, cumene, and generally benzene rings with one or more aliphatic side chains or substituents.

The term "heteroarene" as used herein refers to a heterocyclic compound formally derived from an arene by replacement of one or more methine (—C=) and/or vinylene (—CH=CH—) groups by trivalent or divalent heteroatoms, respectively, in such a way as to maintain the continuous π-electron system characteristic of aromatic systems and a number of out-of-plane π-electrons corresponding to the Hückel rule (4n+2) (wherein n is an integer). Examples of heteroarenes include, but are not limited to, thiophene, furan pyridine and. preferably indole The term "alkoxy" as used herein refers to the group —OR wherein R is alkyl as defined above. The term "lower alkoxy" has a corresponding meaning to the term "lower alkyl" as defined above. Examples of lower alkoxy groups include, but are not limited to, methoxy, ethoxy, n-propoxy, i-propoxy, n-butoxy, i-butoxy, sec-butoxy and t-butoxy.

The term "carbonyl" as used herein refers to the group —C(=O)—.

The term "alkoxycarbonyl" as used herein refers to the group —COR wherein R is an alkoxy group as defined above. An example is Boc.

The term "arylcarbonyl" as used herein refers to the group —COR wherein R is an aryl group as defined above.

The term "sulfonyl" as used herein refers to the group —SO$_2$—.

The term "arylsulfonyl" as used herein refers to the group —SO$_2$R wherein R is an aryl group as defined above.

The term "hydroxyalkyl" as used herein refers to the group —ROH wherein R is an alkyl group as defined above.

The term "ether" as used herein refers to a group represented by the formula —ROR', wherein R and R' can be, independently, an alkyl, aryl, heteroaryl, cycloalkyl or heterocycloalkyl group as defined above.

The term "amino" as used herein refers to a group of formula —NRR1, wherein each of R and R1 is independently an alkyl group as defined above ot hydrogen.

The term "halo" or "halogen" as used herein refers to F, Cl, Br or I.

The term "ester" as used herein refers to the group —COOR wherein R is an alkyl or aryl group as defined above.

The term "spiro" as used herein refers to a cyclo group attached to another ring via one carbon atom common to both rings.

The term "substituted" is intended to describe moieties having substituents replacing a hydrogen atom on one or more atoms, e.g. C, O or N, of a molecule; conveniently one or two atoms are replaced.

Any hydrocarbon chain which is not otherwise discussed herein conveniently contains one or two carbon atoms when non-cyclic and 6 carbon atoms when cyclic The term "alkylene" is typically of 2 carbon atoms.

The term "prodrug" as used herein means a pharmacologically acceptable derivative of the compound of formula (I), (II), (III) or (IV) as defined above, such that an in vivo biotransformation of the derivative gives the compound as defined in formula (I), (II), (III) or (IV). Prodrugs of compounds of formula (I), (II), (III) and (IV) may be prepared by modifying functional groups present in the compounds, such as hydroxy or acid groups, in such a way that the modified groups are cleaved in vivo to give the parent compound. Suitable prodrugs include, for example, esters or amides.

The term "salts" includes therapeutically active non-toxic acid addition salts derived from the compounds of formula (I), (II), (III) and (IV). Acid addition salts can be obtained by treating the base form of the compounds with appropriate acids. The compounds of the invention containing acidic protons may also be converted into their therapeutically active non-toxic base addition salt forms by treatment with appropriate organic and inorganic bases. Conveniently, the acid or base addition salt forms can be converted into the free forms by treatment with an appropriate base or acid.

The term "addition salt" as used in the present context also comprises the solvates which the compounds of the invention, as well as the salts thereof, are able to form. Such solvates include, for example, lithium, sodium, succinate, malonate, nitrate, ammonium, phosphate, formate, carbonate, malate, hydrochloride, hydrobromide, hydroiodide, maleate, fumarate, methanesulfonate, acetate, sulfate, tartrate, citrate, paratoluenesulfonate, and trifluoroacetate.

The term "protecting group" means a group that masks a functional group in a molecule, so that chemoselectivity is possible during a reaction. Suitable protecting groups are preferably simple to incorporate, stable to the relevant reaction conditions and easy to remove. Such protecting groups are known to those skilled in the art and are described in Protective Groups in Organic Synthesis by Theodora W Greene (John Wiley & Sons Canada, Ltd). Suitable protecting groups include, for example, Aloc, benzoyl, benzyl, Boc, Cbz, TBS, TPDMS, Fmoc, PMB, phthalimdes, tosyl and Troc.

The term "treat", "treating", "treated" or "treatment" includes the prevention, diminishment or alleviation of at least one symptom associated with or caused by the state, disease or disorder being treated.

The term "prevent", "preventing" or "prevention" includes the prevention of at least one symptom associated with or caused by the state, disease or disorder being prevented.

The term "patient" includes organisms that are capable of suffering from, or afflicted or infected with, a parasitic disease, e.g. mammals such as humans, cows, horses, pigs, sheep, cats, dogs, goats, mice, rabbits, rats and transgenic non-human animals, in some embodiments the patient is a human, e.g. a human capable of suffering from, or afflicted with, malaria.

A "parasitic disease" includes disorders and states that are associated with a parasitic infection in a subject.

The term "effective amount" of a compound of the invention is the amount necessary or sufficient to treat or prevent a disease caused by a parasite such as *Plasmodium falciparum*, *Plasmodium vivax*, *Plasmodium malariae*, *Plasmodium ovule*, *Trypanosoma cruzi* or a parasite of the *Leishmania* genus such as, for example, *Leishmania donovani*. The effective amount can vary depending on the compound employed, the mode of administration, the treatment desired and the disease indicated, as well as other factors such as a patient's age, body weight, general health and sex. One of ordinary skill in the art would be able to study the factors described herein and make a determination regarding the effective amount of a compound of the invention without undue experimentation.

The term "pharmaceutical composition" includes preparations, e.g. medicaments, suitable for administration to mammals, e.g. humans.

Compounds provided by the invention are hereinafter designated as "compound(s) of the invention". A compound of the invention includes a compound in any form, e.g. in free form, in the form of a salt, in the form of a solvate and in the form of a salt and a solvate. The compounds of the invention embrace the compounds of formulae I, II and III including a pharmaceutically acceptable salt, ester or prodrug thereof.

It will be appreciated that any sub-genus of one substituents may be combined with another genus or sub-genus of another substituent or substituents.

It will be appreciated that the compounds of the invention may exist in the form of optical isomers, racemates or diastereoisomers. The scope of this invention embraces all stereochemically isomeric forms of the compounds. The term "stereochemically isomeric forms" as used herein therefore means all possible isomeric forms which the compounds of the invention may possess. Unless otherwise mentioned or indicated, the chemical structures, systematic names and formulae of the compounds denote the mixture of all possible stereochemically isomeric forms, containing all diastereomers and enantiomers of the basic molecular structure. In particular, stereogenic centers may have the R- or S-configuration.

It will also be appreciated that the compounds of the invention can exist as tautomers, for example as keto-enol tautomeric forms. The scope of this invention embraces all such tautomeric forms.

The compounds of the invention are useful in the treatment and prevention of infections by a pathogen, as indicated in standard in vitro and in vivo tests, eg as described hereinafter. The pathogen may be a parasite, in particular, a *Plasmodium* parasite, a *Leishmania* parasite or a *Trypanosoma* parasite. More particularly, the pathogen may be *Plasmodium falciparum*, *Plasmodium vivax*, *Plasmodium malariae*, *Plasmodium ovate*, *Trypanosoma cruzi* or a parasite of the *Leishmania* genus such as, for example, *Leishmania donovani*.

The compounds of the invention and particularly as exemplified, in free or pharmaceutically acceptable salt form, exhibit valuable pharmacological properties, e.g. as antiparasitic agents, for example, as indicated by the tests of the Examples A and B hereinafter and are therefore indicated for therapy.

The compounds of the invention exhibit an $IC_{50}$ against *Plasmodium falciparum* ranging from about 0.1 nM to about 5000 nM eg less than about 100 nM to greater than about 5000 nM, in particular less than about 500 nM, more particularly less than about 100 nM, still more particularly less than about 50 nM, and most particularly less than about 20 nM. Typically the compounds of the invention have activities more than 5 nM, or 0.5 nM.

The required dosage for pharmaceutical use may vary inter alia depending on the mode of administration, the particular condition to be treated, the effect desired, the compound employed, patient's age, body weight, etc In general, satisfactory results are indicated to be obtained systemically at daily dosages of from about 0.1 mg/kg to about 300 mg/kg per body weight, eg 0.01 to about 10 such as 1 to 10 mg/kg.

An indicated daily dosage in the larger mammal, e.g. humans, is in the range from about 1 mg to about 10,000 mg, e.g. 10 to 700 mg conveniently administered, for example, in divided doses up to six times a day or in retard form. Suitable unit dosage forms for oral administration comprise from ca. 10 mg to 1000 mg active ingredient. Based on the tests described hereinafter, a typical daily dose for compounds in Example 50 and 62 (compounds 37 and 51) for humans is about 4 mg/kg, eg about 300 mg.

The compounds of the invention may be administered in free form or in pharmaceutically acceptable salt form Preferred compounds are examples 50 and 62 which have the S-configuration at C3' (the spiro indole carbon). A group of compounds comprises those which have the same configuration at the spiro carbon atom eg C3'.

A further group of compounds wherein R4 is different to R5. An additional group of compounds have the same configuration at C1,2' (to which R4 and R5 are bound) as the configuration of example 48 at C1,2'

The compounds of the invention may be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form.

Depending on the mode of administration, the pharmaceutical composition may comprise from 0.05 to 99% by weight, more particularly from 0.1 to 70% by weight, even more particularly from 30 to 70% by weight of the active ingredient, and from 1 to 99.95% by weight, more particularly from 30 to 99.9% by weight, even more particularly from 30 to 70% by weight of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant or preservative.

Pharmaceutical compositions comprising a compound of the invention in free form or in pharmaceutically acceptable salt form in association with at least one pharmaceutical acceptable carrier or diluent can be manufactured in conventional manner by mixing with a pharmaceutically acceptable carrier or diluent and exhibit the same order of activity as the free compounds.

The compounds of the invention may be administered alone or in combination with a second drug substance. To achieve higher efficacy and prevent the development of drug resistance, the compounds of the invention may be combined with the following non-exhaustive list of known and marketed antimalarial drugs: artesunate, artemether, di-hydroartemisinin, mefloquine, chloroquine, sulfadoxine, pyrimethamine, piperaquine, pyronaridine, lumefantrine or atovaquone.

Combinations include fixed combinations, in which a compound of the invention and at least one second drug substance are in the same formulation; kits, in which a compound of the invention and at least one second drug substance in separate formulations are provided in the same package, e.g. with instructions for co-administration; and free combinations in which a compound of the invention and at least one second drug substance are packaged separately, but instructions for concomitant or sequential administration are given.

Treatment with combinations according to the invention may provide improvements compared with single treatment.

A combination of a compound of the invention and a second drug substance as a combination partner may be administered by any conventional route, for example as set out herein for a compound of the invention. A second drug may be administered in dosages as appropriate, e.g. in dosage ranges which are similar to those used for single treatment, or, e.g. in case of synergy, below conventional dosage ranges.

Pharmaceutical compositions comprising a combination of the invention and pharmaceutical compositions comprising a second drug as described herein, may be provided as appropriate, e.g. according, e.g. analogously, to a method as conventional, or as described herein for a pharmaceutical composition of the invention.

The invention also provides a method for the preparation of a spiro oxindole compound, the method including reacting an amine with an isatin.

In one embodiment, the method comprises reacting an indolylalkylamine with a heterocyclic compound having a carbonyl group to form a spiro compound with an amine functional group; protecting the amine functional group on the spiro compound with a protecting group to form an amine-protected spiro compound; and removing the protecting group from the spiro compound.

Through use of the protecting group, the overall yield of the synthesis may be increased and the purification process may be simplified (e.g. 99% of compound 1 is obtainable with the method provided by the invention using only flash column chromatography). The overall process is efficacious and amenable to large scale synthesis.

Spirocyclization may be effected in the presence of a catalyst such as, for example, pTsOH, Six-, seven-, or eight member rings with or without substituent analogues may be made by adjusting the quantity of catalyst used. Further, the presence of the catalyst (e.g. about 0.1 to 0.2 equivalent of pTsOH) accelerates the reaction and lowers the reaction temperature to, for example, about 100° C.

It will be appreciated that the compounds of the invention may exist in the form of optical isomer, racemates or diastereoisomers. The scope of this invention embraces all stereochemically isomeric forms of the compounds. The term "stereogenic" forms as used herein therefore means all possible isomeric forms which the compounds of the invention may possess. In particular, asymmetric carbons may have the R- or S-configuration. For example, the asymmetric spiro carbon of the compounds of the invention may have the R- or S-configuration. Pure enantiomeric compounds may be obtained by eg obtention of the enantiomers from the racemates in conventional manner by chiral separation, from chiral intermediates, or enzymatic resolution.

It will also be appreciated that the compounds of the invention can exist as tautomers. For example, compounds of the invention where R1 is OH or $NH_2$ or where R2 is $NH_2$ may exist as tautomeric forms. The scope of this invention embraces all such tautomeric forms.

In a group of compounds, the compounds comprise the following a) compounds of the invention wherein the stereochemistry of the spiro carbon atom (with regard to the 4 bonds) is the same as that of Example 50 hereinafter. In a sub-group one of R4 and R5 is a substituent and the other is hydrogen and the stereochemistry of the carbon atom to which R4 and R5 are attached is the same as that of the Example 50 title compound hereinafter.

b) compounds of the invention wherein the stereochemistry of the spiro carbon atom is the opposite as that of Example 50 hereinafter. In a sub-group one of R4 and R5 is a substitutent and the other is hydrogen and the stereochemistry of the carbon atom to which R4 and R5 are attached is the same as that of the Example 50 title compound hereinafter.

c) compounds of the invention wherein the substituents on spiro carbon atom may have any configuration. Conveniently the compounds of formula 1 may have any configuration of the carbon atom to which R4 and R5 are attached.

A group of compounds comprises the title compounds of at least one of the example title compounds. In a sub-group the compounds are racemic. In a second subgroup the compounds have the same stereo-configuration at the spiro carbon in Example 50. In a third subgroup the compounds have the opposite stereo-configuration at the spiro carbon in Example 50.

Abbreviations
AcHN=acetamido
AcOH=acetic acid
Aloc=allyloxycarbonyl
Bn=benzyl
BOC, Boc, t-BOC=tert-butoxycarbonyl
$(Boc)_2O$=di-tert-butyl dicarbonate
Cbz=benzyloxycarbonyl
$ClCO_2Et$=ethyl chloroformate
DCM=dichloromethane
DMAP=dimethylaminopyridine
DMF=dimethylformamide
DMSO=dimethylsulfoxide
di-Cl=dichloro
EDG=electron donating group
Et=ethyl
$Et_3N$=triethylamine
EtOAc=ethyl acetate
EtOH=ethanol
Fmoc=9-fluorenylmethoxycarbonyl
iPr=isopropyl
LC-MS=liquid chromatography-mass spectrometry
Me=methyl MeO=methoxy
MeOH=methanol
NaH=sodium hydride (60% paraffin)
NH₄OAc=ammonium acetate
Ni(R)=Raney nickel
NMe₂=dimethylamino
OPh=phenoxy
OTs=tosylate
PMB=p-methoxybenzyl
Pr=propyl
pTsCl=p-toluenesulfonyl chloride
pTsOH=p-toluenesulfonic acid
rt=room temperature
TBS=t-butyldimethylsilyl
THF=tetrahydrofuran
TPDMS=t-butyldiphenylsilyl
Troc=2,2,2-trichloroethoxycarbonyl I—General Synthetic Methods Compounds of the invention can be made by the methods depicted in the reaction schemes shown below. The starting materials and reagents used in preparing these compounds are either available commercially or are prepared by methods known to those skilled in the art. These schemes are merely illustrative of some of the methods by which the compounds of this invention can be synthesized, and various modifications to these schemes can be made and will be suggested to one skilled in the art having referred to this disclosure.

SCHEME A: Preparation of 3-(1H-Indol-3-yl)-1-methyl-propylamine

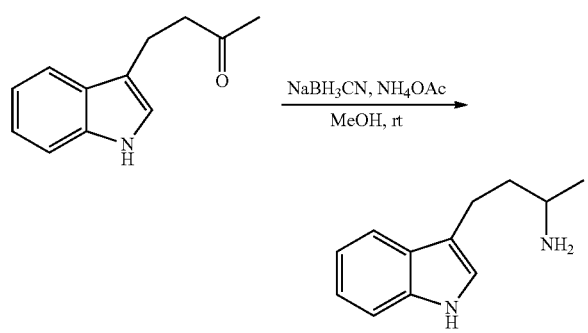

To a solution of 4-(1H-indol-3-yl)-butan-2-one (1.0 g, 5.3 mmol) in methanol (20 mL is added ammonium acetate (4.45 g, 57.73 mmol) and sodium cyanoborohydride (0.37 g, 5.9 mmol) at room temperature. The resulting mixture is allowed to stir for 64 hours at the same temperature. The reaction mixture is quenched by addition of 1 N hydrochloric acid and adjusted to pH ~2. The mixture is concentrated and extracted with dichloromethane (50 mL). Then the aqueous phase is adjusted to pH ~12 using 4 N aqueous sodium hydroxide and extracted with dichloromethane (3×50 mL). The combined organic phases are dried with sodium sulfate and concentrated in vacuo. The resulting residue is subjected to flash column chromatography (5%-30% methanol in dichloromethane) to afford 3-(1H-indol-3-yl)-1-methyl-propylamine (622 mg, 62%) as an oil.

SCHEME B: Preparation of 3-(1H-Indol-3-yl)-propylamine

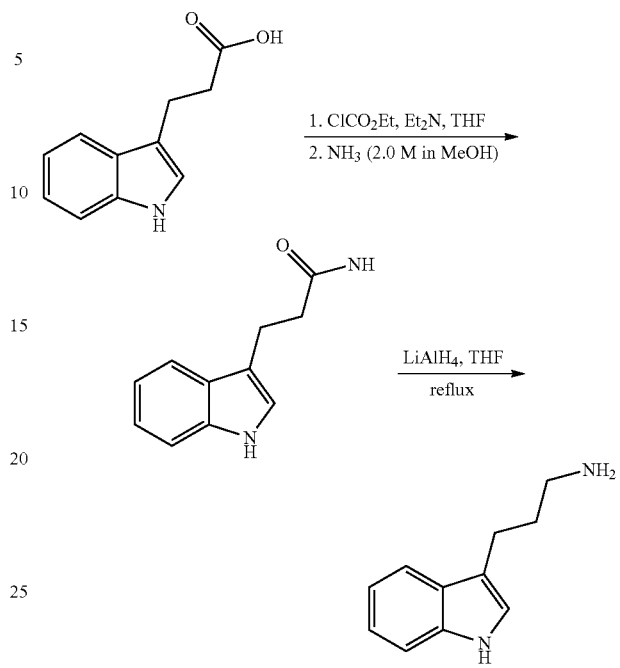

Step 1: To a solution of 3-(1H-indol-3-yl)propanoic acid (6.06 g, 32.0 mmol) in tetrahydrofuran (100 mL) is added triethylamine (18 mL, 129 mmol) and ethyl chloroformate (4.65 mL, 48.8 mmol) in an ice cooled bath. The resulting mixture is allowed to stir for 0.5 hours at the same temperature followed by the addition of ammonia (2 N in methanol, 90 mL, 180 mmol). After stirring for a further one hour, the resulting precipitate is filtered off and the filtrate is concentrated in vacuo. The residue, after diluted with water (100 mL), is extracted with ethyl acetate (3×100 mL). The combined organic phases are washed with brine, dried with sodium sulfate and concentrated in vacuo to obtain 3-(1H-indol-3-yl)propylamide (3.85 g, 65%).

Step 2: To the solution of 3-(1H-indol-3-yl)propylamide (1.85 g, 9.83 mmol) in tetrahydrofuran (50 mL) is added lithium aluminum hydride (1.49 g, 39.31 mmol) at 0° C. The resulting mixture is warmed to room temperature and then refluxed for 2.5 hours. The mixture is then cooled to room temperature and quenched by slow addition of water (2 mL) followed by aqueous 15% sodium hydroxide (2 mL) and water (2 mL). The mixture is allowed to stir overnight and filtered through celite. The filtrate obtained is evaporated and the residue is subjected to flash column chromatography (50% dichloromethane: 40% methanol: 10% aqueous ammonia (40%)) to afford 3-(1H-Indol-3-yl)propylamine (1.61 g, 94%).

SCHEME C: Preparation of 5'-Bromo-3-methyl-3,4,5,10-tetrahydro-2H-spiro[azepino[3,4-b]indole-1,3'-indol]-2'(1'H)-one (1)

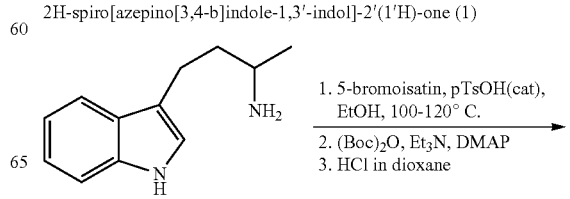

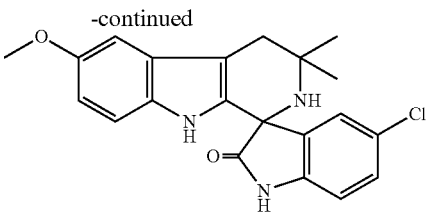

Step 1: To a solution of 3-(1H-indol-3-yl)-1-methyl-propylamine (1.84 g, 4.65 mmol) in 20 mL of ethanol is added 5-bromoisatin (660 mg, 2.92 mmol) and p-toluenesulfonic acid (101 mg, 0.531 mmol) at room temperature. The reaction vial is sealed and the reaction mixture is heated to 100° C. After stirring for 16 hours, the reaction mixture is cooled to room temperature and concentrated to dryness. The residue is subjected to flash column chromatography (0%-30% EtOAc in hexanes) to afford the impure 1 as dark brown solid (2.74 g).

Step 2: To a solution of the above product (2.74 g, 6.91 mmol) in 13 mL of dry dichloromethane is added triethylamine (2.87 mL, 20.73 mmol), followed by di-tert-butyl dicarbonate (9.05 g, 41.46 mmol) and 4-dimethylaminopyridine (2.53 g, 20.7 mmol) at room temperature. The resulting mixture is stirred for 16 hours at the same temperature and then concentrated to dryness. The residue is subjected to flash column chromatography (0%-4% EtOAc in hexanes) to afford 2.22 g of compound 12.

Step 3: To a solution of obtained compound 12 (2.2 g, 3.72 mmol) in anhydrous dichloromethane (10 mL) is added 4 N HCl in 1,4-dioxane (15 mL). The resulting mixture is stirred for 48 hours, during which time another batch of 4 N HCl in dioxane is added to ensure the reaction is completed. After the reaction, monitored by LCMS, is completed, the reaction mixture is adjusted to pH ~10 using aqueous 1 N NaOH. The mixture is concentrated in vacuo and the remaining aqueous phase is extracted with EtOAc (3×100 mL). The combined organic phases are dried (Na₂SO₄) and concentrated in vacuo. The residue is subjected to flash column chromatography to afford compound 1 (1.28 g, 37% over 3 steps) along with a trace amount of compound 13 (30 mg).

SCHEME D: Preparation of 5'-Chloro-3,3-dimethyl-6-methoxy-2,4,9-trihydrospiro-[β-carboline-1,3'-indol-2'(1'H)-one (31)

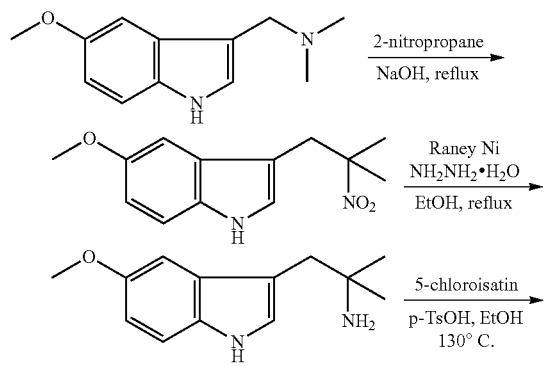

Step 1: A mixture of 5-methoxygramine (3.0 g, 14.7 mmol), 2-nitropropane (9.36 mL, 104 mmol) and NaOH pellets (0.617 g, 15.4 mmol) is stirred and heated at reflux for 18 hours. After the mixture is cooled to room temperature, 12.85 mL of 10% acetic acid is added and stirring is continued for one hour. The mixture is partitioned between diethyl ether (40 mL) and water (40 mL) and the organic layer is separated, washed with water (3×30 mL), dried over MgSO₄ and concentrated in vacuo. The residue is subjected to flash chromatography column to give a nitro intermediate (3.12 g, 86%).

Step 2: To a solution of the nitro intermediate (3.12 g, 12.6 mmol) in 40 mL of 95% EtOH is added, with stirring, 2.0 g of Raney nickel. The mixture is heated to 80° C. and then stopped. A solution of 98% hydrazine hydrate (2.8 mL, 0.0377 mol) in 3.3 mL EtOH is added at a rate sufficient to maintain reflux throughout the addition. Heat is reapplied to continue reflux overnight. The mixture is filtered and the filtrate concentrated in vacuo. The residue was precipitated from dilute aqueous HCl solution with 4 N NaOH, extracted dichloromethane, and recrystallized from isopropanol to give amine (1.92 g, 70% yield).

Step 3: To a mixture of the above amine (1.2 g, 5.5 mmol) and 5-chloroisatin (1.10 g, 6.05 mmol) in 20 mL of ethanol was added p-toluenesulfonic acid (0.209 g, 5.5 mmol). The reaction vial was sealed and heated to 130° C., for 16 hours. The target compound precipitated upon cooling. The solids are filtered and washed several times with (ice) cold ethanol to yield compound 31 (1.29 g, 62%).

SCHEME E: Preparation of 7-chloroisatin

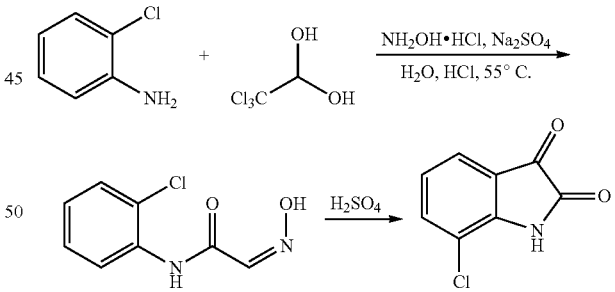

To a mixture of 2-chlor aniline (1.02 g, 7.84 mmol), anhydrous sodium sulfate (8.94 g, 62.71 mmol), hydroxylamine hydrochloride (2.24 g, 31.35 mmol) and 1M hydrochloric acid (8.0 mL) in water (60 mL) is added chloral hydrate (1.58 g, 9.41 mmol) at room temperature. The resulting mixture is warmed to 55° C. and stirred for 6 hours. While the mixture is cooling to room temperature, solid precipitate is formed and collected by filtration, washed with water and dried under vacuum to yield the hydroxyliminoacetanilide intermediate, which is added in small portions to concentrated sulfuric acid (5.0 mL) that is preheated to 55° C. The temperature of the reaction mixture is maintained at below 58° C. throughout the addition. After the addition is completed, the dark-colored mixture is heated to 80° C. for 10 minutes before cooling down to room temperature. The mixture is then poured into crushed ice, swirled, and left to stand for 30 minutes. The precipitate formed is collected by filtration, washed with water and dried under vacuum to yield 7-chloroisatin as a reddish brown powder.

SCHEME F: Preparation of (1R,3S)-5'-Chloro-3-methyl-2,3,4,9-tetrahydrospiro[β-carboline-1,3'-indol-2'(1'H)-one (33)

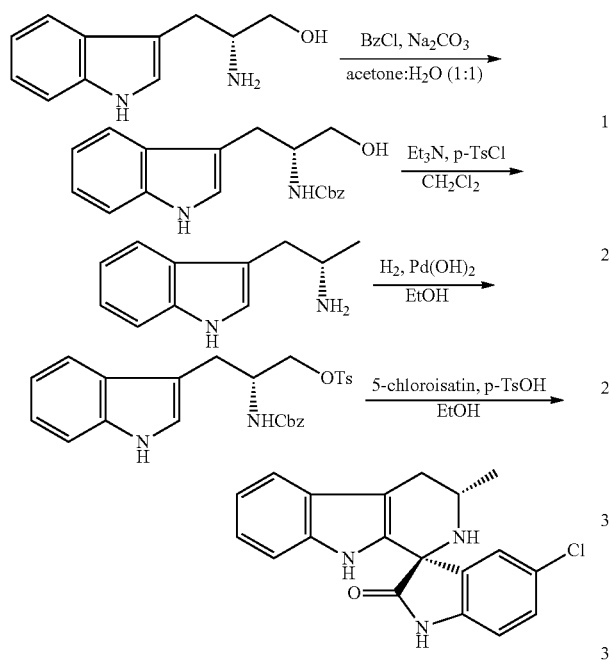

Step 1: To a mixture of D-tryptophanol (500 mg, 2.27 mmol 11.3 mL ater and 11.3 mL acetone is added sodium carbonate (482 mg, 3.92 mmol) in an ice cooled bath, followed by dropwise addition of benzyl chloroformate (0.374 mL, 2.29 mmol). After the addition, the cooling bath is removed and the reaction is stirred at room temperature for 2 hours. The reaction mixture is acidified to pH 2 with concentrated HCl and diluted with water (40 mL). The aqueous layer is extracted with EtOAc (2×60 mL). The combined organics are then dried with magnesium sulfate, filtered and concentrated in vacuo. The residue is subjected to flash chromatography column to give a Cbz protected intermediate (428 mg, 50%).

Step 2: A solution of the Cbz-protected intermediate (320 mg, 0.988 mmol) and triethylamine (267 µL, 1.93 mmol) in thy dichloromethane (2.78 mL) is cooled to 0° C. p-Toluenesulfonyl chloride (199.6 mg, 1.05 mmol) is added and the solution is stirred at room temperature for 18 hours. The reaction mixture is concentrated in vacuo. The residue is subjected to flash chromatography column to give the corresponding tosylate (580 mg, 100%).

Step 3: The tosylate intermediate (580 mg, 1.21 mmol) is dissolved in 36 mL absolute ethanol and 72.7 mg palladium (II) hydroxide catalyst is added. The reaction mixture is stirred under 1 atm H$_2$ atmosphere at room temperature for 2 hours. The reaction mixture is filtered through celite and the filtration is concentrated in vacuo. The residue is dissolved in EtOAc (50 mL), washed with sat aq NaHCO$_3$ (50 mL, dried with magnesium sulfate, filtered and concentrated in vacuo to yield the S-amine (169 mg, 80%).

Step 4: To a stirring solution of the S-indoleamine (153 mg, 0.881 mmol) in 3.1 mL dry ethanol is added 5-chloroisatin (176 mg, 0.969 mmol) and p-toluenesulfonic acid (16.8 mg, 0.088 mmol). The solution is stirred at 110° C. for 16 hours in a sealed tube. The reaction mixture is concentrated in vacuo. The residue is subjected to flash chromatography column and further purified by precipitation using petroleum ether to give compound 33 (135 mg, 45%).

SCHEME G: Preparation of (1R,3S)-5',7-dichloro-6-fluoro-3-methyl-2,3,4,9-tetrahydrospiro[β-carboline-1,3'-indol-2'(1'H)-one (35) and (1R,3S)-5'-chloro-6-fluoro-3-methyl-2,3,4,9-tetrahydrospiro[β-carboline-1,3'-indol-2'(1'H)-one (36)

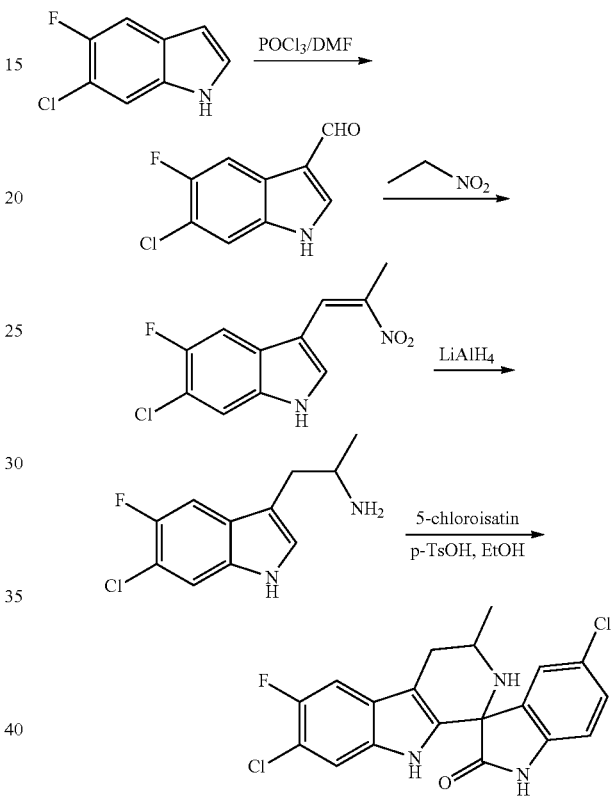

Step 1: POCl$_3$ (2.43 mL, 26.53 mmol) was added dropwise to N,N-dimethylformamide (15.0 mL) at −20° C. and stirred below −5° C. for one hour. A solution of 6-chloro-5-fluoroindole (3.0 g, 17.69 mmol) in dimethylformamide (5.0 mL) was added dropwise to the above reaction mixture at −20° C. The salt-ice bath was removed and the reaction mixture was warmed to 35° C. After one hour, the reaction was poured onto ice and basified by solid sodium bicarbonate and extracted with ethyl acetate. The combined organic layer was washed with water and then concentrated to give 6-chloro-5-fluoro-1H-indole-3-carbaldehyde (3.4 g, 97%) as a light brown solid. $^1$H NMR (500 MHz, CDCl$_3$): δ 10.02 (s, 1 H), 8.10 (d, 1H, J=9.5 Hz), 7.87 (s, 1 H), 7.49 (d, 1H, J=5.5 Hz).

Step 2: The solution (0.2 M) of 6-chloro-5-fluoro-1H-indole-3-carbaldehyde (4.0 g, 20.24 mmol) in nitroethane (100 mL) was refluxed with ammonium acetate (1.32 g, 0.85 mmol) for 4 hours. The reaction mixture was concentrated under vacuum to remove nitroethane, diluted with ethylacetate and washed with brine. The organic layer was concentrated to give 6-chloro-5-fluoro-3-(2-nitro-propenyl)-1H-indole (5.0 g, 97%) as a reddish orange solid. $^1$H NMR (500 MHz, CDCl$_3$): δ 8.77 (s, 1H), 8.32 (s, 1H), 7.58 (d, 1H, J=2.5 Hz), 7.54 (d, 1H, J=9 Hz), 7.50 (d, 1H, J=5.9 Hz), 2.52 (s, 3H).

Step 3: A solution of 6-chloro-5-fluoro-3-(2-nitro-propenyl)-1H-indole (5.0 g, 19.63 mmol) in tetrahydrofuran (10 mL) was added to the suspension of lithium aluminium hydride (2.92 g, 78.54 mmol) in tetrahydrofuran (20 mL) at 0° C. and then refluxed for 3 hours. The reaction mixture was cooled to 0° C., and quenched according to the Fischer method. The reaction mixture was filtered through celite and the filtrate concentrated to give 2-(6-chloro-5-fluoro-1H-indol-3-yl-1-methyl-ethylamine (4.7 g crude) as a viscous brown liquid. The residue was used without further purification. $^1$H NMR (500 MHz, CDCl$_3$): δ 8.13 (s, 1H), 7.37 (d, 1H, 6 Hz), 7.32 (d, 1H, J=10 Hz), 7.08 (s, 1H), 3.23-3.26 (m, 1H), 2.77-2.81 (m, 1H), 2.58-2.63 (m, 1H), 1.15 (d, 3H, J=6.5 Hz).

Step 4: A mixture of 2-(6-chloro-5-fluoro-1H-indol-3-yl-1-methyl-ethylamine (4.7 g, 20.73 mmol), 5-chloroisatin (3.76 g, 20.73 mmol) and p-toluenesulphonic acid (394 mg, 2.07 mmol) in ethanol (75 mL) was refluxed overnight. The reaction mixture was concentrated to remove ethanol, diluted with ethyl acetate and washed with saturated aqueous NaHCO$_3$. The organic layer was concentrated to give a brown residue, which was purified by silica gel chromatography (20% ethyl acetate in hexane) to provide the corresponding racemate (4.5 g, 56%) as a light yellow solid. The racemate was separated into its enantiomers by chiral chromatography to provide 35.

Compound 36 can be obtained in a similar fashion from 5-fluoroindole.

Alternatively 35 and 36 were be prepared in enantiomerically pure form by the following scheme.

SCHEME H: Alternative preparation of (1R,3S)-5',7-dichloro-6-fluoro-3-methyl-2,3,4,9-tetrahydrospiro[β-carboline-1,3'-indol-2'(1'H)-one (35)

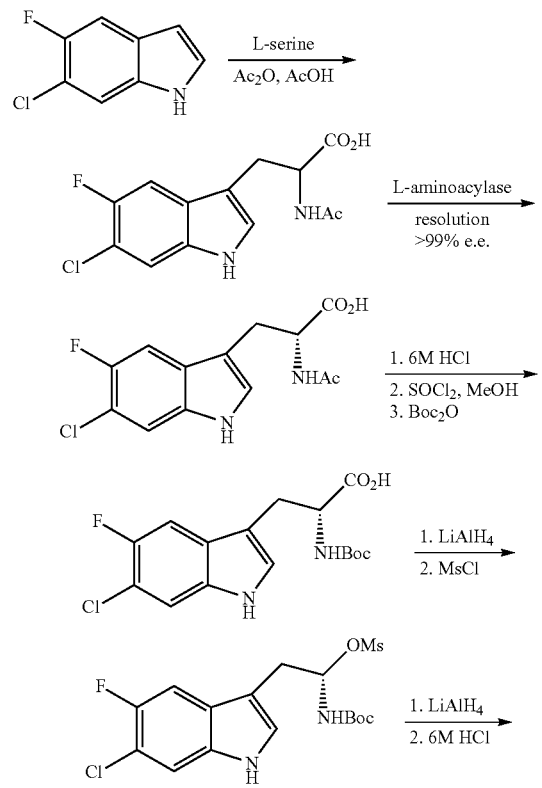

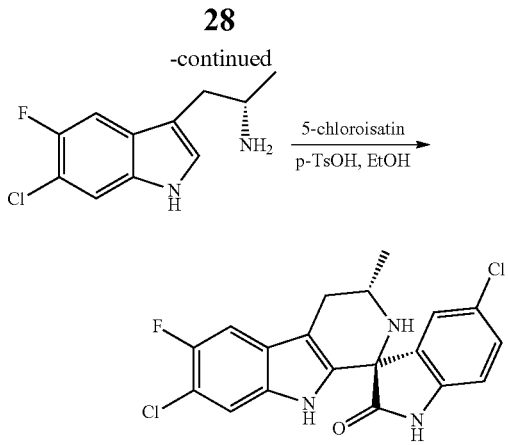

Step 1: To a solution of 6-chloro-5-fluoroindole (1.8 g, 10.8 mmol) and Ac$_2$O (10 mL) in AcOH (30 mL) was added L-serine (2.2 g, 20.9 mmol), the mixture was heated to 80° C. After TLC indicated the reaction was complete, the mixture was cooled to 0° C.; neutralized to pH 11, and washed with MTBE. The aqueous phase was acidified to pH 2 and extracted with EtOAc. The combined organic layers were washed with water and brine, dried with Na$_2$SO$_4$, filtered, and concentrated. The residue was purified with chromatography (Petroleum ether/EtOAc 1:1) to give 2-acetylamino-3-(6-chloro-5-fluoro-1H-indol-3-yl)-proprionic acid as a light yellow solid (1.2 g, 37% yield).

Step 2: 2-Acetylamino-3-(6-chloro-5-fluoro-1H-indol-3-yl)-proprionic acid (2.5 g, 8.4 mmol) was dissolved in aqueous NaOH (1N, 10 mL) and water added (70 mL). The mixture was heated to 37~38° C. and neutralized with HCl (1N) to pH 7.3-7.8. L-Aminoacylase (0.5 g) was added to the mixture and allowed to stir for 2 days, maintaining 37-38° C. and pH 7.3-7.8. The mixture was heated to 60° C. for another hour, concentrated to remove part of water, cooled and filtered. The filtrate was adjusted to pH 5.89 and filtered again. The filtrate was adjusted to pH 2.0 and extracted with EtOAc. The combined organic layer was dried over Na$_2$SO$_4$, filtered, concentrated and the residue was purified with chromatography (petroleum ether/EtOAc 1:1EtOAc) to give R-2-acetylamino-3-(6-chloro-5-fluoro-1H-indol-3-yl)-proprionic acid as a light yellow solid (1.2 g, 48% yield).

Step 3: R-2-acetylamino-3-(6-chloro-5-fluoro-1H-indol-3-yl)-proprionic acid (1.2 g, 4.0 mmol) was dissolved in HCl (6N, 10 mL) and the mixture heated to reflux for 4 hours, and then concentrated to dryness. Toluene (50 mL) was added to the residue and concentrated to dryness to remove water and HCl. The residue was dried under vacuum and then dissolved in MeOH (20 mL). To the solution was added dropwise SOCl$_2$ (0.5 mL, 6.8 mmol) at 0° C., and the mixture was stirred overnight. After removal of solvent, the residue was dissolved in THF/water (40/10 mL) and NaHCO$_3$ (1.0 g, 11.9 mmol) was added portionwise. Upon basification, Boc$_2$O (1.2 g, 5.5 mmol) added at 0° C. and allowed to stir at room temperature. After TLC indicated the reaction was finished, EtOAc was added and separated and the aqueous layer was extracted with EtOAc. The combined organic layers were washed with water and brine, dried with Na$_2$SO$_4$, filtered, concentrated and the residue was purified with chromatography (petroleum ether/EtOAc: 5/1) to give R-2-tert-butoxycarbonylamino-3-(6-chloro-5-fluoro-1H-indol-3-yl)-proprionic acid methyl ester 460 g, 31% yield for 3 steps).

Step 4: To a solution of R-2-tert-butoxycarbonylamino-3-(6-chloro-5-fluoro-1H-indol-3-yl)-proprionic acid methyl ester (460 mg, 1.2 mmol) in dry ether (20 mL) was added portionwise LiAlH$_4$ (92 mg, 2.4 mmol) at 0° C. The mixture was heated to reflux for 2 hours. After TLC indicated the reaction was finished, the mixture was cooled and carefully quenched with Na$_2$SO$_4$. The mixture was filtered and the filtrate was washed with saturated aqueous NH$_4$Cl and water, dried with Na$_2$SO$_4$, filtered, concentrated to give a crude product (400 mg), which was used without further purification.

Step 5: To a solution of the crude product (400 mg, 1.2 mmol) and Et$_3$N (0.3 mL, 2.2 mmol) in CH$_2$Cl$_2$ (5 mL) was added MsCl (160 mg, 1.4 mmol) dropwise at 0° C. The mixture was stirred for 2 hours at room temperature. After TLC indicated the reaction was completed, the mixture was washed with water and brine, dried with Na$_2$SO$_4$, filtered, concentrated and the residue was purified with chromatography (petroleum ether/EtOAc 5:1) to give methansulfonic acid (R)-2-tert-butoxycarbonylamino-3-(6-chloro-5-fluoro-1H-indol-3-yl)-propyl ester as a light yellow solid (300 mg, 57% yield, 2 steps)

Step 6: To a solution of mesylate (300 mg, 0.7 mmol) in dry ether (20 mL) was added portionwise LiAlH$_4$ (55 mg, 1.4 mmol) at 0° C. The mixer was stirred at room temperature overnight. After TLC indicated the reaction was finished, the mixture was cooled and carefully quenched with Na$_2$SO$_4$. The mixture was filtered and the filtrate was washed with saturated aqueous NH$_4$Cl and water, dried with Na$_2$SO$_4$, filtered, concentrated and the residue was purified with chromatography (petroleum ether/EtOAc 10:1) to give [(S)-2-(6-chloro-5-fluoro-1H-indol-3-yl)-1-methyl-ethyl]-carbamic acid tert-butyl ester as a light yellow solid (200 mg, 87% yield).

Step 7: A solution of [(S)-2-(6-chloro-5-fluoro-1H-indol-3-yl)-1-methyl-ethyl]-carbamic acid tert-butyl ester (200 mg, 0.6 mmol) in HCl/MeOH (10 mL) was stirred at room temperature. After TLC indicated the reaction was finished, the mixture was concentrated to remove the solvent. To the residue was added EtOAc (50 mL), and the mixture was neutralized with saturated NaHCO$_3$ to pH 8~9, and then extracted with EtOAc. The combined organic phases were dried with Na$_2$SO$_4$, filtered, concentrated to give a crude (S)-2-(6-chloro-5-fluoro-1H-indol-3-yl)-1-methyl-ethylamine which was used without further purification.

Step 8: To a solution of (S)-2-(6-chloro-5-fluoro-1H-indol-3-yl)-1-methyl-ethylamine (120 mg, 0.5 mmol) in EtOH (10 mL) was added 5-chloroisatin (90 mg, 0.5 mmol) and p-TsOH (8 mg, 0.04 mmol). The mixture was heated in a sealed tube at 110 for 16 hours. After TLC indicated the reaction was finished, the mixture was cooled and concentrated. The residue was dissolved in EtOAc (20 mL) and washed with NaOH (1N) and brine, dried with Na$_2$SO$_4$, filtered, concentrated and the residue was purified with chromatography (petroleum ether/EtOAc 5:1) to give 36 (15 mg, 64% yield over two steps).

EXAMPLES

The invention is described with reference to the following examples. It is to be appreciated that the invention is not limited to these examples. Where not otherwise designated the compounds of the invention are in free base form.

Example 1

3-(1H-Indol-3-yl)-1-methyl-propylamine

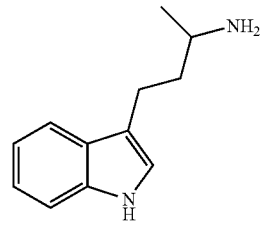

The title compound may be prepared from 4-(1H-indol-3yl)-butan-2-one according to Scheme A.

3-(1H-Indol-3-yl)-1-methyl-propylamine: $^1$H NMR (300 MHz, DMSO-d$_6$): δ 10.71 (s, 1H), 7.50 (d, J=7.5 Hz, 1H), 7.31 (d, J=8.1 Hz, 1H), 7.08 (d, J=2.1 Hz, 1H), 7.04 (td, J=8.1, 1.5 Hz, 1H), 6.95 (td, J=7.2, 1.2 Hz, 1H), 2.81 (m, 1H), 2.70 (m, 2H), 1.61 (m, 2H), 1.02 (d, J=6.3 Hz, 3H); MS (ESI) m/z 189.0 (M+H$^+$).

Example 2

2-(1H-Indol-3-yl)-1-methyl-ethylamine

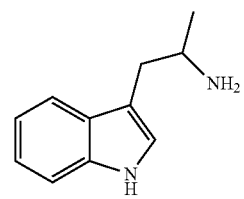

The title compound may be prepared according to Scheme A using the same or analogous synthetic techniques and/or substituting with alternative reagents.

2-(1H-Indol-3-yl)-1-methyl-ethylamine: $^1$H NMR (300 MHz, DMSO-d$_6$): δ 10.79 (s, 1H), 7.51 (d, J=7.8 Hz, 1H), 7.33 (dd, J=7.8, 0.9 Hz, 1H), 7.11 (d, J=2.1 Hz, 1H), 7.04 (td, J=7.8, 1.2 Hz, 1H), 6.95 (td, J=6.9, 0.9 Hz, 1H), 3.07 (m, 1H), 2.62 (m, 2H), 0.98 (d, J=6.3 Hz, 3H); MS (ESI) m/z 175.0 (M+H$^+$).

Example 3

3-(1H-Indol-3-yl)propylamide

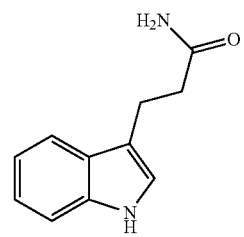 [SMILES: NC(=O)CCc1c[nH]c2ccccc12]

The title compound may be prepared from 3-(1H-indol-3-yl)propanoic acid according to Step 1 of Scheme B.

3-(1H-Indol-3-yl)propylamide: ¹H NMR (300 MHz, DMSO-d₆): δ 10.73 (s, 1H), 7.52 (d, J=9 Hz, 1H), 7.32 (dt, J=7.8 Hz, 0.9 Hz, 1H), 7.29 (s, 1H), 7.09-6.94 (m, 3H), 6.73 (s, 1H), 2.90 (t, J=8.1 Hz, 2H), 2.41 (t, J=7.5 Hz, 2H); MS (ESI) m/z 189.0 (M+H⁺).

Example 4

3-(1H-Indol-3-yl)-propylamine

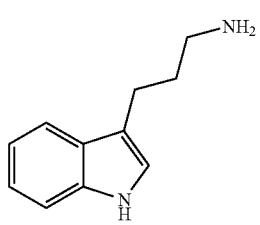 [SMILES: NCCCc1c[nH]c2ccccc12]

The title compound may be prepared from 3-(1H-indol-3-yl)propanoic acid according to Scheme B.

3-(1H-Indol-3-yl)propylamine: ¹H NMR (300 MHz, DMSO-d₆): δ 10.71 (s, 1H), 7.50 (d, J=7.5 Hz, 1H), 7.32 (td, J=8.4, 0.9 Hz, 1H), 7.08 (d, J=1.8 Hz, 1H), 7.04 (td, J=8.1, 1.2 Hz, 1H), 6.95 (td, J=7.2, 0.9 Hz, 1H), 2.69 (m, 2H), 2.59 (m, 2H), 1.71 (m, 2H); MS (ESI) m/z 175.0 (M+H⁺).

Example 5

[3-(1-Indol-3-yl)-propyl]-methyl-amine

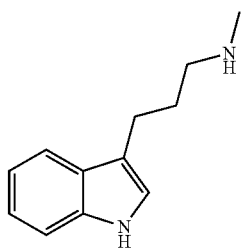

The title compound may be prepared according to Scheme B using the same or analogous synthetic techniques and/or substituting with alternative reagents.

[3-(1H-Indol-3-yl)-propyl]-methyl-amine: ¹H NMR (300 MHz, DMSO-d₆): δ 10.72 (s, 1H), 7.49 (d, J=7.8 Hz, 1H), 7.31 (d, J=8.4 Hz, 1H), 7.08 (d, J=2.1 Hz, 1H), 7.04 (td, J=6.9, 1.2 Hz, 1H), 6.95 (td, J=6.9, 1.2 Hz, 1H), 2.69 (t, J=7.5 Hz, 2H), 2.52 (t, J=7.5 Hz, 2H), 2.28 (s, 3H), 1.76 (m, 2H); MS (ESI) m/z 189.0 (M+H⁺).

Example 6

4-(1H-Indol-3-yl)-butylamine

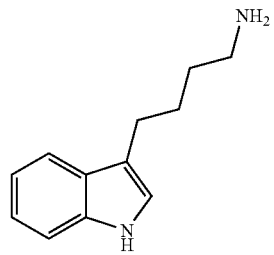 [SMILES: NCCCCc1c[nH]c2ccccc12]

The title compound may be prepared according to Scheme B using the same or analogous synthetic techniques and/or substituting with alternative reagents.

4-(1H-Indol-3-yl)-butylamine: ¹H NMR (300 MHz, DMSO-d₆): δ 10.71 (s, 1H), 7.49 (d, J=7.5 Hz, 1H), 7.31 (d, J=7.5 Hz, 1H), 7.08 (d, J=2.1 Hz, 1H), 7.04 (td, J=7.8, 1.2 Hz, 1H), 6.95 (td, J=7.8, 1.2 Hz, 1H), 2.67 (t, J=7.5 Hz, 2H), 2.56 (t, J=6.9 Hz, 2H), 1.65 (m, 2H), 1.41 (m, 2H); MS (ESI) m/z 189.0 (M+H⁺).

Example 7

5'-Bromo-3-methyl-3,4,5,10-tetrahydro-2H-spiro[azepino[3,4-b]indole-1,3'-indol]-2'(1'H)-one (1)

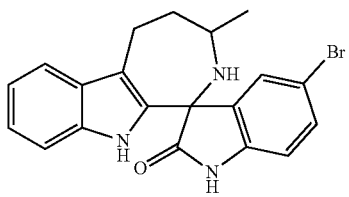

1

Compound 1 may be prepared from 3-(1H-indol-3-yl)-1-methyl-propylamine according to Scheme C.

5'-Bromo-3-methyl-3,4,5,10-tetrahydro-2H-spiro[azepino[3,4-b]indole-1,3'-indol]-2'(1'H)-one: ¹H NMR (600 MHz, DMSO-d₆): δ 10.45 (s, 1H), 9.98 (s, 1H), 8.14 (s, 1H), 7.46 (d, J=8.4 Hz, 2H), 7.26 (s, 1H), 7.16 (d, J=8.4 Hz, 1H), 6.70 (t, J=7.2 Hz, 1H), 6.95 (t, J=7.2 Hz, 1H), 6.87 (d, J=8.4 Hz, 1H), 3.89 (bs, 1H), 3.11 (m, 1H), 2.87 (m, 1H), 2.07 (m, 1H), 1.65 (m, 1H), 1.05 (d, J=6.6 Hz, 3H); MS (ESI) m/z 397.0 (M+H⁺).

Example 8

5'-Chloro-3-methyl-3,4,5,10-tetrahydro-2H-spiro[azepino[3,4-b]indole-1,3'-indol]-2'(1'H)-one (2)

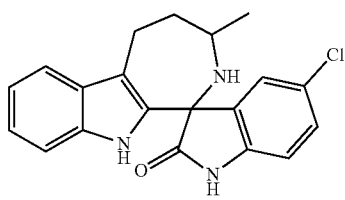

2

Compound may be prepared according to Scheme C using the same or analogous synthetic techniques and/or substituting with alternative reagents.

5'-Chloro-3-methyl-3,4,5,10-tetrahydro-2H-spiro[azepino[3,4-b]indol]-1,3'-indol]-2'(1'H)-one: $^1$H NMR (300 MHz, DMSO-d$_6$): δ 10.43 (s, 1H), 9.95 (s, 1H), 8.25 (s, 1H), 7.46 (dd, J=6.6, 1.8 Hz, 1H), 7.32 (dd, J=8.1, 2.4 Hz, 1H), 7.16 (m, 2H), 6.96 (m, 2H), 6.91 (d, J=8.1 Hz, 1H), 3.89 (m, 1H), 3.11 (m, 1H), 2.86 (m, 1H), 2.07 (m, 1H), 1.64 (m, 1H), 1.04 (d, J=6.6 Hz, 3H); MS (ESI) m/z 352.0 (M+H$^+$).

Example 9

5'-Fluoro-3-methyl-3,4,5,10-tetrahydro-2H-spiro[azepino[3,4-b]indol]-1,3'-indol]-2'(1'H)-one (3)

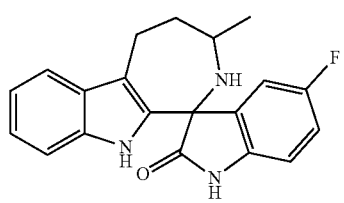

3

Compound 3 may be prepared according to Scheme C using the same or analogous synthetic techniques and/or substituting with alternative reagents.

5'-Fluoro-3-methyl-3,4,5,10-tetrahydro-2H-spiro[azepino[3,4-b]indol]-1,3'-indol]-2'(1'H)-one: $^1$H NMR (300 MHz, DMSO-d$_6$): δ 10.32 (s, 1H), 9.91 (s, 1H), 8.14 (s, 1H), 7.45 (dd, J=6.6, 1.8 Hz, 1H), 7.19-7.06 (m, 2H), 7.03-6.90 (m, 3H), 6.88 (dd, J=8.7, 4.2 Hz, 1H), 3.92 (m, 1H), 3.13 (m, 1H), 2.88 (m, 1H), 2.07 (m, 1H), 1.63 (m, 1H), 1.05 (d, J=6.9 Hz, 3H); MS (ESI) m/z 336.0 (M+H$^+$).

Example 10

3-methyl-3,4,5,10-tetrahydro-2H-spiro[azepino[3,4-b]indol]-1,3'-indol]-2'(1'H)-one (4)

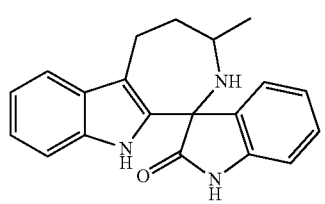

4

Compound 4 may be prepared according to Scheme C using the same or analogous synthetic techniques and/or substituting with alternative reagents.

3-Methyl-3,4,5,10-tetrahydro-2H-spiro[azepino[3,4-b]indol]-1,3'-indol]-2'(1'H)-one: $^1$H NMR (300 MHz, DMSO-d$_6$): δ 11.71 (s, 1H), 10.50 (s, 1H), 8.31 (s, 1H), 7.50 (d, J=7.2 Hz, 1H), 7.25-7.16 (m, 2H), 7.00-6.81 (m, 5H), 4.16-4.07 (m, 1H), 2.78-2.53 (m, 2H), 1.94-1.75 (m, 2H), 1.33 (d, J=60 Hz, 3H) ppm; MS (ESI) m/z 318.0 (M+H$^+$).

Example 11

5'-Bromo-2,3,4,9-tetrahydrospiro[β-carboline-1,3'-indol]-2'(1'H)-one (5)

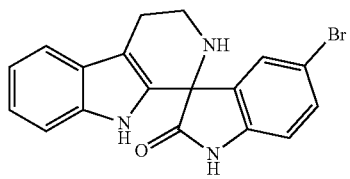

5

Compound 5 may be prepared according to Scheme C using the same or analogous synthetic techniques and/or substituting with alternative reagents.

5% Bromo-2,3,4,9-tetrahydrospiro[β-carboline-1,3'-indol]-2'(1'H)-one: $^1$H NMR (300 MHz, DMSO-d$_6$): δ 10.56 (s, 1H), 10.47 (s, 1H), 8.17 (s, 1H), 7.44 (m, 2H), 7.18 (s, 1H), 7.17 (d, J=7.8 Hz, 1H), 7.00 (m, 2H), 6.89 (d, J=8.4 Hz, 1H), 3.57 (m, 1H), 3.09 (m, 1H), 2.76 (m, 2H); MS (ESI) m/z 369.0 (M+H$^+$).

Example 12

5'-Chloro-2,3,4,9-tetrahydrospiro[β-carboline-1,3'-indol]-2'(1'H)-one (6)

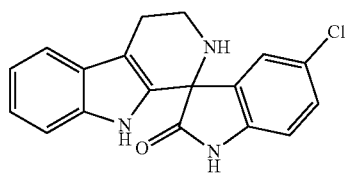

6

Compound 6 may be prepared according to Scheme C using the same or analogous synthetic techniques and/or substituting with alternative reagents.

5'-Chloro-2,3,4,9-tetrahydrospiro[β-carboline-1,3'-indol] 2'(1'H)-one: $^1$H NMR (300 MHz, DMSO-d$_6$): δ 10.57 (s, 1H), 10.48 (s, 1H), 7.47 (d, J=7.2 Hz, 1H), 7.32 (dd, J=8.1, 2.1 Hz, 1H), 7.19 (d, J=7.8 Hz, 1H), 7.09 (d, J=2.1 Hz, 1H), 7.02 (m, 2H), 6.95 (d, J=8.1 Hz, 1H), 3.59 (m, 1H), 3.12 (m, 2H), 2.80 (m, 1H); MS (ESI) m/z 324.0 (M+H$^+$).

Example 13

5'-Chloro-3-methyl-2,3,4,9-tetrahydrospiro[β-carboline-1,3'-indol]-2'(1'H)-one (7)

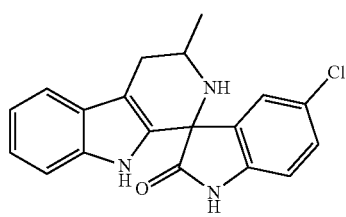

7

Compound 7 may be prepared according to Scheme C using the same or analogous synthetic techniques and/or substituting with alternative reagents.

5'-Chloro-3-methyl-2,3,4,9-tetrahydrospiro[β-carboline-1,3'-indol]-2'(1'H)-one: $^1$H NMR (300 MHz, DMSO-d$_6$): δ 10.45 (s, 1H), 10.42 (s, 1H), 7.43 (d, J=7.2 Hz, 1H), 7.31 (dd, J=8.4, 2.4 Hz, 1H), 7.16 (d, J=7.2 Hz, 1H), 7.03 (d, J=2.4 Hz, 1H), 6.99 (m, 1H), 6.92 (d, J=8.4 Hz, 2H), 3.93 (m, 1H), 3.05 (d, J=6.3 Hz, 1H), 2.79 (dd, 15.0, 3.6 Hz, 1H), 2.41 (dd, J=15.0, 10.5 Hz, 1H), 1.18 (d, J=6.3 Hz, 3H); MS (ESI) m/z 338.0 (M+H$^+$).

Example 14

5'-Bromo-3,4,5,10-tetrahydro-2H-spiro[azepino[3,4-b]indole-1,3'-indol]-2'(1'H)-one (8)

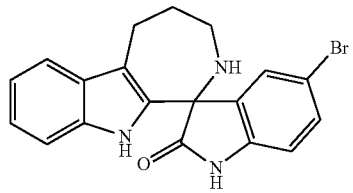

8

Compound 8 may be prepared according to Scheme C using the same or analogous synthetic techniques and/or substituting with alternative reagents.

5'-Bromo-3,4,5,10-tetrahydro-2H-spiro[azepino[3,4-b]indole-1,3'-indol]-2'(1'H)-one: $^1$H NMR (300 MHz, DMSO-d$_6$): δ 10.58 (bs, 1H), 10.11 (s, 1H), 7.46 (m, 2H), 7.26 (d, J=2.1 Hz, 1H), 7.16 (dd, J=6.6, 1.2 Hz, 1H), 6.97 (m, 2H), 6.89 (d, J=8.4 Hz, 1H), 3.46 (m, 1H), 3.01 (m, 3H), 1.98 (m, 2H); MS (ESI) m/z 383.0 (M+H$^+$).

Example 15

5'-Chloro-2,3,4,5,6,11-hexahydrospiro[azocino[3,4-b]indole-1,3'-indol]-2'(1'H)-one (9)

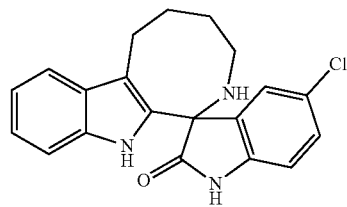

9

Compound 9 may be prepared according to Scheme C using the same or analogous synthetic techniques and/or substituting with alternative reagents.

5'-Chloro-2,3,4,5,6,11-hexahydrospiro[azocino[3,4-b]indole-1,3'-indol]-2'(1'H)-one: $^1$H NMR (300 MHz, DMSO-d$_6$): δ 10.54 (s, 1H), 8.45 (bs, 1H), 7.47 (d, J=7.8 Hz, 1H), 7.43 (d, J=2.1 Hz, 1H), 7.33 (m, 2H), 7.05 (m, 2H), 6.96 (m, 1H), 2.54 (m, 1H), 2.40 (m, 3H), 1.39 (m, 4H); MS (ESI) m/z 352.0 (M+H$^+$).

Example 16

1'-Benzyl-5'-chloro-3,4,5,10-tetrahydro-2H-spiro[azepino[3,4-b]indole-1,3'-indol]-2'(1'H)-one (10)

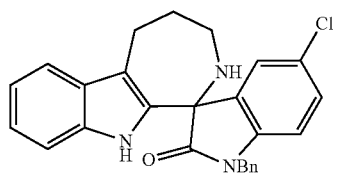

10

Compound 10 may be prepared according to Scheme C using the same or analogous synthetic techniques and/or substituting with alternative reagents.

1'-Benzyl-5'-chloro-3,4,5,10-tetrahydro-2H-spiro[azepino[3,4-b]indole-1,3'-indol]-2'(1'H)-one: $^1$H NMR (300 MHz, DMSO-d$_6$): δ 10.13 (s, 1H), 7.49 (d, J=7.2 Hz, 1H), 7.34 (m, 5H), 7.29 (m, 1H), 7.25 (d, J=2.1 Hz, 1H), 7.18 (d, J=7.2 Hz, 1H), 6.99 (m, 3H), 4.92 (dd, J=77.1, 16.2 Hz, 2H), 3.51 (m, 1H), 3.07 (m, 3H), 2.02 (m, 2H); MS (ESI) m/z 429.0 (M+H$^+$).

Example 17

(1S,3S)-5'-Chloro-3-(hydroxymethyl)-2,3,4,9-tetrahydrospiro[β-carboline-1,3'-indol]-2'(1'H)-one (11)

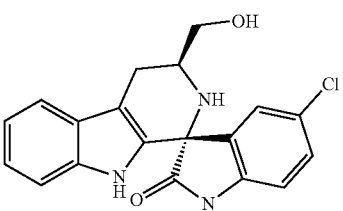

11

Compound 11 may be prepared according to Scheme C using the same or analogous synthetic techniques and/or substituting with alternative reagents.

(1S,3S)-5'-Chloro-3-(hydroxymethyl)-2,3,4,9-tetrahydrospiro[β-carboline-1,3'-indol]-2'(1'H)-one: $^1$H NMR (300 MHz, DMSO-d$_6$): δ 10.49 (s, HT), 10.45 (s, 1H), 7.45 (d, J=6.9 Hz, 1H), 7.33 (dd, J=8.1, 2.1 Hz, 1H), 7.17 (m, 1H), 7.07-6.91 (m, 4H), 4.65 (t, J=5.4 Hz, 1H), 3.92 (m, 1H), 3.50 (t, J=5.4 Hz, 1H), 2.89 (m, 1H), 2.80 (dd, J=15.0, 3.6 Hz, 1H), 2.44 (m, 1H); MS (ESI) m/z 354.0 (M+H$^+$).

Example 18

Di-tert-butyl 5'-bromo-3-methyl-2'-oxo-4,5-dihydro-2H-spiro[azepino[3,4-b]indole-1,3'-indole]-1',10(2'H,3H)-(dicarboxylate (12)

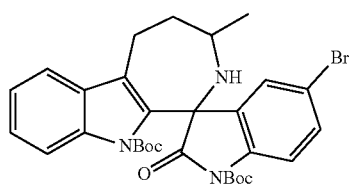

Compound 12 may be prepared according to Steps 1 and 2 of Scheme C.

Di-tert-butyl 5'-bromo-3-methyl-2'-oxo-4,5-dihydro-2H-spiro[azepino[3,4-b]indole-1,3'-indole]-1',10(2'H,3H)-dicarboxylate: $^1$H NMR (300 MHz, DMSO-d$_6$): δ 7.71 (m, 3H), 7.51 (dd, J=8.6, 2.1 Hz, 1H), 7.30 (m, 2H), 6.99 (d, J=2.1 Hz, 1H), 3.10 (m, 2H), 2.87 (m, 1H), 2.16 (m, 1H), 1.63 (m, 1H), 1.57 (s, 9H), 1.33 (s, 9H), 1.00 (d, J=6.6 Hz, 3H); MS (ESI) m/z 597.0 (M+H$^+$).

Example 19 tert-Butyl 5'-bromo-3-methyl-2'-oxo-3,4,5,10-tetrahydro-2H-spiro[azepino[3,4-b]indole-1,3'-indole]-1'(2'H)-carboxylate (13)

Compound 13 may be prepared according to Scheme C.

tert-Butyl 5'-bromo-3-methyl-2'-oxo-3,4,5,10-tetrahydro-2H-spiro[azepino[3,4-b]indole-1,3'-indole]-1'(2'H)-carboxylate: $^1$H NMR (300 MHz, DMSO-d$_6$): δ 10.33 (s, 1H), 7.70 (d, J=7.5 Hz, 1H), 7.64 (d, J=7.2 Hz, 1H), 7.28 (m, 3H), 6.83 (d, J=2.1 Hz, 1H), 6.74 (d, J=8.4 Hz, 1H), 3.47 (m, 1H), 2.97 (m, 1H), 2.82 (m, 1H), 2.37 (m, 1H), 1.65 (m, 1H), 1.30 (s, 9H), 1.02 (d, J=6.6 Hz, 3H); MS (ESI) m/z 497.0 (M+H$^+$).

Example 20

Methyl (1S,3S)-5'-bromo-2'-oxo-1',2,2',3,4,9-hexahydrospiro[β-carboline-1,3'-indole]-3-carboxylate (14)

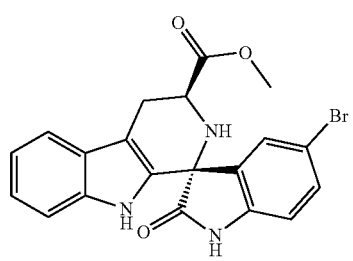

Compound 14 may be prepared according to Scheme C using the same or analogous synthetic techniques and/or substituting with alternative reagents.

Methyl (1S,3S)-5'-bromo-2'-oxo-1',2,2',3,4,9-hexahydrospiro[β-carboline-1,3'-indole]-3-carboxylate: $^1$H NMR (300 MHz, DMSO-d$_6$): δ 10.60 (s, 1H), 10.54 (s, 1H), 7.50-7.46 (m, 2H), 7.28 (d, J=2.1 Hz, 1H), 7.18 (d J=7.8 Hz, 1H), 7.08-6.96 (m, 2H), 6.90 (d, J=8.1 Hz, 1H), 4.73-4.66 (m, 1H), 3.71 (s, 3H), 3.51 (d, J=7.2 Hz, 1H), 3.08 (dd, J=3.9, 15.0 Hz, 1H), 2.88 (dd, J=11.1, 15.2 Hz, 1H); MS (ESI) m/z 427.0 (M+H)$^+$.

Example 21

Ethyl (1S,3S)-5'-bromo-2'-oxo-1',2,2',3,4,9-hexahydrospiro[β-carboline-1,3'-indole]-3-carboxylate (15)

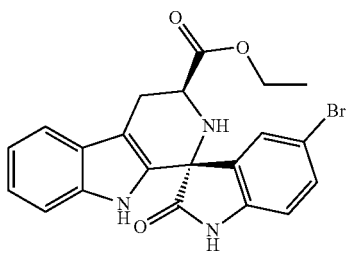

Compound 15 may be prepared according to Scheme C using the same or analogous synthetic techniques and/or substituting with alternative reagents.

Ethyl (1S,3S)-5'-bromo-2'-oxo-1',2,2',3,4,9-hexahydrospiro[β-carboline-1,3'-indole]-3-carboxylate: $^1$H NMR (300 MHz, DMSO-d$_6$): δ 10.59 (s, 1H), 10.54 (s, 1H), 7.50-7.46 (m, 2H), 7.29 (d, J=2.1 Hz, 1H), 7.18 (d, J=7.8 Hz, 1H), 7.08-6.96 (m, 2H), 6.90 (d, J=8.1 Hz, 1H), 4.70-4.63 (m, 1H), 4.18 (q, J=7.2 Hz, 2H), 3.47 (d, J=6.9 Hz, 1H), 3.08 (dd, J=4.2, 15.0 Hz, 1H), 2.87 (dd, J=11.1, 15.0 Hz, 1H), 1.26 (t, J=6.9 Hz, 3H); MS (ESI) m/z 441.0 (M+H)$^+$.

Example 22

Methyl (1S,3R)-5'-chloro-2'-oxo-1',2,2',3,4,9-hexahydrospiro[β-carboline-1,3'-indole]-3-carboxylate (16)

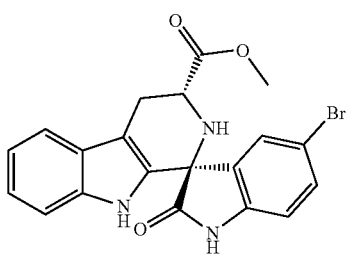

Compound 16 may be prepared according to Scheme C using the same or analogous synthetic techniques and/or substituting with alternative reagents.

Methyl (1S,3R)-5'-chloro-2'-oxo-1',2,2',3,4,9-hexahydrospiro[β-carboline-1,3'-indole]-3-carboxylate: $^1$H NMR (300 MHz, DMSO-d$_6$): δ 10.59 (s, 1H), 10.54 (s, 1H), 7.50-7.46 (m, 2H), 7.28 (d, J=2.1 Hz, 1H), 7.18 (d, J=7.8 Hz, 1H), 7.08-6.96 (m, 2H), 6.90 (d, J=8.4 Hz, 1H), 4.73-4.66 (m, 1H), 3.71 (s, 3H), 3.51 (d, J=6.9 Hz, 1H), 3.08 (dd, J=3.9, 15.0 Hz, 1H), 2.88 (dd, J=11.1, 15.3 Hz, 1H); MS (ESI) m/z 427.0 (M+H)+.

Example 23

Ethyl (1S,3R)-5'-chloro-2'-oxo-1',2,2',3,4,9-hexahydrospiro[β-carboline-1,3'-indole]-3-carboxylate (17)

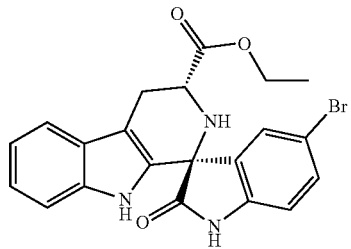

17

Compound 17 may be prepared according to Scheme C using the same or analogous synthetic techniques and/or substituting with alternative reagents.

Ethyl (1S,3R)-5'-chloro-2-oxo-1',2,2',3,4,9-hexahydrospiro[β-carboline-1,3'-indole]-3-carboxylate: $^1$H NMR (300 MHz, DMSO-d$_6$): δ 10.59 (s, 1H), 10.54 (s, 1H), 7.50-7.46 (m, 2H), 7.29 (d, J=1.8 Hz, 1H), 7.18 (d, J=7.8 Hz, 1H), 7.08-6.96 (m, 2H), 6.90 (d, J=8.1 Hz, 1H), 4.70-4.63 (m, 1H), 4.18 (q, J=7.2 Hz, 2H), 3.47 (d, J=6.9 Hz, 1H), 3.07 (dd, J=4.5, 15.2 Hz, 1H), 2.87 (dd, J=11.1, 15.0 Hz, 1H), 1.26 (t, J=7.2 Hz, 3H) ppm; MS (ESI); m/z 441.0 (M+H)+.

Example 24

(1S,3R)-5'-Chloro-3-(hydroxymethyl)-2,3,4,9-tetrahydrospiro[β-carboline-1,3'-indol]-2'(1'H)-one (18)

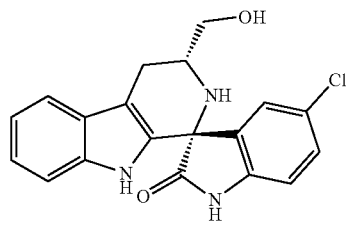

18

Compound 18 may be prepared according to Scheme C using the same or analogous synthetic techniques and/or substituting with alternative reagents.

(1S,3R)-5'-Chloro-3-(hydroxymethyl)-2,3,4,9-tetrahydrospiro[β-carboline-1,3'-indol]-2'(1'H)-one: $^1$H NMR (300 MHz, DMSO-d$_6$): δ 10.49 (s, 1H), 10.45 (s, 1H), 7.45 (d, J=6.9 Hz, 1H), 7.32 (dd, J=2.1, 8.3 Hz, 1H), 7.17 (d, J=7.2 Hz, 1H), 7.06-6.92 (m, 4H), 4.64 (t, J=6.0 Hz, 1H), 3.95-3.86 (m, 1H), 3.49 (t, J=5.7 Hz, 1H), 2.90 (d, J=6 Hz, 1H), 2.80 (dd, J=3.9, 14.9 Hz, 1H), 2.45-2.40 (m, 1H); MS (ESI) m/z 354.0 (M+H)+

Example 25

5'-Bromo-1',3-dimethyl-3,4,5,10-tetrahydro-2H-spiro[azepino[3,4-b]indole-1,3'-indol]-2'-one (19)

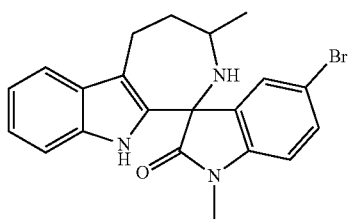

19

Compound 19 may be prepared according to Scheme C using the same or analogous synthetic techniques and/or substituting with alternative reagents.

5'-Bromo-1',3-dimethyl-3,4,5,10-tetrahydro-2H-spiro[azepino[3,4-b]indole-1,3'-indol]-2'-one: $^1$H NMR (300 MHz, DMSO-d$_6$): δ 9.99 (s, 1H), 7.56 (dd, J=2.1, 8.6 Hz, 1H), 7.48-7.45 (m, 1H), 7.30 (d, J=2.1 Hz, 1H), 7.16-7.13 (m, 1H), 7.07 (d, J=8.4 Hz, 1H) 7.02-6.92 (m, 2H), 3.93-3.85 (m, 1H), 3.21-3.12 (m, 4H), 2.93-2.84 (m, 2H), 2.11-1.99 (m, 1H), 1.71-1.59 (m, 1H), 1.03 (d, J=6.9 Hz, 3H); MS (ESI) m/z 413.0 (M+H)+

Example 26

(4S,6S)-5'-chloro-6-(hydroxymethyl)-3,5,6,7-tetrahydrospiro[imidazo[4,5-c]pyridine-4,3'-indol]-2'(1'H)-one (20)

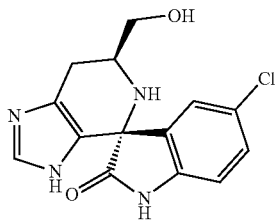

20

Compound 20 may be prepared according to Scheme C using the same or analogous synthetic techniques and/or substituting with alternative reagents.

(4S,6S)-5'-chloro-6-(hydroxymethyl)-3,5,6,7-tetrahydrospiro[imidazo[4,5-c]pyridine-4,3'-indol]-2'(1'H)-one: $^1$H NMR (300 MHz, CD$_3$OD-d$_4$): δ 8.23 (s, 1H), 7.54 (s, 1H), 7.28 (dd, J=8.4 Hz, J=2.1 Hz, 1H), 7.11 (d, J=2.1 Hz, 1H), 6.92 (d, J=9 Hz, 1H), 4.16 (m, 1H), 3.65 (m, 2H), 2.79 (dd, J=15.3 Hz, J=4.2 Hz, 1H), 2.61 (m, 1H); MS (ESI) m/z (M+H)+.

Example 27 tert-Butyl-5'-bromo-3-methyl-2'-oxo-1',2,2',3,4,5-hexahydro-10H-spiro[azepino[3,4-b]indole-1,3'-indole]-10-carboxylate (21)

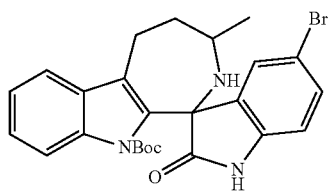

To a solution of compound 1 (10 mg, 0.025 mmol) in dry dichloromethane (0.3 mL) is added triethylamine (7.0 µL, 0.05 mmol) and di-tert-butyl dicarbonate (5.51 mg, 0.025 mmol). The resulting mixture is stirred for 60 hours at room temperature under argon atmosphere and then concentrated to dryness. The residue is subjected to flash column chromatography (silica gel, hexanes:EtOAc, 20:1) to afford compound 21 (3.3 mg, 44%) as white solid.

tert-Butyl-5'-bromo-3-methyl-2'-oxo-1',2,2',3,4,5-hexahydro-10H-spiro[azepino[3,4-b]indole-1,3'-indole]-10-carboxylate: $^1$H NMR (300 MHz, DMSO-$d_6$): δ 10.17 (s, 1H), 7.81 (d, J=8.7 Hz, 1H), 7.62 (dd, J=8.7, 2.1 Hz, 1H), 7.49 (d, J=6.9 Hz, 1H), 7.30 (d, J=2.1 Hz, 1H), 7.15 (d, J=9.0 Hz, 1H), 6.99 (m, 2H), 3.78 (m, 1H), 3.15 (m, 1H), 2.86 (m, 1H), 2.03 (m, 1H), 1.65 (m, 1H), 1.57 (s, 9H), 1.05 (d 6.6 Hz, 3H) ppm; MS (ESI) m/z 497.0 (M+H$^+$).

Example 28

5'-Bromo-1',3,10-trimethyl-3,4,5,10-tetrahydro-2H-spiro[azepino[3,4-b]indole-1,3'-indol]-2'(1'H)-one (22)

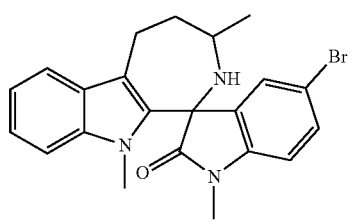

To a solution of compound 1 (15 mg, 0.038 mmol) in dry DMF (0.4 mL) under argon atmosphere is added NaH (5.3 mg, 0.133 mmol) at room temperature. The solution becomes dark red as it is stirred for 30 minutes at room temperature. Iodomethane (9.43 µL, 0.152 mmol) is then added to the reaction mixture and the mixture is stirred for a further one hour at room temperature. The reaction mixture is then concentrated to dryness and water (10 mL) is added. The aqueous layer is extracted with EtOAc (3×15 mL). The combined organic phases are washed with brine (20 mL), dried (Na$_2$SO$_4$) and concentrated in vacuo. The residue is subjected to flash column chromatography (silica gel, hexanes:EtOAc, 8:2) to afford compound 22 (10.3 mg, 64%) as white solid.

5'-Bromo-1',3,10-trimethyl-3,4,5,10-tetrahydro-2H-spiro[azepino[3,4-b]indole-1,3'-indol]-2'(1'H)-one: $^1$H NMR (300 MHz, DMSO-$d_6$): δ 7.57 (m, 2H), 7.25 (d, J=7.8 Hz, 1H), 7.16-6.98 (m, 4H), 3.74 (m, 1H), 3.24 (s, 3H), 3.01 (d, J=5.7 Hz, 1H), 2.96 (s, 3H), 2.88 (m, 1H), 2.02 (m, 1H), 1.63 (m, 1), 1.00 (d, J=6.6 Hz, 3H); MS (ESI) m/z, 425.0 (M+H$^+$).

Example 29

5'-Bromo-10-[(3-bromophenyl)carbonyl]3-methyl-3,4,5,10-tetrahydro-2H-spiro[azepino-[3,4-b]indole-1,3'-indol]-2'(1'H)-one (23)

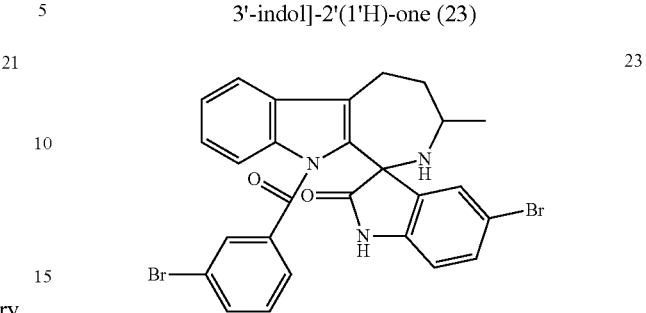

To a solution of compound 1 (30 mg, 0.076 mmol) in dry dichloromethane (0.8 mL) is added triethylamine (31.48 µL, 0.228 mmol), 3-bromo-benzoyl chloride (59.8 µL, 0.456 mmol) and 4-dimethylaminopyridine (13.9 mg, 0.114 mmol). The resulting mixture is stirred for 16 hours at room temperature and then concentrated to dryness. The residue is subjected to flash column chromatography (silica gel, 0%-10% EtOAc in hexanes) to afford compound 23 (15.3 mg, 37%) as white solid.

5'-Bromo-10-[3-bromophenyl)carbonyl]-3-methyl-3,4,5,10-tetrahydro-2H-spiro[azepino-[3,4-b]indole-1,3'-indol]-2'(1'H)-one: $^1$H NMR (300 MHz, DMSO-$d_6$): δ 10.44 (s, 1H), 7.97 (s, 1H), 7.92 (d, J=8.7 Hz, 1H), 7.81 (d, J=8.1 Hz, 1H), 7.75 (d, J=8.1 Hz, 1H), 7.69 (dd, J=8.7, 2.1 Hz, 1H), 7.49 (d, J=8.1 Hz, 2H), 7.34 (d, J=2.1 Hz, 1H), 7.16 (d, J=7.5 Hz, 1H), 6.99 (m, 2H), 3.63 (m, 1H), 3.45 (m, 1H), 2.83 (m, 1H), 1.96 (m, 1H), 1.66 (m, 1H), 1.12 (d, J=6.6 Hz, 3H); MS (ESI) m/z 580.0 (M+H$^+$).

Example 30

5'-Bromo-3-methyl-10-{[4-(trifluoromethoxy)phenyl]sulfonyl}-3,4,5,10-tetrahydro-2H-spiro[azepino[3,4-b]indole-1,3'-indol]-2'(1'H)-one (24)

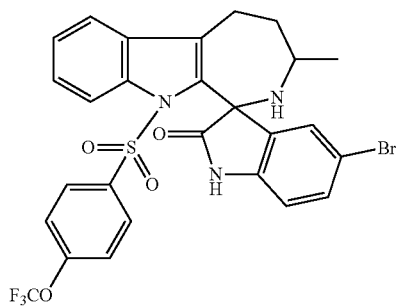

To a solution of compound 1 (20 mg, 0.05 mmol) in 0.5 mL of dry dichloromethane is added triethylamine (14.0 µL, 0.101 mmol), followed by 4-(trifluoromethoxy)benzenesulphonyl chloride (20.6 µL, 0.121 mmol) and 4-dimethylaminopyridine (12.3 mg, 0.101 mmol). The solution is stirred for 16 h at room temperature under argon atmosphere. The reaction mixture is concentrated to dryness. The crude mixture is subjected to flash chromatography column to afford compound 24 (9.1 mg, 29%).

5'-Bromo-3-methyl-10-{[4-(trifluoromethoxy)phenyl]sulfonyl}-3,4,5,10-tetrahydro-2H-spiro[azepino[3,4-b]indole-1,3'-indol]-2'(1'H)-one: ¹H NMR (300 MHz, DMSO-d₆): δ 10.1 (s, 1H), 8.17 (d, J=9.0 Hz, 2H), 7.83 (d, J=9.0 Hz, 1H), 7.73 (dd, J=2.1, 8.7 Hz, 1H), 7.65 (d, J=8.7 Hz, 2H), 7.47 (d, J=7.5 Hz, 1H), 7.31 (d, J=2.1 Hz, 1H), 7.13 (d, J=8.1 Hz, 1H), 7.05-6.93 (m, 2H), 3.48-3.38 (m, 1H), 3.11-3.02 (m, 1H), 2.83-2.74 (m, 1H), 2.03-1.95 (m, 1H), 1.65-1.57 (m, 1H), 0.87 (d, J=6.6 Hz, 3H); MS (ESI) m/z 621.0 (M+H)⁺.

Example 31

5'-Bromo-10-[(4-methoxyphenyl)carbonyl]-3-methyl-3,4,5,10-tetrahydro-2H-spiro[azepino-[3,4-b]indole-1,3'-indol]-2'(1'H)-one (25)

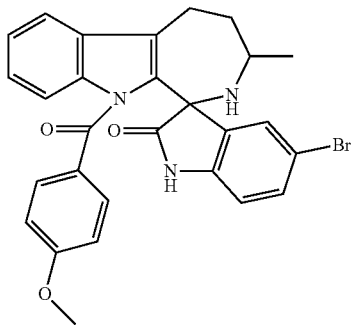

25

Compound 25 may be prepared using the same or analogous synthetic techniques and/or substituting with alternative reagents as described above in Example 30.

5'-Bromo-10-[(4-methoxyphenyl)carbonyl]-3-methyl-3,4,5,10-tetrahydro-2H-spiro[azepino-[3,4-b]indole-1,3'-indol]-2'(1'H)-one: ¹H NMR (300 MHz, DMSO-d₆): δ 10.4 (s, 1H), 7.80-7.75 (m, 2H), 7.72 (s, 1H), 7.65 (dd, J=1.8, 8.7 Hz, 1H), 7.50 (d, J=6.9 Hz, 1H), 7.33 (d, J=1.8 Hz, 1H), 7.18-7.13 (m, 1H), 7.06-7.02 (m, 3H), 7.01-6.96 (m, 1H), 3.84 (s, 3H), 3.72-3.65 (m, 1H), 3.24-3.14 (m, 1H), 2.88-2.79 (m, 1H), 2.06-1.95 (m, 1H), 1.74-1.62 (m, 1H), 1.17 (d, J=6.6 Hz, 3 H) ppm; MS (ESI) m/z 531.0 (M+H)⁺.

Example 32

(1R,3S)-9-(3-aminopropyl)-5'-chloro-3-methyl-2,3,4,9-tetrahydrospiro[β-carboline-1,3'-indol]-2'(1'H)-one (26)

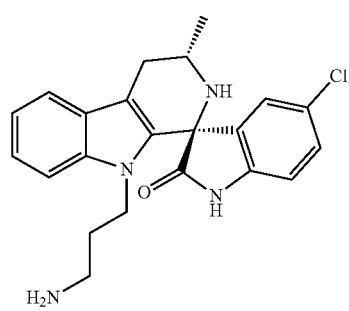

26

Compound 26 may be prepared using the same or analogous synthetic techniques and/or substituting with alternative reagents as described above in Scheme F.

(1R,3S)-9-(3-aminopropyl)-5'-chloro-3-methyl-2,3,4,9-tetrahydrospiro[β-carboline-1,3'-indol]-2'(1'H)-one: ¹H NMR (400 MHz, DMSO-d₆): δ 11.81 (bs, 1H), 11.22 (bs, 1H), 10.95 (bs, 1H), 7.93 (s, 1H), 7.67 (m, 1H), 7.61 (m, 1H), 7.50 (m, 2H), 7.45 (m, 3H), 4.41 (bs, 1H), 3.72 (m, 1H), 3.47 (m, 1H), 3.17 (m, 1H), 2.78 (m, 3H), 1.16 (m, 3H); MS (ESI) m/z 395.2 (M+H)⁺.

Example 33

N-{3-[(1R,3S)-5'-chloro-3-methyl-2'-oxo-1',2',3,4-tetrahydrospiro[β-carboline-1,3'-indol]-9(2H)-yl]propyl}acetamide (27)

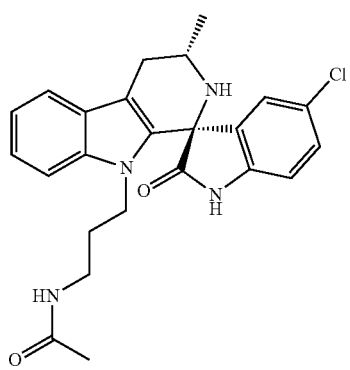

27

Compound 27 may be prepared using the same or analogous synthetic techniques and/or substituting with alternative reagents as described above in Scheme F.

N-{3-[(1R,3S)-5'-chloro-3-methyl-2'-oxo-1',2',3,4-tetrahydrospiro[β-carboline-1,3'-indol]-9(2H)-yl]propyl}acetamide: ¹H NMR (400 MHz, DMSO-d₆): δ 10.65 (s, 1H), 8.13 (s, 1H), 7.67 (m, 1H), 7.50 (d, J=8.0 Hz, 1H), 7.34 (m, 2H), 7.08 (m, 3H), 4.07 (m, 1H), 3.72 (m, 1H), 3.47 (m, 1H), 3.17 (d, J=4.0 Hz, 1H), 2.78 (m, 3H), 1.78 (s, 3H), 1.16 (d, J=8.0 Hz, 3H); MS (ESI) m/z 437.3 (M+H)⁺.

Example 34

(3S,11a'S)-5-Chloro-3',3'-dimethyl-1',6',11',11a'-tetrahydrospiro[indole-3,5'-[1,3]oxazolo-[3',4':1,6]pyrido[3,4-b]indol]-2(1H)-one (28)

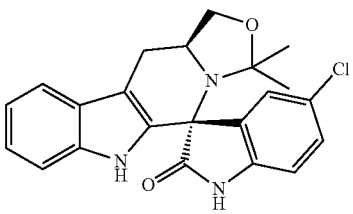

28

To a solution of compound 11 (15 mg, 0.04 mmol) in the mixture of dichloromethane:2,2-dimethoxypropane (1 mL:0.5 mL) is added catalytic amount of pyridinium p-toluenesulfonate at room temperature. The resulting mixture is stirred for 16 h at ambient temperature and then concentrated in vacuo. The residue is subjected to flash column chromatography (silica gel, 10%-40% EtOAc in hexanes) to afford compound 28 (7 mg, 42%) as white solid.

(3S,11a'S)-5-Chloro-3',3'-dimethyl-1',6',11',11a'-tetrahydrospiro[indole-3,5'-[1,3]oxazolo-[3',4':1,6]pyrido[3,4-b]indol]-2(1H)-one: $^1$H NMR (300 MHz, DMSO-d$_6$): δ 10.49 (s, 1H), 10.45 (s, 1H), 7.46 (d, J=6.9 Hz, 1H), 7.33 (dd, J=8.1, 2.4 Hz, 1H), 7.17 (d, J=7.5 Hz, 1H), 7.07-6.59 (m, 3H), 6.93 (d, J=8.7 Hz, 1H), 4.03 (m, 1H), (m, 1H), 3.43 (m, 2H), 2.97 (d, J=6.3 Hz, 1H), 2.86 (dd, J=15.0, 3.9 Hz, 1H), 1.29 (s, 6H); MS (ESI) m/z 395.0 (M+H)$^+$.

Example 35

3-Methyl-5'-phenyl-3,4,5,10-tetrahydro-2H-spiro[azepino[3,4-b]indole-1,3'-indol]-2'(1'H)-one (29)

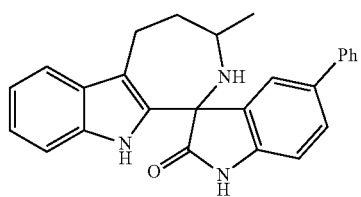

A mixture of compound 1 (7 mg, 0.018 mmol), benzeneboronic acid (2.6 mg, 0.021 mmol) and tetrakis(triphenylphosphine)palladium (2 mg, 0.002 mmol) in DMF (2 mL)/aqueous 2 N sodium bicarbonate solution (0.5 mL) is stirred for 20 minutes in a microwave reactor at 130° C. After being cooled to room temperature, the reaction mixture is extracted with ethyl acetate (3×10 mL). The combined organic phases are dried over sodium sulfate and concentrated in vacuo. The residue is subjected to flash column chromatography (silica gel, 30% EtOAc in hexanes) to afford compound 29 (2.3 mg, 33%) as white solid.

3-Methyl-5'-phenyl-3,4,5,10-tetrahydro-2H-spiro[azepino[3,4-b]indole-1,3'-indol]-2'(1'H)-one: $^1$H NMR (300 MHz, DMSO-d$_6$): δ 10.39 (s, 1H), 9.34 (s, 1H), 7.77 (m, 1H), 7.59 (m, 2H), 7.42 (m, 4H), 7.29 (q, J=7.5 Hz, 1H), 7.16 (m, 1H), 6.99 (d, J=7.8 Hz, 1H), 6.95 (m, 2H), 3.92 (m, 1H), 3.16 (m, 1H), 2.91 (m, 1H), 2.11 (m, 1H), 1.67 (m, 1H), 1.06 (d, J=6.6 Hz, 3H); MS (ESI) m/z 394.0 (M+H)$^+$.

Example 36

3-Methyl-5'-[4-(trifluoromethyl)phenyl]-3,4,5,10-tetrahydro-2H-spiro[azepino[3,4-b]indole-1,3'-indol]-2'(1'H)-one (30)

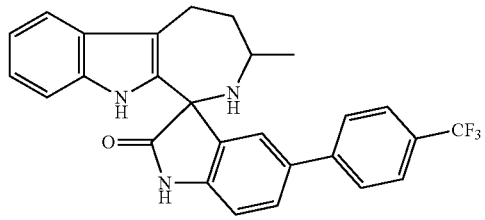

Compound 30 may be prepared using the same or analogous synthetic techniques and/or substituting with alternative reagents as described above in Example 34.

3-Methyl-5'-[4-(trifluoromethyl)phenyl]-3,4,5,10-tetrahydro-2H-spiro[azepino[3,4-b]indol-1,3'-indol]-2'(1'H)-one: $^1$H NMR (300 MHz, DMSO-d$_6$): δ 10.48 (s, 1H), 9.96 (s, 1H), 7.84 (s, 1H), 7.81 (s, 1H), 7.75-7.66 (m, 3H), 7.53 (d, J=1.8 Hz, 1H), 7.47-7.44 (m, 1H), 7.18-7.14 (m, H), 7.03 (d, J=8.1 Hz, 1H), 6.99-6.91 (m, 2H), 3.98-3.86 (m, 1H), 3.21-3.12 (m, 1H), 2.96-2.87 (m, 1H), 2.15-2.08 (m, 1H), 1.73-1.61 (m, 1H), 1.06 (d, J=6.6 Hz, 3H); MS (ESI) m/z 462.0 (M+H)$^+$.

Example 37

3-Methyl-5'-(4-phenoxyphenyl)-3,4,5,10-tetrahydro-2H-spiro[azepino[3,4-b]indole-1,3'indol]-2'(1'H)-one (31)

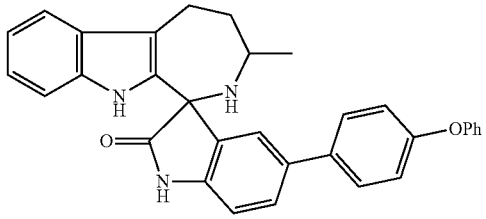

Compound 31 may be prepared using the same or analogous synthetic techniques and/or substituting with alternative reagents as described above in Example 34.

3-Methyl-5'-(4-phenoxyphenyl)-3,4,5,10-tetrahydro-2H-spiro[azepino indole-1,3'-indol]-2'(1'H)-one: $^1$H NMR (300 MHz, DMSO-d$_6$): δ 10.4 (s, 1H), 9.94 (s, 1H), 7.61-7.56 (m, 3H), 7.47-7.35 (m, 4H), 7.17-7.10 (m, 2H), 7.04-7.00 (m, 5H), 6.97-6.91 (m, 2H), 3.98-3.84 (m, 1H), 3.21-3.12 (m, 1H), 2.96-2.86 (m, 1H), 2.14-2.07 (m, 1), 1.72-1.62 (m, 1H), 1.06 (d, J=6.6 Hz, 3H); MS (ESI) m/z 486.0 (M+H)$^+$.

Example 38

5'-Chloro-6-methoxy-3,3-dimethyl-2,3,4-tetrahydrospiro[β-carboline-1,3'-indol]-2'(1'H)-one (32)

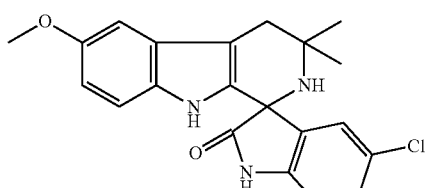

Compound 32 may be prepared according to Scheme D.

5'-Chloro-6-methoxy-3,3-dimethyl-2,3,4,9-tetrahydrospiro[β-carboline-1,3'-indol]-2'(1'H)-one: $^1$H NMR (300 MHz, DMSO-d$_6$): δ 10.5 (s, 1H), 10.3 (s, 1H), 7.27 (dd, J=2.1, 7.2 Hz, 1H), 7.05 (d, J=8.7 Hz, 1H), 6.99 (d, J=2.4 Hz, 1H), 6.94 (d, J=2.4 Hz, 1H), 6.89 (d, J=8.4 Hz, 1H), 6.66 (dd, J=2.4, 6.3 Hz, 1H), 3.75 (s, 3H), 2.71 (q, J=12.3 Hz, 2H), 1.30 (s, 3H), 1.28 (s, 3H); MS (ESI) m/z 382.0 (M+H)⁺.

Example 39

5'-Chloro-3,3-dimethyl-2,3,4,9-tetrahydrospiro[β-carboline-1,3'-indol]-2'(1'H)-one (33)

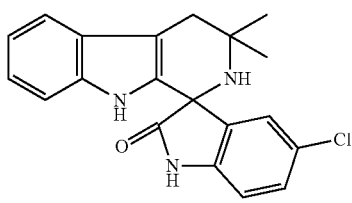

Compound 33 may be prepared using the same or analogous synthetic techniques and/or substituting with alternative reagents as described above in Example 37.

5'-Chloro-3,3-dimethyl-2,3,4,9-tetrahydrospiro[β-carboline-1,3'-indol]-2'(1'H)-one: $^1$H NMR (300 MHz, DMSO-d$_6$): δ 10.55 (s, 1H), 10.51 (s, 1H), 7.44 (d, J=7.51 Hz, 1H), 7.28 (dd, J=2.1, 8.4 Hz, 1H), 7.17 (d, J=8.1 Hz, 1H), 7.05-6.99 (m, 3 H), 6.96-6.89 (m, 1H), 2.74 (q, J=12.3 Hz, 1H), 1.30 (s, 3H), 1.29 (s, 3H); MS (ESI) m/z 352.0 (M+H)⁺.

Example 40

7-Chloroisatin

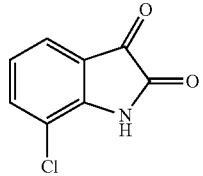 [SMILES: O=C1Nc2c(Cl)cccc2C1=O]

The title compound may be prepared according to Scheme E.

7-Chloroisatin: $^1$H NMR (300 MHz, DMSO-d$_6$): δ 11.45 (s, 1H), 7.67 (dd, J=0.90, 7.95 Hz, 1H), 7.49 (dt, J=0.60, 7.2 Hz, 1H), 7.08 (dd, J=7.50, 7.78 Hz, 1H); MS (ESI) m/z 180.0 (M+H)⁺.

Example 41

5-Methoxyisatin

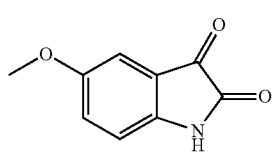

The title compound may be prepared according to Scheme E using the same or analogous synthetic techniques and/or substituting with alternative reagents.

5-Methoxyisatin: $^1$H NMR (300 MHz, DMSO-d$_6$): δ 10.83 (s, 1H), 7.19 (dd, J=2.7, 8.6 Hz, 1H), 7.08 (d, J=1.8 Hz, 1H), 6.85 (d, J=8.7 Hz, 1H), 3.75 (s, 3H); MS (ESI) m/z 178.0 (M+H)⁺.

Example 42

6-Methoxyisatin

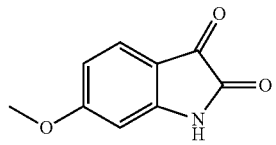

The title compound may be prepared according to Scheme E using the same or analogous synthetic techniques and/or substituting with alternative reagents.

6-Methoxyisatin: $^1$H NMR (300 MHz, DMSO-d$_6$): δ 10.96 (s, 1H), 7.49 (d, J=8.4 Hz, 1H), 6.59 (dd, J=2.4, 8.4, 1H), 6.40 (d, J=2.4 Hz, 1H), 3.88 (s, 3H); MS (ESI) m/z 178.0 (M+H)⁺.

Example 43

7-(Trifluoromethyl)isatin

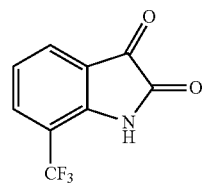 [SMILES: O=C1Nc2c(cccc2C(F)(F)F)C1=O]

The title compound may be prepared according to Scheme E using the same or analogous synthetic techniques and/or substituting with alternative reagents.

7-(trifluoromethyl)isatin: $^1$H NMR (300 MHz, DMSO-d$_6$): δ 11.44 (s, 1H), 7.85 (dd, J=8.1 Hz, 1H), 7.78 (d, J=7.5 Hz, 1H), 7.23 (t, J=7.8 Hz, 1H); MS (ESI) m/z 214.0 (M+H)⁺.

Example 44

5-(tert-Butyl)isatin

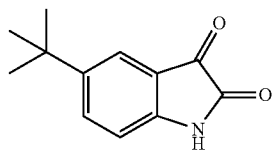

The title compound may be prepared according to Scheme E using the same or analogous synthetic techniques and/or substituting with alternative reagents.

5-(tert-butyl)isatin: $^1$H NMR (300 MHz, DMSO-d$_6$): δ 10.95 (s, 1H), 7.65 (dd, J=1.8, 8.3 Hz, 1H), 7.48 (d, J=2.1 Hz, 1H), 6.87 (d, J=8.1 Hz, 1H), 1.26 (s, 9H); MS (ESI) m/z 204.0 (M+H)$^+$.

Example 45

6,7-Dichloroisatin

The title compound may be prepared according to Scheme F using the same or analogous synthetic techniques and/or substituting with alternative reagents.

6,7-Dichloroisatin: $^1$H NMR (300 MHz, DMSO-d$_6$): δ 11.63 (s, 1H), 7.51 (dd, J=0.90, 7.95 Hz, 1 H), 7.33 (d, J=7.80 Hz, 1 H): MS (ESI); m/z 216.0 (M+H)$^+$.

Example 46

4,7-Dichloroisatin

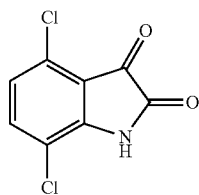 [SMILES: O=C1Nc2c(Cl)ccc(Cl)c2C1=O]

The title compound may be prepared according to Scheme E using the same or analogous synthetic techniques and/or substituting with alternative reagents.

4,7-Dichloroisatin: $^1$H NMR (300 MHz, DMSO-d$_6$): δ 11.60 (s, 1H), 7.65 (d, J=9 Hz, 1H), 7.09 (d, J=8.7 Hz, 1H); MS (ESI) m/z 214.0 (M+H)$^+$.

Example 47

(1R,3S)-5'-Chloro-3-methyl-2,3,4,9-tetrahydrospiro [β-carboline-1,3'-indol]-2'(1'H)-one (34)

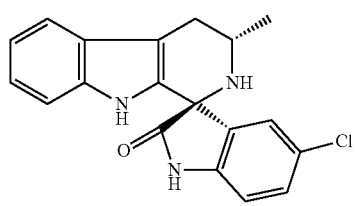

Compound 34 may be prepared according to Scheme F.

(1R,3S)-5'-Chloro-3-methyl-2,3,4,9-tetrahydrospiro[β-carboline-1,3'-indol]-2'(1'H)-one: $^1$H NMR (300 MHz, DMSO-d$_6$): δ 10.45 (s, 1H), 10.42 (s, 1H), 7.43 (d, J=7.2 Hz, 1H), 7.31 (dd, J=2.1, 8.4 Hz, 1H), 7.16 (d, J=7.2 Hz, 7.05-7.02 (m, 2H), 7.00-6.96 (m, 1H), 6.92 (d, J=8.1 Hz, 1H), 3.98-3.86 (m, 1H), 2.79 (dd, J=14.9, 3.3 Hz, 1H), 2.41 (dd, J=4.5, 2.5 Hz, 1H), 1.18 (d, J=6.0 Hz, 3H); MS (ESI) m/z 338.0 (M+H)$^+$.

Example 48

(1S,3R)-5'-Chloro-3-methyl-2,3,4,9-tetrahydrospiro [β-carboline-1,3'-indol]-2'(1'H)-one (35)

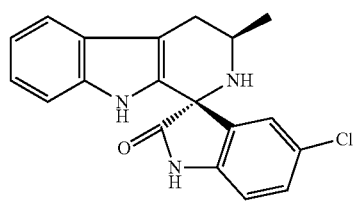

Compound 35 may be prepared according to Scheme F using the same or analogous synthetic techniques and/or substituting with alternative reagents.

(1S,3R)-5'-Chloro-3-methyl-2,3,4,9-tetrahydrospiro[β-carboline-1,3'-indol]-2'(1'H)-one: $^1$H NMR (300 MHz, DMSO-d$_6$): δ 10.45 (s, 1H), 10.42 (s, 1H), 7.43 (d, J=7.5 Hz, 1H), 7.31 (dd, J=2.1, 8.4 Hz, 1H), 7.16 (d, J=7.2 Hz, 1H), 7.05-7.02 (m, 2H), 7.00-6.96 (m, 1H), 6.92 (d, J=8.1 Hz, 1H), 3.98-3.86 (m, 1H), 2.78 (dd, J=3.6, 14.9 Hz, 1H), 2.41 (dd, J=4.5, 25.5 Hz, 1H), 1.18 (d, J=6.3 Hz, 3H); MS (ESI) m/z 338.0 (M+H)$^+$.

Chiral compounds such as 36 and 37 can be prepared according to Scheme G or H using the same or analogous synthetic techniques and/or substituting with alternative reagents.

Example 49

(1R,3S)-5',7-Dichloro-6-fluoro-3-methyl-2,3,4,9-tetrahydrospiro[β-carboline-1,3'-indol]-2'(1'H)-one (36)

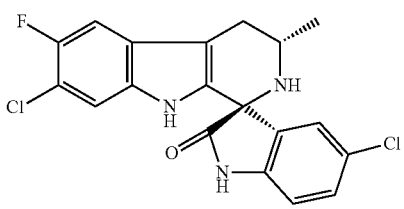

35: $^1$H NMR (500 MHz, DMSO-d$_6$) δ 10.69 (s, 1H), 10.51 (s, 1H), 7.43 (d, J=10.0 Hz, 1H), 7.33 (dd, J=8.4, 2.2 Hz, 1H), 7.27 (d, J=6.5 Hz, 1H), 7.05 (d, J=2.3, 1H), 6.93 (d, J=8.5 Hz, 1H), 3.91 (m, 1H), 3.13 (bd, J=6.2 Hz, 1H), 2.74 (dd, J=15.0, 3.0 Hz, 1H), 2.35 (dd, J=15.0, 10.3, 1H), 1.15 (d, J=6.0, 3H); MS (ESI) m/z 392.0 (M+2H)$^+$; [α]$^{25}_D$=+255.4°

Example 50

(1S,3R)-5',7-Dichloro-6-fluoro-3-methyl-2,3,4,9-tetrahydrospiro[β-carboline-1,3'-indol]-2'(1'H)-one (37)

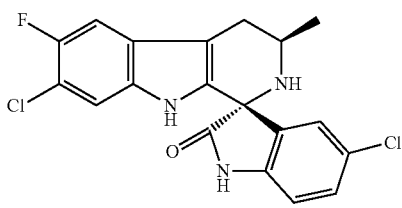

(1S,3R)-5',7-Dichloro-6-fluoro-3-methyl-2,3,4,9-tetrahydrospiro[β-carboline-1,3'-indol]-2'(1'H)-one: $^1$H NMR (500 MHz, CDCl$_3$) δ 8.49 (s, 1H), 7.54 (s, 1H), 7.24 (d, J=9.7 Hz, 1H), 7.21 (dd, J=8.6, 2.0 Hz, 1H), 7.14 (d, J=6.0 Hz, 1H), 7.11 (d, J=1.8, 1H), 6.77 (d, J=8.3 Hz, 1H), 4.14 (m, 1H), 2.89 (dd, J=15.4, 3.7 Hz, 1H), 2.49 (dd, J=15.3, 10.5, 1H), 1.68 (bs, 1H), 1.29 (d, J=6.4 Hz, 3H); MS (ESI) m/z 392.0 (M+2H)$^+$; $[α]^{25}_D$ −223.3°

Example 51

3-methyl-2,3,4,9-tetrahydrospiro[β-carboline-1,3'-indol]-2'(1'H)-one (38)

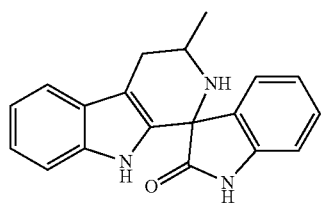

3-Methyl-2,3,4,9-tetrahydrospiro[β-carboline-1,3'-indol]-2'(1'H)-one: $^1$H NMR (300 MHz, DMSO-d6): δ 10.34 (s, 1H), 10.30 (s, 1H), 7.39-7.45 (m, 1H), 7.26 (td, J=7.6, 1.5 Hz, 1H), 7.12-7.18 (m, 1H), 6.85-7.08 (m, 5H), 3.89-4.02 (m, 1H), 2.79 (dd, J=14.9, 3.8 Hz, 1H), 2.41 (dd, J=14.9, 10.6 Hz, 1H), 1.18 (d, J=6.5 Hz, 3H); MS (ESI) m/z 304.0 (M+H)$^+$.

Example 52

6'-Chloro-3-methyl-2,3,4,9-tetrahydrospiro[β-carboline-1,3'-indol-2'(1'H)-one (39)

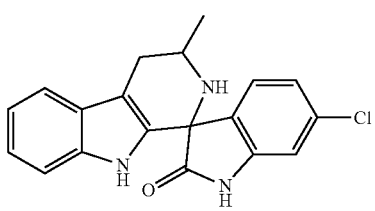

6'-Chloro-3-methyl-2,3,4,9-tetrahydrospiro[β-carboline-1,3'-indol]-2'(1'H)-one: $^1$H NMR (300 MHz, DMSO-d$_6$): δ 10.46 (s, 1H), 10.39 (s, 1H), 7.42 (d, J=7.0 Hz, 1H), 7.15 (d, J=7.0 Hz, 1H), 6.87-7.07 (m, 5H), 3.86-4.04 (m, 1H), 3.03 (d, J=5.3 Hz, 1H), 2.78 (dd, J=14.9, 3.8 Hz, 1H), 2.40 (dd, J=14.9, 10.6 Hz, 1H), 1.17 (d, 3H); MS (ESI) m/z 338.0 (M+H)$^+$.

Example 53

5'-tert-Butyl-3-methyl-2,3,4,9-tetrahydrospiro[β-carboline-1,3'-indol-2'(1'H)-one (40)

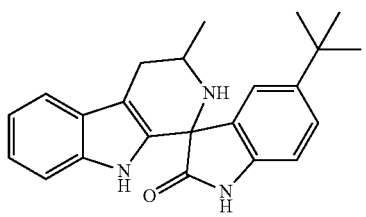

5'-tert-Butyl-3-methyl-2,3,4,9-tetrahydrospiro[β-carboline-1,3'-indol-2'(1'H)-one: $^1$H NMR (300 MHz, MeOD-d$_4$): δ 8.25 (s, 1H), 7.33-7.58 (m, 3H), 6.94-7.26 (m, 4H), 4.42-4.56 (m, 1H), 3.10 (dd, J=15.0, 6.0 Hz, 1H), 2.77 (dd, J=15.8, 10.8 Hz, 1H), 1.43 (d, J=6.7 Hz, 3H), 1.27 (s, 9H); MS (ESI) m/z 360.0 (M+H)$^+$.

Example 54

6',7'-Dichloro-3-methyl-2,3,4,9-tetrahydrospiro[β-carboline-1,3'-indol]-2'(1'H)-one (41)

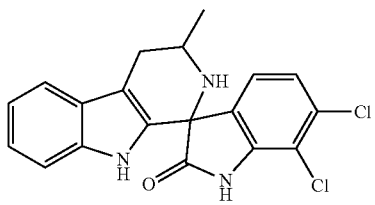

6',7'-Dichloro-3-methyl-2,3,4,9-tetrahydrospiro[β-carboline-1,3'-indol-2'(1'H)-one: $^1$H NMR (300 MHz, DMSO-d$_6$): δ 10.92 (s, 1H), 10.49 (s, 1H), 7.43 (d, J=7.0 Hz, 1H), 7.10-7.24 (m, 2H), 6.92-7.08 (m, 3H), 3.84-4.13 (m, 1H), 3.24 (d, J=4.7 Hz, 1H), 2.79 (dd, J=14.8, 3.7 Hz, 1H), 2.40 (dd, J=14.9, 10.6 Hz, 1H), 1.18 (d, J=6.15 Hz, 3H); MS (ESI) m/z 372.0 (M+H)$^+$.

Example 55

3-Methyl-7'-(trifluoromethyl)-2,3,4,9-tetrahydrospiro[β-carboline-1,3'-indol]-2'(1'H)-one (42)

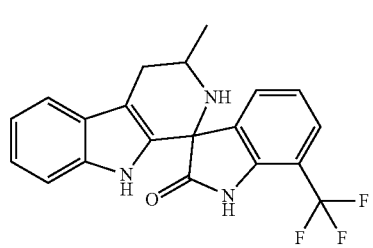

3-Methyl-7'-(trifluoromethyl)-2,3,4,9-tetrahydrospiro[β-carboline-1,3'-indol]-2'(1'H)-one: ¹H NMR (300 MHz, DMSO-d₆): δ 10.74 (s, 1H), 10.48 (s, 1H), 7.54 (d, J=7.9 Hz, 1H), 7.44 (d, J=7.0 Hz, 1H), 7.28 (d, J=7.0 Hz, 1H), 6.89-7.19, (m, 4H), 3.87-4.10 (m, 1H), 3.17 (d, J=5.3 Hz, 1H), 2.81 (dd, J=15.1, 3.7 Hz, 1H), 2.43 (dd, J=14.9, 10.6 Hz, 1H), 1.18 (d, J=6.5 Hz, 3H); MS (ESI) m/z 372.0 (M+H)⁺.

Example 56

7'-Chloro-3-methyl-2,3,4,9-tetrahydrospiro[β-carboline-1,3'-indol]-2'(1'H)-one (43)

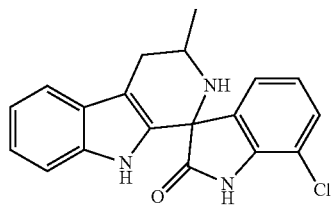

43

7'-Chloro-3-methyl-2,3,4,9-tetrahydrospiro[β-carboline-1,3'-indol]-2'(1'H)-one: ¹H NMR (300 MHz, MeOD-d₄): δ 7.48-7.58 (m, 2H), 7.03-7.32 (m, 5H), 4.68-4.84 (m, 1H), 3.25 (d, J=4.4 Hz, 1H), 2.92 (dd, J=16.3, 11.0 Hz, 1H), 1.55 (d, J=6.7 Hz, 3H); MS (ESI) m/z 338.0 (M+H)⁺.

Example 57

5'-Chloro-2,3-dimethyl-2,3,4,9-tetrahydrospiro[β-carboline-1,3'-indol]-2'(1'H)-one (44)

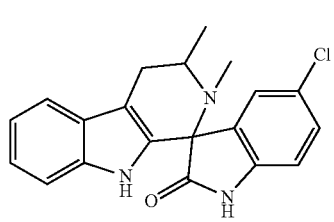

44

5'-Chloro-2,3-dimethyl-2,3,4,9-tetrahydrospiro[β-carboline-1,3'-indol]-2'(1'H)-one: ¹H NMR (300 MHz, DMSO-d₆): δ 10.68 (s, 1H), 10.32 (s, 1H), 7.43 (d, J=7.0 Hz, 1H), 7.35 (dd, J=8.4, 2.2 Hz, 1H), 7.16 (d, J=7.6 Hz, 1H), 6.91-7.07 (m, 4H), 3.74-3.89 (m, 1H), 2.85 (dd, J=15.2, 3.8 Hz, 1H), 2.51-2.62 (m, 1H), 2.09 (s, 3H), 1.24 (d, 3H); MS (ESI) m/z 352.0 (M+H)⁺.

Example 58

5'-Chloro-3,4,5,10-tetrahydro-2H-spiro[azepino[3,4-b]indole-1,3'-indol]-2'(1'H)-one (45)

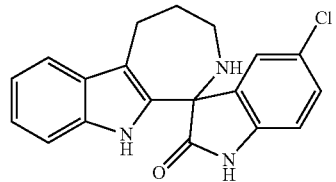

45

5'-Chloro-3,4,5,10-tetrahydro-2H-spiro[azepino[3,4-b]indole-1,3'-indol]-2'(1'H)-one: ¹H NMR (300 MHz, DMSO-d₆): δ 10.56 (s, 1H), 10.10 (s, 1H), 7.46 (d, J=7.0 Hz, 1H), 7.32 (dd, J=8.4, 2.2 Hz, 1H), 7.1-7.16 (m, 2H), 6.95 (t, J=7.8 Hz, 1H), 6.91-7.03 (m, 2H), 3.47 (ddd, J=14.2, 7.3, 5.1 Hz, 2H), 2.91-3.17 (m, 1.88-2.06 (m, 2H); MS (ESI) m/z 338.0 (M+H)⁺.

Example 59

(1R,3S)-5'-Bromo-3-methyl-2,3,4,9-tetrahydrospiro[β-carboline-1,3'-indol]-2'(1'H)-one (46)

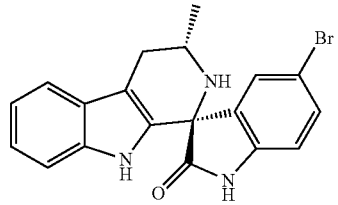

46

(1R,3S)-5'-Bromo-3-methyl-2,3,4,9-tetrahydrospiro[β-carboline-1,3'-indol]-2'(1'H)-one: ¹H NMR (300 MHz, DMSO-d₆): δ 10.46 (s, 1H), 10.42 (s, 1H), 7.44 (dd, J=8.2, 2.1 Hz, 2H), 7.11-7.21 (m, 2H), 6.92-7.07 (m, 2H), 6.88 (d, J=8.5 Hz, 1H), 3.84-3.98 (m, 1H), 2.78 (dd, J=15.1, 3.7 Hz, 1H), 2.41 (dd, J=15.1, 10.4 Hz, 1H), 1.18 (d, J=6.5 Hz, 3H); MS (ESI) m/z 383.0 (M+H)⁺; [α]²⁵$_D$ +244.9°.

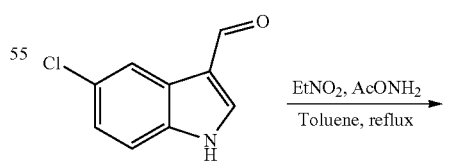

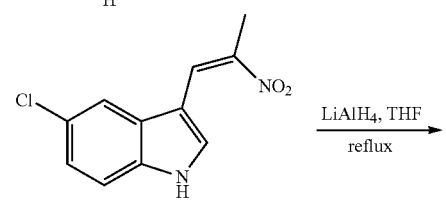

To a solution of 5-chloroindole-3-carboxaldehyde (2.14 g; 11.7 mmol) in toluene (22 mL) was added nitroethane (25.2 mL) and ammonium acetate (0.5 g, 6.5 mmol). The reaction mixture was stirred at reflux (130° C.) for 5 hours. Afterward, additional ammonium acetate (0.43 g, 5.9 mmol) was added and the reflux was continued. After an one hour, an additional amount of ammonium acetate (0.44 g, 5.9 mmol) was added. The reaction mixture was refluxed for another hour and was then left, to stand at room temperature overnight. The precipitate formed was collected by filtration, washed with toluene and placed under high vacuum to afford the nitro intermediate as bright yellow powder (2.69 g, 97.1%). $^1$HNMR (300 MHz, DMSO-$d_6$): δ 8.42 (s, 1H), 8.06 (s, 1H), 7.95 (d, J=2.05 Hz, 1H), 7.52, (d, J=9.1 Hz, 1H), 7.24 (dd, J=8.5, 2.1 Hz, 1H), 2.48 (s 3H), 1.86 (s, 2H); MS (ESI) m/z 236.0 (M+H)$^+$.

To a suspension of lithium aluminum hydride (2.62 g, 68.2 mmol) in tetrahydrofuran (70 mL) was added the nitro intermediate (2.69 g, 11.37 mmol) in small portions. The resulting reaction mixture was refluxed at 90° C. for 6 hours. Afterward, the reaction mixture was cooled to room temperature and placed in an ice bath. It was then quenched by adding a water-THF mixture (6:4, 70 mL) slowly, followed by aqueous sodium hydroxide (4 M, 70 mL). The resultant suspension was allowed to stir overnight and was then filtered through celite. The filtrate obtained was concentrated in vacuo, diluted with water and extracted with ethyl acetate. The extracts was washed with water and brine, dried by sodium sulfate and filtered. The filtrate was concentrated in vacuo and the residue was placed under high vacuum to afford 2-(5-chloro-1H-indol-3-yl)-1-methyl-ethylamine as a brown oil (2.25 g, 94.9%). $^1$HNMR (300 MHz, DMSO-$d_6$): δ 11.01 (bs, 1H), 7.55 (d, J=2.05 Hz, 1H), 7.34 (d, J=9.08 Hz, 1H), 7.20 (d, J=1.76 Hz, 1H), 7.04 (dd, J=8.5, 2.1 Hz, 1H), 2.96-3.10 (m, 1H), 2.60 (d, J=6.5 Hz, 2H), 0.97 (d, J=6.5 Hz, 3H); MS (ESI) m/z 208.0 (M+H)$^+$.

Example 60

(1R,3S)-5'-Chloro-3-methyl-3,4,5,10-tetrahydro-2H-spiro[azepino[3,4-b]indole-1,3'-indol]-2'(1'H)-one (47)

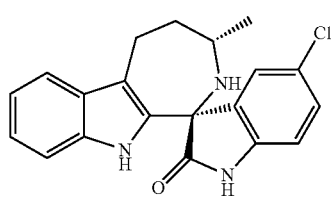

(1R,3S)-5'-Chloro-3-methyl-3,4,5,10-tetrahydro-2H-spiro[azepino[3,4-b]indole-1,3'-indol]2'(1'H)-one: $^1$H NMR (300 MHz, DMSO-$d_6$): δ 10.43 (s, 1H), 9.96 (s, 1H), 7.46 (dd, J=6.6 Hz, J==1.8 Hz, 1H), 7.32 (dd, J=8.1 Hz, J=2.4 Hz, 1H), 7.17 (m, 2H), 6.96 (m, 3H), 3.90 (m, 1H), 3.12 (m, 1H), 2.88 (m, 1H), 2.78 (d, J=5.7 Hz, 1H), 2.08 (m, 1H), 1.64 (m, 1H), 1.05 (d, J=6.3 Hz, 3H); MS (ESI) m/z 352.0 (M+H)$^+$; $[α]^{25}_D$ +238.8°.

Example 61

(1S,3R)-5'-Chloro-3-methyl-3,4,5,10-tetrahydro-2H-spiro[azepino[3,4-b]indole-1,3'-indol]-2'(1'H)-one (48)

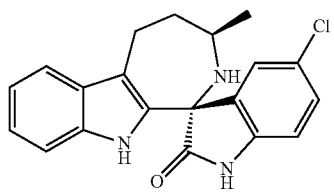

(1S,3R)-5'-Chloro-3-methyl-3,4,5,10-tetrahydro-2H-spiro[azepino[3,4-b]indole-1,3'-indol]-2'(1'H)-one: $^1$H NMR (300 MHz, DMSO-$d_6$): δ 10.43 (s, 1H), 9.96 (s, 1H), 7.46 (dd, J=6.6 Hz, J=1.5 Hz, 1H), 7.33 (dd, J=8.1 Hz, J=2.4 Hz, 1H), 7.17 (m, 2H), 6.96 (m, 3H), 3.90 (m, 1H), 3.12 (m, 1H), 2.88 (m, 1H), 2.78 (d, J=5.4 Hz, 1H), 2.08 (m, 1H), 1.64 (m, 1H), 1.05 (d, J=6.3 Hz, 3H); MS (ESI) m/z 352.0 (M+H)$^+$; $[α]^{25}_D$ −237.6°.

Example 62

(1R,3S)-5',6-Dichloro-3-methyl-2,3,4,9-tetrahydrospiro[β-carboline-1,3'-indol]-2'(1'H)-one (49)

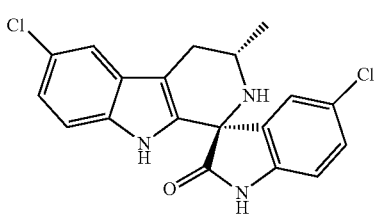

(1R,3S)-5',6-Dichloro-3-methyl-2,3,4,9-tetrahydrospiro[β-carboline-1,3'-indol]-2'(1'H)-one: $^1$H NMR (300 MHz, DMSO-$d_6$): δ 10.66 (s, 1H), 10.50 (s, 1H), 7.47 (d, J=2.1 Hz, 1H), 7.32 (dd, J=8.1 Hz, J=2.1 Hz, 1H), 7.17 (d, J=8.4 Hz, 1H), 7.04 (m, 2H), 6.93 (d, J=8.4 Hz, 1H), 3.92 (m, 1H), 3.10 (d, J=5.7 Hz, 1H), 2.78 (m, 1H), 2.39 (m, 1H), 1.17 (d, J=6.3 Hz, 3H); MS (ESI) m/z 373.0 (M+H)$^+$; $[α]^{25}_D$ +141.2°.

Example 63

(1S,3R)-5',6-Dichloro-3-methyl-2,3,4,9-tetrahydrospiro[β-carboline-1,3'-indol]-2'(1'H)-one (50)

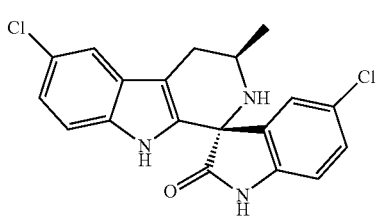

(1S,3R)-5',6-Dichloro-3-methyl-2,3,4,9-tetrahydrospiro[β-carboline-1,3'-indol]-2'(1'H)-one: $^1$H NMR (300 MHz, DMSO-d$_6$): δ 10.66 (s, 1H), 10.49 (s, 1H), 7.48 (d, J=2.1 Hz, 1H), 7.32 (dd, J=8.1 Hz, J=2.4 Hz, 1H), 7.17 (d, J=8.4 Hz, 1H), 7.03 (m, 2H), 6.93 (d, J=8.1 Hz, 1H), 3.92 (m, 1H), 3.11 (m, 1H), 2.78 (m, 1H), 2.39 (m, 1H), 1.17 (d, J=6.3 Hz, 3H); MS (ESI) m/z 373.0 (M+H)$^+$; $[α]^{25}_D$ −171.2°.

Example 64

(1R,3S)-5'-Chloro-6-fluoro-3-methyl-2,3,4,9-tetrahydrospiro[β-carboline-1,3'-indol]-2'(1'H)-one (51)

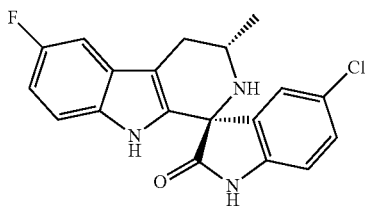

(1R,3S)-5'-Chloro-6-fluoro-3-methyl-2,3,4,9-tetrahydrospiro[β-carboline-1,3'-indol]-2'(1'H)-one: $^1$H NMR (500 MHz, DMSO-d6) δ 10.53 (s, 1H), 10.48 (s, 1H), 7.32 (dd, 1H, J=8.3, 2.2 Hz), 7.20 (dd, 1H, J=9.8, 2.3 Hz), 7.16 (dd, 1H, J=8.8, 4.6 Hz), 7.06 (d, 1H, J=1.5 Hz), 6.93 (d, 1H, J=6.0 Hz), 6.87 (dt, 1H, J=6.9, 1.8 Hz), 3.95 (m, 1H), 3.35 (bs, 1H), 2.77 (dd, 1H, J=15.0, 3.7 Hz), 2.40 (dd, 1H, J=15.0, 10.6 Hz), 1.18 (d, 3H, J=6.4 Hz); HRMS: 355.0890 (M+) calculated for C$_{19}$H$_{15}$ClFN$_3$O; $[α]^{25}_D$ +211.6°.

Example 65

(1S,3R)-5'-Chloro-6-fluoro-3-methyl-2,3,4,9-tetrahydrospiro[β-carboline-1,3'-indol]-2'(1'H)-one (52)

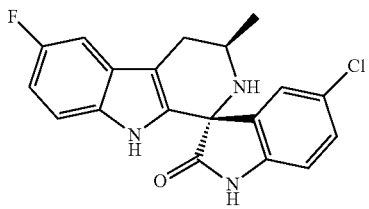

(1S,3R)-5'-Chloro-6-fluoro-3-methyl-2,3,4,9-tetrahydrospiro[β-carboline-1,3'-indol]-2'(1'H)-one: $^1$H NMR (300 MHz, DMSO-d6): δ 10.55 (s, 1H), 10.51 (s, 1H), 7.32 (dd, J=8.4 Hz, J=2.4 Hz, 1H), 7.20 (dd, J=10.1 Hz, J=2.4 Hz, 1H), 7.14 (dd, J=8.8 Hz, J=4.5 Hz, 1H), 7.05 (d, J=2.4 Hz, 1H), 6.93 (d, J=8.4 Hz, 1H), 6.86 (td, J=9.3 Hz, J=2.4 Hz, 1H), 3.93 (m, 1H), 2.76 (dd, J=15.0 Hz, J=3.6 Hz, 1H), 2.39 (dd, J=15.2 Hz, J=10.5 Hz, 1H), 1.17 (d, J=6.3 Hz, 3H); MS (ESI) m/z 357.0 (M+H)$^+$; $[α]_D$ −208.8°.

Example 66

5'-Chloro-3-propyl-2,3,4,9-tetrahydrospiro[β-carboline-1,3'-indol]-2'(1'H)-one (53)

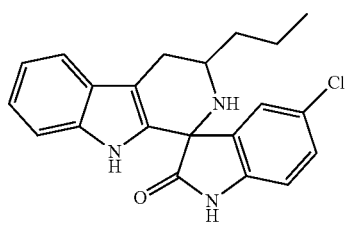

5'-Chloro-3-propyl-2,3,4,9-tetrahydrospiro[β-carboline-1,3'-indol]-2'(1'H)-one: $^1$H NMR (300 MHz, DMSO-d$_6$): δ 10.45 (s, 1H), 10.40 (s, 1H), 7.44 (d, J=7.5 Hz, 1H), 7.31 (dd, J=8.4 Hz, J=2.1 Hz, 1H), 7.16 (d, J=7.5 Hz, 1H), 6.98 (m, 4H), 3.79 (m, 1H), 2.80 (dd, J=15.0 Hz, J=3.6 Hz, 1H), 2.40 (m, 1H), 1.46 (m, 4H), 0.91 (t, J=6.9 Hz, 1H); MS (ESI) m/z 366.0 (M+H)$^+$.

The following trifluoromethyl compounds can be prepared according to the following scheme.

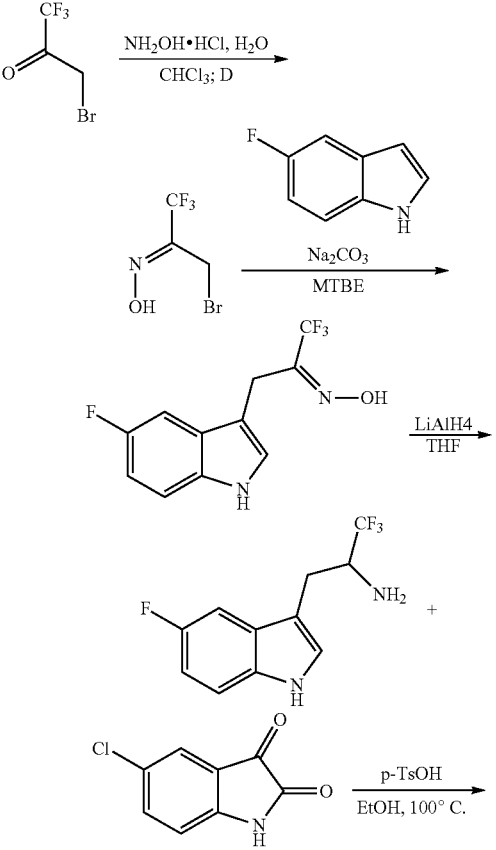

-continued

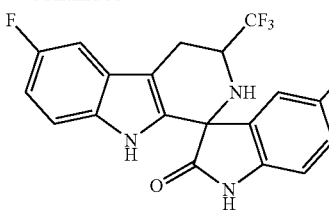

Example 67

3-Bromo-1,1,1-trifluoro-propan-2-one oxime

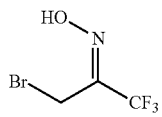

To a solution of 1-promo-3,3,3-trifluoropropan-2-one in 15 mL of chloroform (passed through a pad of basic alumina) was added a solution of hydroxylamine hydrochloride in 2.5 mL of water and the mixture heated to reflux. After 25 hours, the reaction mixture was cooled and 15 mL of $H_2O$ was added. The layers were separated and the aqueous layer was washed with 3×15 mL dichloromethane. The combined organic extracts were dried over magnesium sulfate, filtered and concentrated in vacuo. Note: As the product is a volatile liquid, excessive application of the vacuum to remove the co-solvent reduced the yield of the product, it's the product was used without further purification.

Example 68

1,1,1-Trifluoro-3-(5-fluoro-1H-inol-3-yl)-propan-2-one oxime

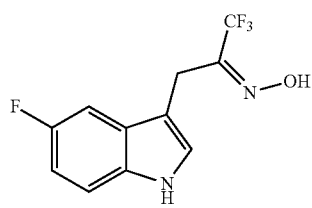 [SMILES: O/N=C(/Cc1c[nH]c2ccc(F)cc12)C(F)(F)F]

To a solution of 362.5 mg of 3-bromo-1,1,1-trifluoro-propan-2-one oxime in 20 mL of MTBE was added 5-fluoroindole and sodium carbonate and the mixture stirred at room temperature. After 2 hours, the reaction was filtered through celite and concentrated in vacuo. The residue was purified on silica gel (hexane:ethyl acetate from 0% to 30% ethyl acetate) to provide the desired product. $^1$H NMR (300 MHz, DMSO-$d_6$): δ 11.00 (bs, 1H) 7.32 (m, 3H) 6.91 (td, J=9.2, 2.4 Hz, 1H) 3.48 (m, 1H) 3.02 (dd, J=14.5, 3.2 Hz, 1H) 2.70 (dd, J=14.5, 9.6 Hz, 1H), 1.84 (bs, 2H); MS (ESI) m/z 247.0 (M+H)$^+$.

Example 69

2,2,2-Trifluoro-4-(5-fluoro-1H-indol-3-ylmethyl) ethylamine

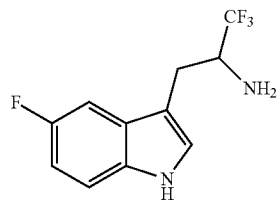 [SMILES: NC(Cc1c[nH]c2ccc(F)cc12)C(F)(F)F]

To a solution of 280 mg of 1,1,1-trifluoro-3-(5-fluoro-1H-inol-3-yl)-propan-2-one oxime in diethyl ether was added 5 mL of 2M lithium aluminium hydride in THF dropwise at 0° C. The reaction was stirred at 0° C., then warmed to room temperature. After, 21 hours, the reaction was carefully quenched with water until no effervescence was observed. The mixture was then dried over magnesium sulfate, filtered through celite and concentrated to dryness. The residue was purified on silica gel (100% hexane to 65-70% hexane in ethyl acetate).

Example 70

(1S,3R)-5'-Chloro-3-(trifluoromethyl)-2,3,4,9-tetrahydrospiro[β-carboline-1,3'-indol]2'(1'H)-one (54)

54

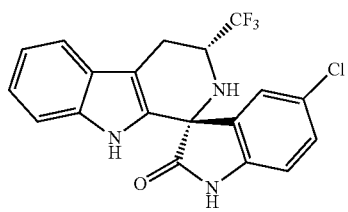

(1S,3R)-5'-Chloro-3-(trifluoromethyl)-2,3,4,9-tetrahydrospiro[β-carboline-1,3'-indol]-2'(1'H)-one: $^1$H NMR (300 MHz, DMSO-$d_6$): δ11.01 (s, 1H), 10.78 (s, 1H), 7.54 (m, 2H), 7.35 (dd, J=8.7, 2.1 Hz, 1H), 7.120 (m, 1H), 7.08 (td, J=7.5, 1.5 Hz, 1H), 7.01 (m, 2H), 4.36 (m, 1H), 3.13 (dd, J=15.0, J=3.9 Hz, 1H), 2.85 (dd, J=15.0, J=11.1 Hz, 1H), 2.54 (d, J=11.7 Hz, 1H); MS (ESI) m/z 392.0 (M+H)$^+$.

Example 71

(1R,3R)-5'-Chloro-3-(trifluoromethyl)-2,3,4,9-tetrahydrospiro[β-carboline-1,3'-indol]-2'(1'H)-one (55)

55

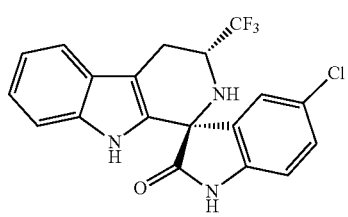

(1R,3R)-5'-Chloro-3-(trifluoromethyl)-2,3,4,9-tetrahydrospiro[β-carboline-1,3'-indol]-2'(1'H)-one: $^1$H NMR (300 MHz, DMSO-$d_6$): δ 10.70 (s, 1H), 10.62 (s, 1H), 7.53 (d, J=7.5 Hz, 1H), 7.38 (dd, J=8.4, 2.4 Hz, 1H), 7.30 (d, J=2.1 Hz, 1H), 7.21 (m, 1H), 7.08 (td, J=7.2, 1.2 Hz, 1H), 7.00 (m, 2H), 4.62 (m, 1H), 3.75 (d, J=9.0 Hz, 1H), 2.98 (m, 2H); MS (ESI) m/z 392.0 (M+H)$^+$; [α]$^{25}_D$ +274.5°.

Example 72

(1R,3S)-5'-Chloro-3-(trifluoromethyl)-2,3,4,9-tetrahydrospiro[β-carboline-1,3'-indol]-2'(1'H)-one (56)

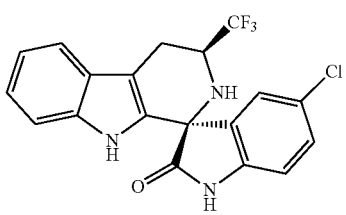

56

(1R,3S)-5'-Chloro-3-(trifluoromethyl)-2,3,4,9-tetrahydrospiro[β-carboline-1,3'-indol]-2'(1'H)-one: $^1$H NMR (300 MHz, DMSO-d6): δ 11.01 (s, 1H), 10.78 (s, 1H), 7.54 (m, 2H), 7.35 (dd, J=8.6 Hz, J=2.3 Hz, 1H), 7.20 (m, 1H), 7.082 (td, J=7.6 Hz, J=1.3 Hz, 1H), 7.01 (m, 2H), 4.36 (m, 1H), 3.13 (dd, J=15.0 Hz, J=3.9 Hz, 1H), 2.85 (dd, J=15.2 Hz, J=11.0 Hz, 1H), 2.54 (m, 1H); MS (ESI) m/z 392.0 (M+H)$^+$.

Example 73

(1S,3S)-5'-Chloro-3-(trifluoromethyl)-2,3,4,9-tetrahydrospiro[β-carboline-1,3'-indol]-2'(1'H)-one (57)

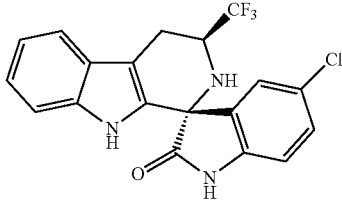

57

(1S,3S)-5'-Chloro-3-(trifluoromethyl)-2,3,4,9-tetrahydrospiro[β-carboline-1,3'-indol]-2'(1'H)-one: $^1$H NMR (300 MHz, DMSO-d6): δ 10.69 (s, 1H) 10.62 (s, 1H), 7.53 (d, J=7.8 Hz, 1H), 7.38 (dd, J=8.3, 2.3 Hz, 1H), 7.29 (d, J=2.4 Hz, 1H), 7.20 (d, J=7.1 Hz, 1H), 7.08 (td, J=8.0 Hz, 1.0 Hz, 1H) 7.00 (m, 2H), 4.61 (m, 1H), 3.74 (d, J=9.1 Hz, 1H), 2.97 (m, 2H); MS (ESI) m/z 392.0 (M+H)$^+$; [α]$^{25}_D$ −295.4°.

Example 74

5'-Chloro-6-fluoro-3-methyl-2,3,4,9-tetrahydrospiro[β-carboline-1,3'-indol]-2'(1'H)-one (58)

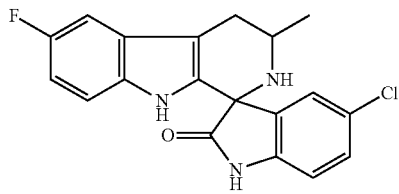

58

5'-Chloro-6-fluoro-3-methyl-2,3,4,9-tetrahydrospiro[β-carboline-1,3'-indol]-2'(1'H)-one: $^1$H NMR (300 MHz, DMSO-d$_6$): δ 10.53 (s, 1H), 10.47 (s, 1H), 7.32 (dd, J=1.8, 8.4 Hz, 1H), 7.19 (dd, J=2.4, 9.9 Hz, 1H), 7.13 (dd, J=4.5, 8.9 Hz, 1H), 7.04 (d, J=1.8 Hz, 1H), 6.92 (d, J=8.1 Hz, 1H), 6.85 (td, J=2.7, 8.9 Hz, 1H), 3.98-3.83 (m, 1H), 2.76 (dd, J=3.9, 14.9 Hz, 1H), 2.38 (dd, J=10.2, 15.2 Hz, 1H), 1.17 (d, J=5.1 Hz, 3H); MS (ESI) m/z 356.0 (M+H)$^+$.

Example 75

5,5'-Dichloro-3-methyl-2,3,4,9-tetrahydrospiro[β-carboline-1,3'-indol]-2'(1'H)-one (59)

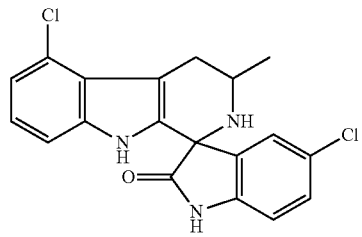

59

5,5'-Dichloro-3-methyl-2,3,4,9-tetrahydrospiro[β-carboline-1,3'-indol]-2'(1'H)-one: $^1$H NMR (300 MHz, DMSO-d$_6$): δ 10.79 (s, 1H), 10.50 (s, 1H), 7.32 (dd, J=2.4, 8.3 Hz, 1H), 7.12 (dd, J=2.7, 6.0 Hz, 1H), 7.04 (d, J=2.1 Hz, 1H), 6.98 (d, J=3.6 Hz, 1H), 6.96 (s, 1H), 6.92 (d, J=8.4 Hz, 1H), 3.98-3.86 (m, 1H), 3.19 (dd, J=3.9, 15.3 Hz, 1H), 2.61 (dd, J=10.5, 15.5 Hz, 1H), 1.17 (d, J=6.6 Hz, 3H); MS (ESI) m/z 373.0 (M+H)$^+$.

Example 76

5',7-Dichloro-3-methyl-2,3,4,9-tetrahydrospiro[β-carboline-1,3'-indol]-2'(1'H)-one (60)

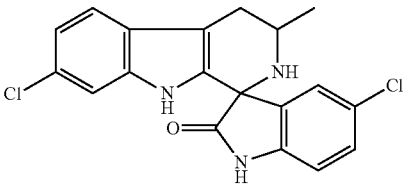

60

5',7-Dichloro-3-methyl-2,3,4,9-tetrahydrospiro[β-carboline-1,3'-indol]-2'(1'H)-one: $^1$H NMR (300 MHz, DMSO-d$_6$): δ 10.79 (s, 1H), 10.50 (s, 1H), 7.45 (d, J=8.1 Hz, 1H), 7.32 (dd, J=2.4, 8.1 Hz, 1H), 7.17 (d, J=1.5 Hz, 1H), 7.04 (d, J=2.1 Hz, 1H), 6.98 (dd, J=1.8, 8.4 Hz 1H), 6.93 (d, J=8.4 Hz, 1H), 3.98-3.84 (m, 1H), 2.78 (dd, J=3.9, 15.2 Hz, 1H), 2.39 (dd, J=10.8, 15.0 Hz, 1H), 1.17 (d, J=6.3 Hz, 3H); MS (ESI) m/z 373.0 (M+H)$^+$.

Example 77

5',8-Dichloro-3-methyl-2,3,4,9-tetrahydrospiro[β-carboline-1,3'-indol]-2'(1'H)-one (61)

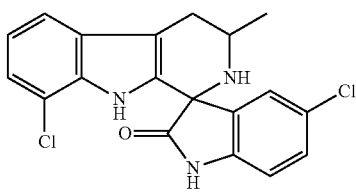

61

5',8-Dichloro-3-methyl-2,3,4,9-tetrahydrospiro[β-carboline-1,3'-indol]-2'(1'H)-one: $^1$H NMR (300 MHz, DMSO-d$_6$): δ 10.93 (s, 1H), 10.42 (s, 1H), 7.44 (d, J=7.8 Hz, 1H), 7.32 (dd, J=2.4, 8.4 Hz, 1H), 7.11 (dd, J=0.9, 7.5 Hz, 1H), 6.99 (s, 1H), 6.99 (dd, J=6.3, 8.7 Hz, 1H), 6.89 (d, J=8.4 Hz, 1H), 3.90-3.76 (m, 1H), 2.80 (dd, J=3.9, 15.0 Hz, 1H), 2.43 (dd, J=10.5, 15.0 Hz, 1H), 1.16 (d, J=6.6 Hz, 3H); MS (ESI) m/z 373.0 (M+H)$^+$.

Example 78

5'-Chloro-3,6-dimethyl-2,3,4,9-tetrahydrospiro[β-carboline-1,3'-indol]-2'(1'H)-one (62)

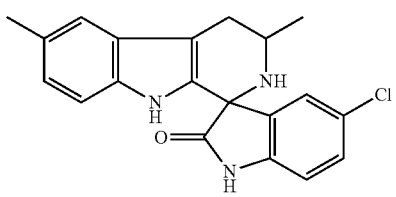

62

5'-Chloro-3,6-dimethyl-2,3,4,9-tetrahydrospiro[β-carboline-1,3'-indol]-2'(1'H)-one: $^1$H NMR (300 MHz, DMSO-d$_6$): δ 10.43 (s, 1H), 10.26 (s, 1H), 7.30 (dd, J=8.4, 2.4 Hz, 1H), 7.21 (s, 1H), 7.04 (d, J=8.1 Hz, 1H), 7.01 (d, J=2.4 Hz, 1H), 6.91 (d, J=8.4 Hz 1H), 6.84 (dd, J=8.3, 1.5 Hz, 1H), 3.98-3.85 (m, 1H), 2.74 (dd, J=14.9, 3.6 Hz, 1H), 2.38 (dd, J=15.2, 10.5 Hz, 1H), 2.36 (s, 3H), 1.17 (d, J=6.6 Hz, 3H); MS (ESI) m/z 352.0 (M+H)$^+$.

Example 79

6-Bromo-5'-chloro-3-methyl-2,3,4,9-tetrahydrospiro[β-carboline-1,3'-indol]-2'(1'H)-one (63)

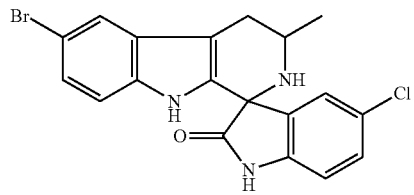

63

6-Bromo-5'-chloro-3-methyl-2,3,4,9-tetrahydrospiro[β-carboline-1,3'-indol]-2'(1'H)-one: $^1$H NMR (300 MHz, DMSO-d$_6$): δ 10.67 (s, 1H), 10.49 (s, 1H), 7.61 (s, 1H), 7.32 (dd, J=8.3, 2.1 Hz, 1H), 7.13 (s, 1H), 7.12 (s, 1H), 7.03 (d, J=2.1 Hz, 1H), 6.92 (d, J=8.1 Hz, 1H), 3.98-3.84 (m, 1H), 2.78 (dd, J=15.2, 3.6 Hz, 1H), 2.38 (dd, J=15.3, 10.5 Hz, 1H), 1.17 (d, J=6.3 Hz, 3H); MS (ESI) m/z 417.0 (M+H)$^+$.

Example 80

5'-Chloro-6-methoxy-3-methyl-2,3,4,9-tetrahydrospiro[β-carboline-1,3'-indol]-2'(1'H)-one (64)

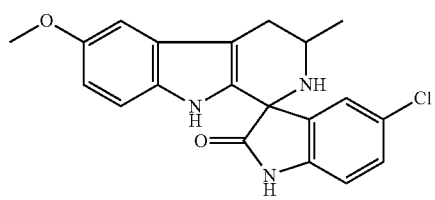

64

5'-Chloro-6-methoxy-3-methyl-2,3,4,9-tetrahydrospiro[β-carboline-1,3'-indol]-2'(1'H)-one: $^1$H NMR (300 MHz, DMSO-d$_6$): δ 10.43 (s, 1H), 10.23 (s, 1H), 7.30 (dd, J=8.3, 2.4 Hz, 1H), 7.04 (d, J=11.4 Hz, 1H), 7.03 (s, 1H), 6.93 (d, J=2.4 Hz, 1H), 6.91 (d, J=8.1 Hz, 1H), 6.66 (dd, J=2.4, 8.6 Hz, 1H), 3.98-3.86 (m, 1H), 3.75 (s, 3H), 2.75 (dd, J=14.9, 3.6 Hz, 1H), 2.38 (dd, J=15.2, 10.2, Hz 1H), 1.17 (d, J=6.6 Hz, 3H); MS (ESI) in/368.0 (M+H)$^+$.

Example 81

5'-Chloro-6-hydroxy-3-methyl-2,3,4,9-tetrahydrospiro[β-carboline-1,3'-indol]-2'(1'H)-one (65)

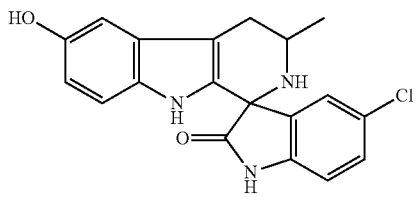

65

Compound 65 can be prepared according to the following procedure.

To a solution of 64 (157 mg, 0.428 mmol) in 12 mL DCM was added boron trichloride (1M in dichloromethane) (2.14 mL, 2.14 mmol) cautiously in an ice bath. Additional aliquots of boron trichloride were added after the three, six and eight hours. After the last addition, the reaction was left to stir at room temperature for 18 hours. Upon completion, the reaction was quenched with sat NaHCO₃. The mixture was washed with dichloromethane, followed by EtOAc. The organic layers were combined then dried with sodium sulfate, filtered and concentrated in vacuo. The product was isolated by flash column chromatography with the gradient 1-3% MeOH in dichloromethane to provide 65 (100 mg, 66).

5'-Chloro-6-hydroxy-3-methyl-2,3,4,9-tetrahydrospiro[β-carboline-1,3'-indol]-2'(1'H)-one: ¹H NMR (300 MHz, DMSO-d₆): δ 10.42 (s, 1H), 10.06 (s, 1H), 8.58 (s, 1H), 7.30 (dd, J=8.3, 2.4 Hz, 1H), 7.01 (d, J=2.4 Hz, 1H), 6.94 (d, J=9.0 Hz, 1H), 6.90 (d, J=8.4 Hz, 1H), 6.73 (d, J=2.4 Hz, 1H), 6.53 (dd, J=8.7, 2.4 Hz, 1H), 3.98-3.84 (m, 1H), 2.66 (dd, J=14.9, 3.6 Hz, 1H), 2.33 (dd, J=15.0, 10.5 Hz, 1H), 1.16 (d, J=6.6 Hz, 3H); MS (ESI) m/z 354 (M+H)⁺.

Example 82

(1R,3S)-5'-Chloro-6-hydroxy-3-methyl-2,3,4,9-tetrahydrospiro[β-carboline-1,3'-indol]-2'(1'H)-one (66)

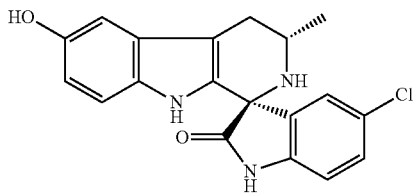

66

(1R,3S)-5'-Chloro-6-hydroxy-3-methyl-2,3,4,9-tetrahydrospiro[β-carboline-1,3'-indol]-2'(1'H)-one: ¹H NMR, (500 MHz, DMSO-d₆): δ 10.44 (s, 1H), 10.08 (s, 1H), 8.61 (s, 1H), 7.32 (d, J=8.0 Hz, 1H), 7.05 (s, 1H), 6.96 (d, J=8.5 Hz, 1H), 6.92 d, J=8.5 Hz, 1H), 6.75 (s, 1H), 6.56 (d, J=8.5 Hz, 1H), 3.93 (m, 1H), 2.69 (d, J=14.0 Hz, 1H), 2.35 (m, 1H), 1.18 (d, J=5.3 Hz, 3H); MS (ESI) m/z 353.9 (M+H)⁺; [α]²⁵_D: +204.0°.

Example 83

(1S,3R)-5'-Chloro-6-hydroxy-3-methyl-2,3,4,9-tetrahydrospiro[β-carboline-1,3'-indol]-2'(1'H)-one (67)

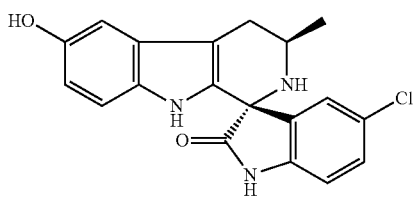

67

(1S,3R)-5'-Chloro-6-hydroxy-3-methyl-2,3,4,9-tetrahydrospiro[β-carboline-1,3'-indol]-2'(1'H)-one: ¹H NMR (500 MHz, DMSO-d₆): δ 10.42 (s, 1H), 10.07 (s, 1H), 8.59 (s, 1H), 7.31 (d, J=7.5 Hz, 1H), 7.03 (s, 1H), 6.96 (d, J=8.5 Hz, 1H), 6.91 (d, J=8.0 Hz, 1H), 6.74 (s, 1H), 6.55 (d, J=8.5 Hz, 1H), 3.92 (m, 1H), 2.68 (d, J=14.3 Hz, 1H), 2.35 (m, 1H), 1.17 (d, J=5.2 Hz, 3H); MS (ESI) m/z 353.9 (M+H)⁺; [α]²⁵_D: −197.6°.

Example 84

5'-Chloro-7-methoxy-3-methyl-2,3,4,9-tetrahydrospiro[β-carboline-1,3'-indol]-2'(1'H)-one (68)

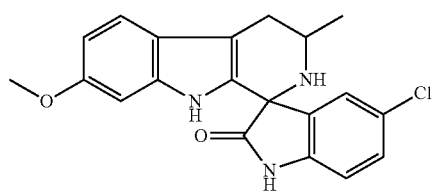

68

5'-Chloro-7-methoxy-3-methyl-2,3,4,9-tetrahydrospiro[β-carboline-1,3'-indol]-2'(1'H)-one: 1H NMR (500 MHz, CDCl₃): δ 8.51 (bs, 1H), 7.46 (bs, 1H), 7.40 (d, J=8.6 Hz, 1H), 7.14 (dd, J=8.3, 2.1 Hz, 1H), 7.10 (d, J=2.1 Hz, 1H), 6.77 (dd, J=8.7, 2.2 Hz, 1H), 6.69 (d, J=8.5 Hz, 1H), 6.67 (d, J=2.2 Hz, 1H), 4.16 (m, 1H), 3.75 (s, 3H), 2.93 (dd, J=15.5, 3.9 Hz, 1H), 2.52 (dd, J=15.4, 10.5 Hz, 1H), 1.28 (d, J=6.4 Hz, 3H); MS (ESI) m/z 368.0 (M)⁺.

Example 85

5'-Chloro-7-hydroxy-3-methyl-2,3,4,9-tetrahydrospiro[β-carboline-1,3'-indol]-2'(1'H)-one (69)

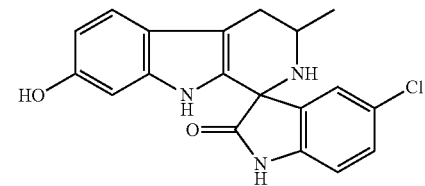

69

5'-Chloro-7-hydroxy-3-methyl-2,3,4,9-tetrahydrospiro[β-carboline-1,3'-indol]-2'(1'H)-one: ¹H NMR (500 MHz, DMSO-d₆): δ 10.41 (s, 1H), 10.00 (s, 1H), 8.80 (s, 1H), 7.31 (bd, J=7.0 Hz, 1H), 7.19 (bd, J=8.0 Hz, 1H), 7.03 (s, 1H), 6.91 (bd, J=8.5 Hz, 1H), 6.56 (s, 1H), 6.49 (bd, J=8.0 Hz, 1H), 3.90 (bs, 1H), 2.96 (bs, 1H), 2.70 (bd, J=14.2 Hz, 1H), 2.36 (bt, J=9.8 Hz, 1H), 1.17 (bs, 3H); MS (ESI) m/z 352.1 (M)⁺.

Example 86

(1R,3S)-5'-Chloro-7-hydroxy-3-methyl-2,3,4,9-tetrahydrospiro[β-carboline-1,3'-indol]-2'(1'H)-one (70)

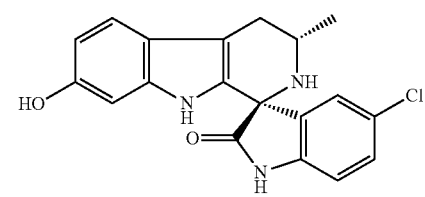

70

(1R,3S)-5'-Chloro-7-hydroxy-3-methyl-2,3,4,9-tetrahydrospiro[β-carboline-1,3'-indol]-2'(1'H)-one: $^1$H NMR (500 MHz, DMSO-d$_6$): δ 10.41 (s, 1H), 10.00 (s, 1H), 8.80 (s, 1H), 7.31 (d, J=8.0 Hz, 1H), 7.19 (d, J=8.0 Hz, 1H), 7.03 (s, 1H), 6.91 (d, J=8.0 Hz, 1H), 6.56 (s, 1H), 6.49 (d, J=8.5 Hz, 1H), 3.90 (bs, 1H), 2.96 (bs, 1H), 2.70 (bd, J=14.4 Hz, 1H), 2.36 (bt, J=12.2 Hz, 1H), 1.18 (d, J=6.4 Hz, 3H); MS (ESI) m/z 352.0 (M)$^+$; [α]$^{25}_D$: 203.2°.

Example 87

(1S,3R)-5'-Chloro-7-hydroxy-3-methyl-2,3,4,9-tetrahydrospiro[β-carboline-1,3'-indol]-2'(1°H)-one (71)

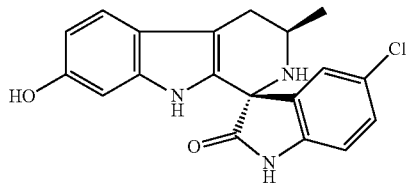

71

(1S,3R)-5'-Chloro-7-hydroxy-3-methyl-2,3,4,9-tetrahydrospiro[β-carboline-1,3'-indol]-2'(1'H)-one: $^1$H NMR (500 MHz, DMSO-d$_6$): δ 10.41 (s, 1H), 10.00 (s, 1H), 8.81 (s, 1H), 7.31 (bd, J=6.5 Hz, 1H), 7.19 (d, J=8.5 Hz, 1H), 7.03 (bs, 1H), 6.91 (bd, J=7.0 Hz, 1H), 6.56 (s, 1H), 6.49 (d, J=8.0 Hz, 1H), 3.90 (bs, 1H), 2.96 (bs, 1H), 2.70 (bd, J=13.2 Hz, 1H), 2.36 (bs, 1H), 1.18 (d, J=6.6 Hz, 3H); MS (ESI) m/z 352.1 (M)$^+$; [α]$^{25}_D$: −228.1°.

Example 88

5'-Chloro-3-methyl-6-(trifluoromethyl)-2,3,4,9-tetrahydrospiro[β-carboline-1,3'-indol]-2'(1'H)-one (72)

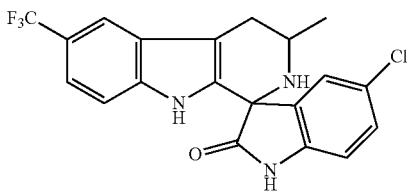

72

5'-Chloro-3-methyl-6-(trifluoromethyl)-2,3,4,9-tetrahydrospiro[β-carboline-1,3'-indol]-2'(1'H)-one: $^1$H NMR (300 MHz, DMSO-d$_6$): δ 10.96 (s, 1H), 10.52 (s, 1H), 7.82 (s, 1H), 7.38-7.29 (m, 3H), 7.04 (d, J=2.1 Hz, 1H), 6.94 (d, J=8.7 Hz, 1H), 4.01-3.83 (m, 1H), 2.88 (dd, J=15.0, 3.3 Hz, 1H), 2.44 (dd, J=15.3, 10.5 Hz, 1H), 1.18 (d, J=6.3 Hz, 3H); MS (ESI) m/z 406.0 (M+H)$^+$.

Example 89

5'-Chloro-3-methyl-2'-oxo-1',2,2',3,4,9-hexahydrospiro[β-carboline-1,3'-indole]-6-carbonitrile (73)

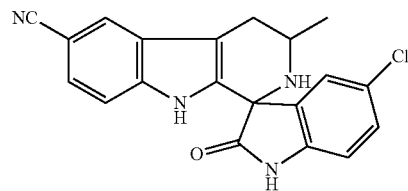

73

5'-Chloro-3-methyl-2'-oxo-1',2,2',3,4,9-hexahydrospiro[β-carboline-1,3'-indol]-6-carbonitrile: Compound 63 (30 mg, (1072 mmol), CuCN (9.67 mg, 0.108 mmol) in N-methylpyrrolidone (0.12 mL) was refluxed for 16 hr. The solvent was removed under reduced pressure overnight and the black residue was stirred for 30 minutes with 30% aq. ammonia (0.2 mL), followed by addition of chloroform. An insoluble material was tittered off and washed 5 times with boiling chloroform. The organic phases were combined, washed with water and dried with sodium sulfate. The product was isolated using flash column chromatography with 10% 35% EtOAc in hexane (3.0 mg, 11.5%). $^1$H NMR (300 MHz, DMSO-d$_6$): δ 11.11 (s, 1H), 10.54 (s, 1H), 7.99 (s, 1H), 7.92-7.83 (m, 3H), 7.05 (d, J=2.1 Hz, 1H), 6.94 (d, J=8.4 Hz, 1H), 3.98-3.85 (m, 1H), 2.85 (dd, J=15.5, 3.6 Hz, $^1$H), 2.42 (dd, J=15.3, 10.5 Hz, 1H), 1.18 (d, J=6.9 Hz, 3H); MS (ESI) m/z 363.0 (M+H)$^+$.

Example 90

(1R,3S)-5'-Chloro-3,9-dimethyl-2,3,4,9-tetrahydrospiro[β-carboline-1,3'-indol]-2'(1'H)-one (74)

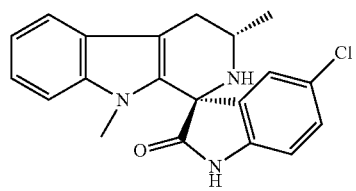

74

The following scheme was used to prepare Compound 74.

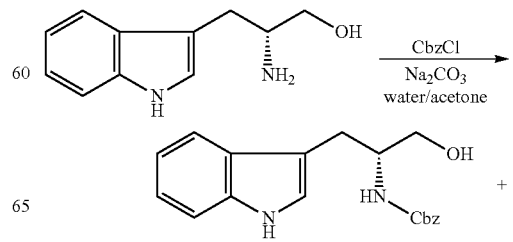

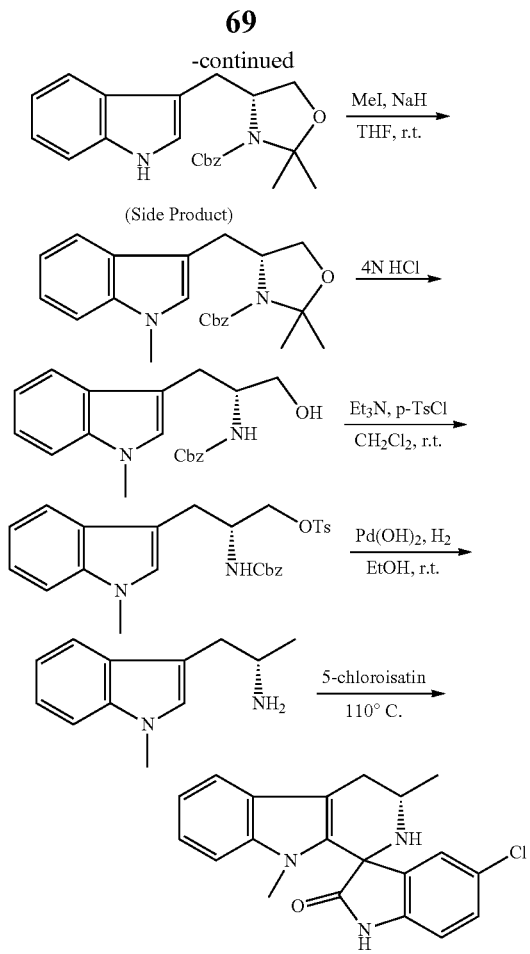

Synthetic Scheme of 74

The acetonide starting material was a side product obtained from the Cbz protection of D-tryptophanol. D-Tryptophanol (500 mg, 2.27 mmol) was dissolved in a mixture of 11.3 mL water and 11.3 mL acetone. Sodium carbonate (482 mg, 3.92 mmol) was added to the stirred, ice-cooled mixture followed by dropwise addition of benzyl chloroformate (0.374 mL, 2.29 mmol). The cooling bath was removed and the reaction was stirred at room temperature for 1.5 hours. The reaction mixture was acidified to pH 2 with concentrated HCl and diluted with of water. The aqueous mixture was extracted with EtOAc. The combined organics were then dried with magnesium sulfate, filtered and concentrated in vacuo. The side product was isolated using flash column chromatography with the gradient 0-20% EtOAc in hexane followed by 20% EtOAc in hexane.

To a stirring solution of the acetonide side product (1.5 g, 4.12 mmol) in 20.6 mL dry THF was added sodium hydride (197.6 mg, 4.94 mmol) followed by methyl iodide (0.513 mL, 8.23 mmol). The reaction mixture was stirred at room temperature for 16 hours. Upon removal of THF, the residue was taken up in EtOAc and this organic layer was washed with saturated sodium chloride. The aqueous layer was backwashed with an additional 20 mL EtOAc. The combined organics were dried with sodium sulfate, filtered and concentrated in vacuo. The product was isolated using flash column chromatography with 5-10% EtOAc in hexane followed by 10-30% EtOAc in hexane. (728.5 mg, 47%)

The N-methylated intermediate (700 mg, 1.85 mmol) was dissolved in 6.2 mL dry dichloromethane. 4N HCl in 1,4-dioxane (4.63 mL, 18.5 mmol) was added to the mixture. The reaction was stirred at room temperature for 16 hours. The reaction was concentrated in vacuo and the residue was taken up in dichloromethane. The organic layer was washed with saturated sodium chloride. The organic layer was dried with sodium sulfate, filtered and concentrated in vacuo. The product was isolated using flash column chromatography with 20% EtOAc in hexane, followed by gradient 20-50% EtOAc in hexane (305.7 mg, 49%)

A solution of the acetonide deprotected intermediate (300 mg, 0.888 mop and triethylamine (0.24 mL, 1.73 mmol) in anhydrous dichloromethane (2.5 mL) was cooled to 0° C. p-Toluenesulfonyl chloride (179 mg, 0.941 mmol) was added and the solution was stirred at room temperature for 18 hours. The reaction mixture was concentrated in vacuo. The product was isolated using flash column chromatography with 10-30% EtOAc in hexane, to provide ~400 mg of product.

The tosylate (400 mg, 0.813 mmol), was dissolved in 24.2 mL absolute ethanol and 48.8 mg palladium (II) hydroxide catalyst was added. The reaction mixture was stirred at room temperature for 2 hours. The catalyst was filtered through celite and the filtrate was concentrated in vacuo, 1M NaOH was added to the residue and the aqueous layer was extracted twice with EtOAc. The combined organics were dried with sodium sulfate, filtered and concentrated in vacuo. The residue was then dissolved in 1M NaOH and the aqueous layer was extracted twice with EtOAc. The combined organic layers were dried with sodium sulfate, filtered and concentrated in vacuo. (132.5 mg, 87%)

(1R,3S)-5'-Chloro-3,9-dimethyl-2,3,4,9-tetrahydrospiro[β-carboline-1,3'-indol]-2'(1'H)-one: The methylated tryptamine (30 mg, 0.160 mmol) and 5-chloroisatin (28.9 mg, 0.160 mmol) was dissolved in 0.56 mL absolute ethanol, followed by the addition of p-TsOH (3.04 mg, 0.016 mmol). The reaction mixture was stirred for 16 hours at 110° C. The reaction mixture was concentrated in vacuo. The product was isolated using flash column chromatography with 10-30% EtOAc in hexane, followed by isocratic 30% EtOAc in hexanes (50.3 mg, 89%). $^1$H NMR (300 MHz, DMSO-$d_6$): δ 10.68 (s, 1H), 7.49 (d, J=7.2 Hz, 1H), 7.36 (dd, J=8.4, 1.8 Hz, 1H), 7.29 (d, J=8.1 Hz, 1H), 7.13 (td, J=7.2, 1.2 Hz, 1H), 7.07 (d, J=2.1 Hz, 1H), 7.03 (td, J=7.7, 1.2 Hz, 1H), 6.96 (d, J=8.1 Hz, 1H), 3.82-3.64 (m, 1H), 3.02 (s, 3H), 2.82 (dd, J=15.0, 3.6 Hz, 1H), 2.47 (dd, J=15.0, 10.5 Hz, 1H), 1.17 (d, J=6.6 Hz, 3H); MS (ESI) m/z 352.0 (M+H)$^+$.

The following compounds may be prepared using the same or analogous synthetic techniques and/or substituting with alternative reagents as described in the previous examples.

Example 91

(1R,3R)-5'-Chloro-6,7-difluoro-3-(trifluoromethyl)-2,3,4,9-tetrahydrospiro[β-carboline-1,3'-indol]-2'(1'H)-one (75)

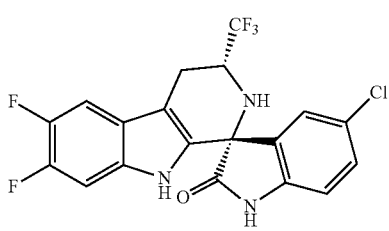

(1R,3R)-5'-Chloro-6,7-difluoro-3-(trifluoromethyl)-2,3,4,9-tetrahydrospiro[β-carboline-1,3'-indol]-2'(1'H)-one: $^1$H NMR (500 MHz, CDCl$_3$): δ 8.26 (s, 1H), 7.42 (s, 1H), 7.33 (dd, J=8.4, 2.1 Hz, 1H), 7.31-7.28 (m, 1H), 7.17 (d, J=1.9 Hz, 1H), 6.99 (dd, J=10.3, 6.5 Hz, 1H), 6.92 (d, J=8.4 Hz, 1H), 4.77-4.76 (m, 1H), 3.10 (dd, J=15.3, 4.4 Hz, 1H), 2.97 (dd, J=15.3, 11.0 Hz, 1H), 2.14 (d, J=3.8 Hz, 1H); MS (ESI) m/z 427.9 (M+H)$^+$; [α]$^{25}_D$: +205.3°.

Example 92

(1S,3S)-5'-Chloro-6,7-difluoro-3-(trifluoromethyl)-2,3,4,9-tetrahydrospiro[β-carboline-1,3'-indol]-2'(1'H)-one (76)

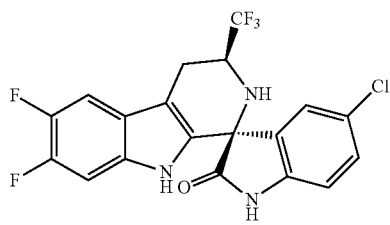

76

(1S,3S)-5'-Chloro-6,7-difluoro-3-(trifluoromethyl)-2,3,4,9-tetrahydrospiro[β-carboline-1,3'-indol]-2'(1'H)-one: $^1$H NMR (500 MHz, CDCl$_3$): δ 8.06 (s, 1H), 7.40 (s, 1H), 7.33 (dd, J=8.5, 2.0 Hz, 1H), 7.29-7.27 (m, 1H), 7.17 (d, J=2.0 Hz, 1H), 6.99 (dd, J=10.0, 6.5 Hz, 1H), 6.93 (d, J=8.0 Hz, 1H), 4.80-4.74 (m, 1H), 3.10 (dd, J=15.5, 4.5 Hz, 1H), 2.97 (dd, J=15.5, 11.0 Hz, 1H), 2.14 (d, J=4.2 Hz, 1H); MS (ESI) m/z 427.9 (M+H)$^+$; [α]$^{25}_D$: −202.6°.

Example 93

(1S,3S)-5'-Chloro-6-fluoro-3-(trifluoromethyl)-2,3,4,9-tetrahydrospiro[β-carboline-1,3'-indol]-2'(1'H)-one (77)

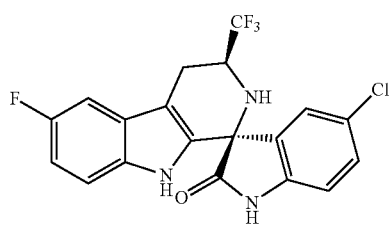

77

(1S,3S)-5'-Chloro-6-fluoro-3-(trifluoromethyl)-2,3,4,9-tetrahydrospiro[β-carboline-1,3'-indol]-2'(1'H)-one: $^1$H NMR (500 MHz, CDCl$_3$): δ 9.16 (s, 1H), 7.71 (s, 1H), 7.26-7.20 (m, 3H), 7.18 (d, J=2.0 Hz, 1H), 7.02-7.00 (m, 1H), 6.88 (d, JI=2.1 Hz, 1H), 6.80 (d, J=8.4 Hz, 1H), 4.74-4.73 (m, 1H), 3.13-3.09 (m, 1H), 2.98 (dd, I=15.2, 11.0 Hz, 1H), 2.20 (d, J=6.6 Hz, 1H); MS (ESI) m/z 410.0 (M+H)$^+$; [α]$^{25}_D$: −229.8.

Example 94

(1R,3R)-5'-Chloro-6-fluoro-3-(trifluoromethyl)-2,3,4,9-tetrahydrospiro[β-carboline-1,3'-indol]-2'(1'H)-one (78)

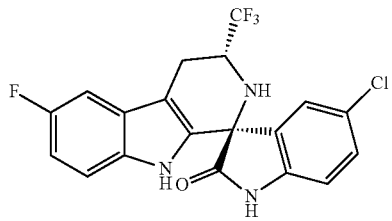

78

(1R,3R)-5'-Chloro-6-fluoro-3-(trifluoromethyl)-2,3,4,9-tetrahydrospiro[β-carboline-1,3'-indol]-2'(1'H)-one: $^1$H NMR (500 MHz, CDCl$_3$): δ 9.10 (s, 1H), 7.64 (s, 1H), 7.23 (dd, J=8.4, 1.9 Hz, 1H), 7.19 (dd, J=9.2, 2.1 Hz, 2H), 7.03-7.01 (m, 1H), 6.88 (d, J=2.2 Hz, 1H), 6.81 (d, J=8.4 Hz, 1H), 4.74-4.73 (m, 1H), 3.11 (dd, J=15.3, 4.3 Hz, 1H), 2.97 (dd, J=15.2, 11.0 Hz, 1H), 2.18 (d, J=7.2 Hz, 1H); MS (ESI) m/z 410.0 (M+H)$^+$; [α]$^{25}_D$: +220.8°.

Example 95

5',7-Dichloro-6-fluoro-3-methyl-2,3,4,9-tetrahydrospiro[β-carboline-1,3'-indol]-2'(1'H)-one (79)

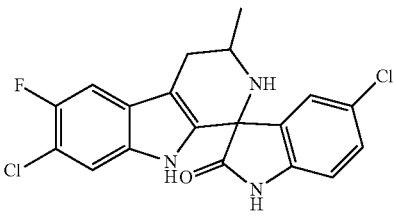

79

5',7-Dichloro-6-fluoro-3-methyl-2,3,4,9-tetrahydrospiro[β-carboline-1,3'-indol]-2'(1'H)-one: $^1$H NMR (500 MHz, DMSO-d$_6$): δ 10.69 (s, 1H), 10.51 (s, 1H), 7.43 (m, 1H), 7.32 (d, J=8.3 Hz, 1H), 7.26 (m, 1H), 7.04 (s, 1H), 6.93 (d, J=8.3 Hz, 1H), 3.91 (m, 1H), 3.12 (bd, J=5.5 Hz, 1H), 2.77 (bd, J=14.2 Hz, 1H), 2.38 (dd, J=14.2, 10.9 Hz, 1H), 1.16 (d, J=6.5 Hz, 1H); MS (ESI) m/z 390.0 (M)$^+$.

Example 96

5'-Chloro-6,7-difluoro-3-methyl-2,3,4,9-tetrahydrospiro[β-carboline-1,3'-indol]-2'(1'H)-one (80)

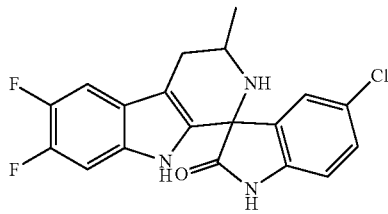

80

5'-Chloro-6,7-difluoro-3-methyl-2,3,4,9-tetrahydrospiro[β-carboline-1,3'-indol]-2'(1'H)-one: ¹H NMR (500 MHz, CDCl₃): δ 7.61 (bs, 1H), 7.34 (s, 1H), 7.30 (dd, J=9.0, 3.0 Hz, 1H), 7.26 (m, 1H), 7.18 (d, J=3.0 Hz, 1H), 6.99 (m, 1H), 6.88 (d, J=9.0 Hz, 1H), 4.21 (m, 1H), 2.91 (dd, J=15.0, 3.0 Hz, 1H), 2.51 (dd, J=15.0, 9.0 Hz, 1H), 1.32 (d, J=6.0 Hz, 1H); MS (ESI) m/z, 374.0 (M+H)⁺.

Example 97

(1R,3S)-5'-Chloro-6,7-difluoro-3-methyl-2,3,4,9-tetrahydrospiro[β-carboline-1,3'-indol]-2'(1'H)-one (81)

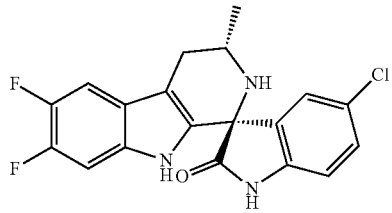

81

(1R,3S)-5'-Chloro-6,7-difluoro-3-methyl-2,3,4,9-tetrahydrospiro[β-carboline-1,3'-indol]-2'(1'H)-one: ¹H NMR (500 MHz, DMSO-d₆): δ 10.66 (bs, 1H), 10.49 (bs, 1H), 7.44 (m, 1H), 7.33 (dd, J=8.5, 2.0 Hz, 1H), 7.11 (m, 1H), 7.04 (d, J=2.0 Hz, 1H), 6.93 (d, J=8.5 Hz, 1H), 3.91 (m, 1H), 3.10 (bd, J=6.0 Hz, 1H), 2.76 (dd, J=15.0, 3.5 Hz, 1H), 2.38 (dd, J=15.5, 10.5 Hz, 1H), 1.17 (d, J=6.5 Hz, 1H); MS (ESI) m/z 374.0 (M+H)⁺; [α]²⁵_D: +198.4°.

Example 98

(1S,3R)-5'-Chloro-6,7-difluoro-3-methyl-2,3,4,9-tetrahydrospiro[β-carboline-1,3'-indol]-2'(1'H)-one (82)

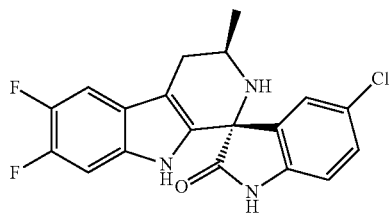

82

(1S,3R)-5'-Chloro-6,7-difluoro-3-methyl-2,3,4,9-tetrahydrospiro[β-carboline-1,3'-indol]-2'(1'H)-one: ¹H NMR (500 MHz, DMSO-d₆): δ 10.66 (bs, 1H), 10.49 (bs, 1H), 7.44 (m, 1H), 7.33 (dd, J=8.0, 2.0 Hz, 1H), 7.11 (m, 1H), 7.04 (d, 1.5 Hz, 1H), 6.93 (d, J=8.5 Hz, 1H), 3.91 (m, 1H), 3.10 (bd, J=5.5 Hz, 1H), 2.76 (dd, J=15.0, 3.5 Hz, 1H), 2.38 (dd, J=15.0, 10.5 Hz, 1H), 1.19 (d, J=7.0 Hz, 1H); MS (ESI) m/z 374.0 (M+H)⁺; [α]²⁵_D: −210.7°.

Example 99

5'-Chloro-6-fluoro-4-methyl-2,3,4,9-tetrahydrospiro[β-carboline-1,3'-indol]-2'(1'H)-one (83)

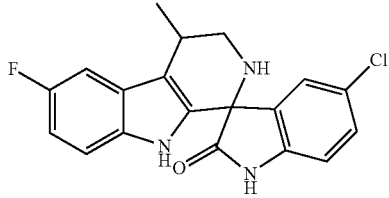

83

5'-Chloro-6-fluoro-4-methyl-2,3,4,9-tetrahydrospiro[β-carboline-1,3'-indol]-2'(1'H)-one: ¹H NMR (300 MHz, DMSO-d₆): δ 10.61 (s, 1H), 10.59 (s, 1H), 7.32 (m, 2H), 7.15 (dd, J=9.0, 3.0 Hz, 1H), 7.07 (d, J=3.0 Hz, 1H), 6.93 (d, J=9.0 Hz, 1H), 6.87 (td, J=9.0, 3.0 Hz, 1H), 3.13 (m, 5H), 1.33 (d, J=6.0 Hz, 3H); MS (ESI) m/z 356.3 (M+H)⁺.

II. Anti Activity of Compounds of the Invention

The compounds of the invention are active against parasites causing malaria, leishmaniasis and Chagas disease. The activities of the compounds of the invention may be shown in standard in vitro and in vivo tests.

Example A

In Vitro Assay

Representative Malaria Strain

The compounds of the invention and standard compounds are tested in vitro against two standard parasite strains: *Plasmodium falciparum*, NF54 (sensitive to all known drugs) and *Plasmodium falciparum*, K1 (chloroquine and pyrimethamine resistant). Chloroquine diphosphate (Sigma C6628), artemisinin (Sigma 36159-3), artesunate (Mepha), atovaquone (GSK) and proguanil (Roche) are used as the standard drugs. The testing is carried out in 96-well plates (Costar™ 96-well microtiter plates).

Smears of the stock cultures of the two strains are prepared and the parasitemia for each culture is determined. Cultures with parasitemia lower than 2% are not used.

Stock compound solutions are prepared in DMSO at 10 mg/mL. If insoluble in DMSO, other solvents may be used according to the recommendations of the supplier. The stocks may be kept at 4° C. for typically 2 or more weeks. For the assays, the compounds are further freshly diluted (4× dilution) with a screening medium (RPMI 1640 (10.44 g/L) (no hypoxanthine) supplemented with HEPES (5.94 g/L), NaHCO₃ (2.1 g/L), Neomycin (100 μg/mL)+Albumax^R II (5 g/L)).

100 μL of the screening medium is added to each well of the microtiter late using a multipette.

An infected red cells solution comprising parasitemia (p) of 0.3 and hematocrit (h) of 2.5% is prepared. Accordingly, the final concentrations of p and h in the assay are 0.3 and 1.25%, respectively.

Mix 0.3 ml of infected culture with 0.47 mL of blood and 9.23 ml of screening medium to obtain 10 ml of a final solution at 0.3% parasitemia/2.5% hematocrit.

1 mL of uninfected red cells solution (no parasites, 2.5% hematocrit) is prepared by mixing 50 μL of washed human erythrocytes or red blood cells (50% hematocrit; any blood group) with 950 μL of the screening medium.

100 μL of the screening medium containing 4× the highest compound concentration is added to the wells in row B. Six drugs can be tested in this manner on each plate. A reference substance is tested as well for each assay.

Serial drug dilutions are prepared with a multichannel pipette. 100 µL is taken from the wells of row B and transferred, after gentle mixing, to the wells of row C. After mixing, 100 µL is transferred from the wells of row C to the wells of row D. This is repeated consecutively for each row until row H. The 100 µL removed from the wells of row H are discarded. A two-fold serial dilution of drugs is thus obtained. For compounds that are too active, the highest concentration is appropriately lowered. The wells of row A serve as controls without drug.

100 µL of infected blood (parasitemia of 0.3%, 2.5% hematocrit) is added to each well with a multipette with a yellow tip on top to avoid spillage. Only the control wells (i.e. wells A9-A12) receive uninfected blood of 2.5% hematocrit.

The plates are incubated in an incubation chamber at 37° C. in an atmosphere containing a gas mixture of 93% $N_2$, 4% $CO_2$, and 3% $O_2$.

After 48 hours, 50 µL of $^3$H-hypoxanthine (=0.5 µCi) solution is added to each well of the plate. The plates are incubated for another 24 hours and may be frozen thereafter. If frozen, the plates are thawed for 1.5 hours before harvesting. The $^3$H-hypoxanthine solution is prepared by diluting a stock of 5 mCi/5 mL ex Amersham in half with 50% EtOH and then diluting 1 mL aliquots to 1/50 with the screening medium.

The plates are harvested with a Betaplate™ cell (Wallac, Zurich, Switzerland), which transfers the red blood cells onto a glass fiber filter and washes the filters with distilled water. The dried filters are inserted into a plastic foil with 10 mL of scintillation fluid and counted in a Betaplate™ liquid scintillation counter (Wallac, Zurich, Switzerland). The results are recorded as counts per minute (cpm) per well at each drug concentration.

Data is transferred into a graphic programme (e.g. EXCEL) and expressed as percentage of the untreated controls. The 50% inhibitory concentration ($IC_{50}$) value is evaluated by Logit regression analysis.

Thus for the novel compounds Examples 50 and 62:
NF54 (CQ sensitive P. falciparum strain):$IC_{50}$=0.9 nM Example 50 $IC_{50}$=3.4 nM Example 62

Example B

In Vivo Assay

The compounds of the invention are tested in vivo against standard parasite strains:
a) Representative Malaria (*Plasmodium*) Strain The *Plasmodium berghei*, GFP ANKA, strain described in B. Franke-Fayard et al., *Mol. Biochem. Parasitol.*, 137(1), 23-33, 2004 is used. This strain is maintained in female NMRI mice (20-22 g). The mice are kept in Standard Macrolon cages type II under standard conditions at 22° C. and 60-70% relative humidity, on a diet of pellets (PAB45-NAFAG 9009, Provimi Kliba AG, CH-4303 Kaiseraugst, Switzerland) and water ad libitum. Chloroquine (Sigma C6628) and artemisinin (Sigma 36, 159-3) are used as the standard drugs.

Stock compound bilious are prepared in 100% DMSO (suspended) or a solution consisting of 70% Tween-80 (d=1.08 g/mL) and 30% ethanol (d=0.81 g/mL), followed by a 10-fold dilution in $H_2O$.

On day 0, heparinized blood (containing 50 µL of 200 µg/mL Heparin) is taken from a donor mouse with approximately 30% a parasitemia and diluted in physiological saline to $10^8$ parasitized erythrocytes per mL. Of this suspension, 0.2 mL is injected intravenously (i.v.) into experimental groups of three mice, and a control group of five mice. Four hours post-infection, the experimental groups are treated with a single dose by the intraperitoneal (i.p.) route. Other routes of application are possible.

On days 1, 2 and 3 (24, 48 and 72 hours post-infection), the experimental groups are treated with a single daily dose per oral dosing (p.o). Other routes of application are possible. The dosage is determined by a preliminary toxicity test. A typical dosage of 50 mg/kg/day may be used for a compound of the invention. The drug concentration is adjusted such that 0.1 mL/10 g is injected.

On day 4, 24 hours after the last drug treatment, 1 µL tail blood is taken and dissolved in 1 mL PBS buffer. Parasitaemia is determined with a FACScan (Becton Dickinson) by counting 100,000 red blood cells. The difference between the mean value of the control group and those of the experimental groups is calculated and expressed as a percentage relative to the control group (=activity). For parasitemias lower than 0.1%, the presence of parasites in the FACS gate is checked visually (Fluorescence >$10^2$ is considered as positive). The survival of the animals is monitored for up to 30 days. Mice surviving for 30 days are checked for parasitemia and subsequently euthanised. A compound is considered curative if the animal survives to day 30 post-infection with no detectable parasites.

The results obtained are expressed as 1) a reduction of parasitaemia on day 4 in % as compared to the untreated control group, and 2) mean survival compared to the untreated control group. Thus for the novel compounds (examples 50 and 62):

| ED50 in P. berghei mouse model (mg/kg) | 1.2 | 1.5 |
|---|---|---|
|  | (example 50) | (example 62) |

Industrial Applicability

The compounds of the invention have useful pharmaceutical properties. In particular, the compounds are useful in the treatment and prevention of infections such as those caused by parasites of
a) *Plasmodium* eg *Plasmodium falciparum*, *Plasmodium vivax*, *Plasmodium malariae*, and *Plasmodium ovale*,
b) *Leishmania* genus such as, for example, *Leishmania donovani*, and
c) *Trypanosoma* eg *Trypanosoma cruzi*, and Chagas disease It is understood that the examples and embodiments described herein are for illustrative purposes only and that various modifications or changes in light thereof will be suggested to persons skilled in the art and are to be included within the spirit and purview of this application and scope of the appended claims.

The invention claimed is:
1. A compound of formula (I), or a pharmaceutically acceptable salt or ester thereof:

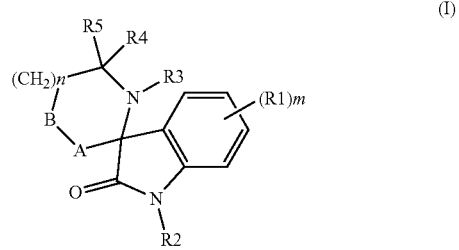

wherein
m is 1 or 2;
R1 is H, halogen, alkyl, haloalkyl, alkoxy, amine or aryl optionally substituted with one or more substituents;

R2 is H, alkyl, arylalkyl or alkoxycarbonyl;
R3 is H or alkyl;
R4 is H, alkyl or hydroxyalkyl or R3 and R4 form part of a heterocyclo ring;
R5 is H or alkyl;
n is 1, 2 or 3; and
A and B are fused to and form part of an unsubstituted or substituted indole;
provided that if A and B are fused to positions 2 and 3 of an unsubstituted indole, n is 1 or 2, R2 and R3 are H, m is 1 and R1 is in position 6 of the spiro oxindole, then
R1, R4 and R5 are not all H; or
if R1 is H, then R4 is not methyl when R5 is H and R5 is not methyl when R4 is H; or
if R1 is Br, then R4 and R5 are not both H, and R4 is not methyl when R5 is H, and R5 is not methyl when R4 is H.

2. A compound of formula (II), or a pharmaceutically acceptable salt or ester thereof:

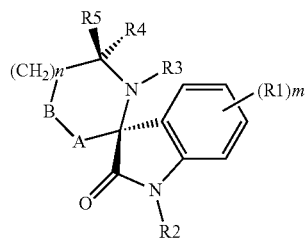

(II)

wherein:
m is 1 or 2;
R1 is H, halogen, alkyl, haloalkyl, alkoxy, amine or aryl optionally substituted with one or more substituents;
R2 is H, alkyl, arylalkyl or alkoxycarbonyl;
R3 is H or alkyl;
R4 is H, alkyl or hydroxyalkyl or R3 and R4 form part of a heterocyclo ring;
R5 is H or alkyl;
n is 1, 2 or 3; and
A and B are fused to and form part of an unsubstituted or substituted indole, provided that if A and B are fused to positions 2 and 3 of an unsubstituted indole, n is 1 or 2, R2 and R3 are H, m is 1 and R1 is in position 6 of the spiro oxindole, then
R1, R4 and R5 are not all H; or
if R1 is H, then R4 is not methyl when R5 is H and R5 is not methyl when R4 is H; or
if R1 is Br, then R4 and R5 are not both H, and R4 is not methyl when R5 is H, and R5 is not methyl when R4 is H.

3. The compound of claim 1, or a pharmaceutically acceptable salt or ester thereof, wherein m is 1 and R1 is Cl and in position 6 of the spiro oxindole.

4. The compound of claim 1, or a pharmaceutically acceptable salt or ester thereof, wherein n is 1, R3 is H and one of R4 and R5 is methyl.

5. A pharmaceutical composition comprising the compound of claim 1, or a pharmaceutically acceptable salt or ester thereof, in combination with a pharmaceutically acceptable excipient, diluent or carrier.

6. The pharmaceutical composition of claim 5 further comprising a second drug substance.

7. The compound of claim 2, or a pharmaceutically acceptable salt or ester thereof, wherein m is 1 and R1 is Cl and in position 6 of the spiro oxindole.

8. The compound of claim 2, or a pharmaceutically acceptable salt or ester thereof, wherein n is 1, R3 is H and one of R4 and R5 is methyl.

9. A pharmaceutical composition comprising the compound of claim 2, or a pharmaceutically acceptable salt or ester thereof, in combination with a pharmaceutically acceptable excipient, diluent or carrier.

10. A pharmaceutical composition comprising the compound of claim 2, or a pharmaceutically acceptable salt or ester thereof, in combination with a pharmaceutically acceptable excipient, diluent, or carrier and a second drug substance.

* * * * *